United States Patent
Guedat

(10) Patent No.: US 11,084,783 B2
(45) Date of Patent: Aug. 10, 2021

(54) O-ALKYL-BENZYLIDENEGUANIDINE DERIVATIVES AND THERAPEUTIC USE FOR THE TREATMENT OF DISORDERS ASSOCIATED WITH AN ACCUMULATION OF MISFOLDED PROTEINS

(71) Applicant: INFLECTIS BIOSCIENCE, Nantes (FR)

(72) Inventor: Philippe Guedat, Montenois (FR)

(73) Assignee: INFLECTIS BIOSCIENCE, Nantes (FR)

( * ) Notice: Subject to any disclaimer, the term of this patent is extended or adjusted under 35 U.S.C. 154(b) by 0 days.

(21) Appl. No.: 16/700,327

(22) Filed: Dec. 2, 2019

(65) Prior Publication Data

US 2020/0102269 A1   Apr. 2, 2020

Related U.S. Application Data

(62) Division of application No. 15/316,797, filed as application No. PCT/EP2015/065162 on Jul. 2, 2015, now Pat. No. 10,544,093.

(30) Foreign Application Priority Data

Jul. 2, 2014 (EP) .................................. 14306076

(51) Int. Cl.
| | |
|---|---|
| *C07C 281/18* | (2006.01) |
| *C07C 317/18* | (2006.01) |
| *C07C 323/12* | (2006.01) |
| *C07D 213/61* | (2006.01) |
| *C07D 295/108* | (2006.01) |
| *A61K 31/155* | (2006.01) |
| *A61K 31/44* | (2006.01) |
| *C07D 295/088* | (2006.01) |

(52) U.S. Cl.
CPC .......... *C07C 281/18* (2013.01); *A61K 31/155* (2013.01); *A61K 31/44* (2013.01); *C07C 317/18* (2013.01); *C07C 323/12* (2013.01); *C07D 213/61* (2013.01); *C07D 295/088* (2013.01); *C07D 295/108* (2013.01)

(58) Field of Classification Search
CPC ... C07C 281/18; C07C 317/18; C07C 323/12; C07D 213/61; C07D 295/088; C07D 295/108; A61K 31/155; A61K 31/44
See application file for complete search history.

(56) References Cited

FOREIGN PATENT DOCUMENTS

WO   WO1998023267   *   6/1998   ........... A61K 31/155

OTHER PUBLICATIONS

Bundgaard ("Design and Application of Prodrugs"in A Textbook of Drug Design and Development, 1991, Harwood Publishing, Chapters, p. 113-191).*

* cited by examiner

*Primary Examiner* — Robert H Havlin
(74) *Attorney, Agent, or Firm* — B. Aaron Schulman, Esq.; Stites & Harbison, PLLC

(57) ABSTRACT

The present invention relates to a compound of formula (I), or a tautomer and/or a pharmaceutically acceptable salt thereof,

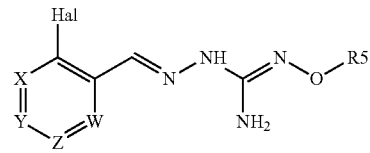

and its uses to treat a disorder associated with protein misfolding stress and in particular with an accumulation of misfolded proteins.

11 Claims, 5 Drawing Sheets

Figure 1:
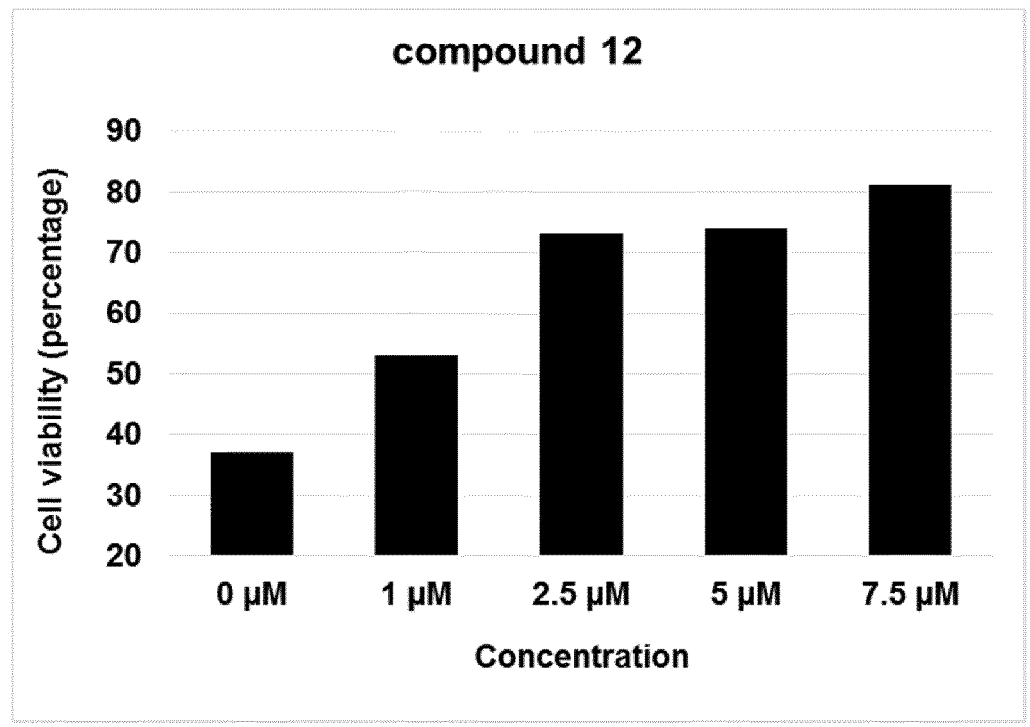

O-ALKYL-BENZYLIDENEGUANIDINE DERIVATIVES AND THERAPEUTIC USE FOR THE TREATMENT OF DISORDERS ASSOCIATED WITH AN ACCUMULATION OF MISFOLDED PROTEINS

CROSS-REFERENCE TO RELATED APPLICATIONS

This application is a continuation application of U.S. Ser. No. 15/316,797, having a filing date of Dec. 6, 2016, which was a 371 application of International application PCT/EP2015/065162, filed Jul. 2, 2015, which claimed the benefit of European patent application 14306076.2, filed Jul. 2, 2014, all of said applications incorporated herein by reference.

FIELD OF THE INVENTION

The present invention relates to compounds that have potential therapeutic applications in treating disorders associated with protein misfolding stress and in particular with an accumulation of misfolded proteins. In particular, the invention provides compounds that are capable of exhibiting a protective effect against cytotoxic endoplasmic reticulum (ER) stress.

BACKGROUND TO THE INVENTION

The compound 2-(2,6-dichlorobenzylidene)hydrazinecarboximidamide, also referred to as guanabenz, is an alpha agonist of the alpha-2 type that is used as an antihypertensive drug.

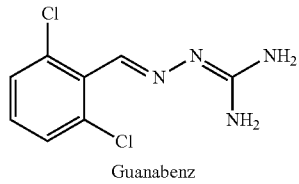

Guanabenz

Various derivatives of guanabenz have also been reported. For example, U.S. Pat. No. 3,982,020 (Sandoz, Inc.) discloses substituted benzylidene hydrazines and their use as hypoglycemic-antihyperglycemic agents, anti-obesity agents and anti-inflammatory agents. US 2004/0068017 (Bausch & Lomb Inc.) discloses substituted benzylidene hydrazines that are capable of increasing the activity of gelatinase A in ocular cells. The molecules have applications in the treatment of primary open angle glaucoma. WO 2008/061647 (Acure Pharma AB) discloses the use of N-(2-chloro-3,4,-dimethoxybenzylideneamino)guanidine as a VEGFR inhibitor and its associated applications in the treatment or prevention of undesired blood vessel formation during tumour growth and/or inflammatory conditions. WO2005/031000 (Acadia Pharmaceuticals, Inc.) discloses substituted benzylidene hydrazines and their use in treating acute pain and chronic neuropathic pain. Finally, EP1908464 (CNRS) discloses guanabenz and chloroguanabenz and their use in the treatment of polyglutamine expansion associated diseases, including Huntington's disease.

More recently it has been reported that guanabenz has therapeutic potential in a number of other areas. Guanabenz, was recently noted to have anti-prion activity (Tribouillard-Tanvier et al., 2008 PLoS One 3, e1981). It has been reported that its activity in protecting against protein misfolding is surprisingly much broader and includes attenuating accumulation of mutant Huntingtin in cell-based assays (WO2008/041133) and protection against the lethal effects of expression of misfolding prone Insulin Akita mutant in the endoplasmic reticulum (ER) of Min6 and INS-1 pancreatic beta-cells (Tsaytler et al., 2011 Science 332 pp91-94). WO2014/138298 and Way et al. (2015 Nature Communications 6:6532 DOI: 10.1038/ncomms7532) disclose guanabenz ant its use in the treatment of demyelinating disorder, such as multiple sclerosis.

Guanabenz has also been shown to promote survival of HeLa cells exposed to otherwise cytotoxic ER-stress induced by the N-glycosylation inhibitor tunicamycin, in a dose-dependent manner (Tsaytler, et al., Science, 2011). Quantitative assessment of cell viability revealed that guanabenz doubled the number of cells surviving ER stress with a median effective concentration of ~0.4 μM. Neither the α2-adrenergic receptor agonist clonidine, nor the α2-adrenergic receptor antagonist efaroxan protected cells from cytotoxic ER stress and efaroxan did not interfere with guanabenz's protective effect (Tsaytler, et al., Science, 2011). These observations demonstrate that guanabenz rescues cells from lethal ER stress by a mechanism independent of the α2-adrenergic receptor. Guanabenz protects cells from otherwise lethal accumulation of misfolded proteins by binding to a regulatory subunit of protein phosphatase 1, PPP1R15A (GADD34), selectively disrupting the stress-induced dephosphorylation of the a subunit of translation initiation factor 2 (eIF2α). Guanabenz sets the translation rates in stressed cells to a level manageable by available chaperones, thereby restoring protein homeostasis. It was reported that Guanabenz does not bind to the constitutive PPP1R15B (CReP) and therefore does not inhibit translation in non-stressed cells (Tsaytler, et al., Science, 2011).

Failure to maintain proteostasis in the ER by mounting an adequate unfolded protein response (UPR) is recognized as a contributing factor to many pathological conditions. Thus, the molecules described here, which inhibit eIF2a phosphatase to fine-tune protein synthesis, may be of therapeutic benefit to a large number of diseases caused protein misfolding stress and in particular with an accumulation of misfolded proteins.

Tribouillard-Tanvier et al., PLoS One 3, e1981 (2008) and EP1908464A disclose benzylidene guanidine derivatives comprising guanidine as a terminal group. However, the applicant has found that the terminal group is liable to metabolization which affects the biavailability of the compounds. Further, previous studies have also indicated that the (hetero)aryl group must be at least di-halogenated in order for the compounds to exhibit useful pharmacological activity (see for example, Tribouillard-Tanvier et al., PLoS One 3, e1981 (2008) and EP1908464A, CNRS). However, contrary to the results of previous studies, the present Applicant has surprisingly found that mono-halogenated (hetero)aryl derivatives comprising a modified terminal group may also be active. It is thus desirable to provide alternative, with enhanced activity and/or bioavailability profile.

The present invention seeks to provide alternative compounds based on a guanabenz core structure that have potential therapeutic applications in treating disorders associated with protein misfolding stress and in particular with an accumulation of misfolded proteins.

STATEMENT OF INVENTION

A first aspect of the invention relates to a compound of formula (I), or a pharmaceutically acceptable salt thereof,

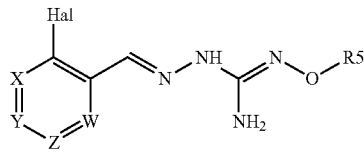

(I)

wherein:
Hal=F, Cl, Br, I
X is either –CR1= or —N=,
Y is either –CR2= or —N=,
Z is either –CR3= or —N=,
W is either –CR4= or —N=,
R1 is selected from H, Hal, alkyl and O-alkyl;
R2 is selected from H, Hal, alkyl, 0-alkyl and C(0)R6;
R3 is selected from H, Hal, alkyl and O-alkyl;
R4 is H, Cl, F, I or Br;
R5 is H or alkyl, cycloalkyl, aralkyl, alkenyl, cycloalkenyl, heterocyclyl, aryl, C(O)-alkyl, and C(O)-aryl, each of which is optionally substituted with one or more R7 groups;
R6 is selected from OH, 0-alkyl, 0-aryl, aralkyl, $NH_2$, NH-alkyl, $N(alkyl)_2$, NH-aryl, $CF_3$, alkyl and alkoxy;
each R7 is independently selected from halogen, OH, CN, COO-alkyl, aralkyl, heterocyclyl, S-alkyl, SO-alkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy.
And wherein if Hal is Cl and R4 is Cll, then R5 is not H.

A second aspect of the invention relates to a pharmaceutical composition comprising a compound of formula (II):

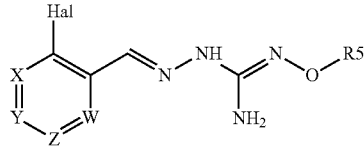

(II)

wherein:
Hal=F, Cl, Br, I
Xi s either —CR1= or —N=,
Y is either —CR2= or —N=,
Z is either —CR3= or —N=,
W is either —CR4= or —N=,
R1 is selected from H, Hal, alkyl and O-alkyl;
R2 is selected from H, Hal, alkyl, 0-alkyl and C(0)R6;
R3 is selected from H, Hal, alkyl and O-alkyl;
R4 is H, Cl, F, I or Br;
R5 is H or alkyl, cycloalkyl, aralkyl, alkenyl, cycloalkenyl, heterocyclyl, aryl, C(O)-alkyl, and C(O)-aryl, each of which is optionally substituted with one or more R7 groups;
R6 is selected from OH, O-alkyl, O-aryl, aralkyl, $NH_2$, NH-alkyl, $N(alkyl)_2$, NH-aryl, $CF_3$, alkyl and alkoxy;
each R7 is independently selected from halogen, OH, CN, COO-alkyl, aralkyl, heterocyclyl, Salkyl, SO-alkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy;
with a suitable pharmaceutically acceptable diluent, excipient or carrier.

A third aspect of the invention relates to a compound of formula (II), or a pharmaceutically acceptable salt thereof, for use in treating a disorder associated with protein misfolding stress in particular with accumulation of misfolded proteins, more specifically to proteopathies:

(II)

(II)

wherein:
Hal=F, Cl, Br, I
X is either —CR1= or —N=,
Y is either —CR2= or —N=,
Z is either —CR3= or —N=,
W is either —CR4= or —N=,
R1 is selected from H, Hal, alkyl and O-alkyl;
R2 is selected from H, Hal, alkyl, O-alkyl and C(O)R6;
R3 is selected from H, Hal, alkyl and O-alkyl;
R4 is H, Cl, F, I or Br;
R5 is H or alkyl, cycloalkyl, aralkyl, alkenyl, cycloalkenyl, heterocyclyl, aryl, C(O)-alkyl, and C(O)-aryl, each of which is optionally substituted with one or more R7 groups;
R6 is selected from OH, O-alkyl, O-aryl, aralkyl, $NH_2$, NH-alkyl, $N(alkyl)_2$, NH-aryl, $CF_3$, alkyl and alkoxy;
each R7 is independently selected from halogen, OH, CN, COO-alkyl, aralkyl, heterocyclyl, S-alkyl, SO-alkyl, $SO_2$-alkyl, $SO_2$-aryl, COOH, CO-alkyl, CO-aryl, $NH_2$, NH-alkyl, $N(alkyl)_2$, $CF_3$, alkyl and alkoxy.
And a pharmaceutically acceptable excipient.

Formula (I) is a particular embodiment of formula (II).

In a preferred embodiment, compounds of formula (I) or (II) as defined above advantageously exhibit no activity toward the adrenergic α2A receptor relative to prior art compounds such as Guanabenz. This loss in alpha-2 adrenergic activity renders the compounds therapeutically useful in the treatment of the disorders associated with protein misfolding stress and in particular with an accumulation of misfolded proteins. The absence of alpha-2 adrenergic activity means that compounds of formula (I) or (II) can be administered at a dosage suitable to treat the aforementioned diseases, without any significant effect on blood pressure.

DETAILED DESCRIPTION

As used herein, the term "alkyl" includes both saturated straight chain and branched alkyl groups. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl.

As used herein, the term "cycloalkyl" refers to a cyclic alkyl group. Preferably, the cycloalkyl group is a $C_{3-12}$ cycloalkyl group.

As used herein, the term "alkenyl" refers to a group containing one or more carbon-carbon double bonds, which may be branched or unbranched. Preferably the alkenyl group is a $C_{2-20}$ alkenyl group, more preferably a $C_{2-15}$ alkenyl group, more preferably still a $C_{2-12}$ alkenyl group, or preferably a $C_{2-6}$ alkenyl group, more preferably a $C_{2-3}$ alkenyl group. The term "cyclic alkenyl" is to be construed accordingly.

As used herein, the term "aryl" refers to a $C_{5-12}$ aromatic group. Typical examples include phenyl and naphthyl etc.

As used herein, the term "heterocycle" (also referred to herein as "heterocyclyl" and "heterocyclic") refers to a 4 to 12, preferably 4 to 6 memebered saturated, unsaturated or partially unsaturated cyclic group containing one or more heteroatoms selected from N, O and S, and which optionally further contains one or more CO groups. The term "heterocycle" encompasses both heteroaryl groups and heterocycloalkyl groups as defined below.

As used herein, the term "heteroaryl" refers to a 4 to 12 membered aromatic which comprises one or more heteroatoms. Preferably, the heteroaryl group is a 4 to 6 membered aromatic group comprising one or more heteroatoms selected from N, O and S. Suitable heteroaryl groups include pyrrole, pyrazole, pyrimidine, pyrazine, pyridine, quinoline, thiophene, 1,2,3-triazole, 1,2,4-triazole, thiazole, oxazole, iso-thiazole, iso-oxazole, imidazole, furan and the like.

As used herein, the term "heterocycloalkyl" refers to a 3 to 12 membered, preferably 4 to 6 membered cyclic aliphatic group which contains one or more heteroatoms selected from N, O and S. N-containing 5 to 6 membered heterocycloalkyl are preferred. Preferred heterocycloalkyl groups include piperidinyl, pyrrolidinyl, piperazinyl, thiomorpholinyl and morpholinyl. More preferably, the heterocycloalkyl group is selected from N-piperidinyl, N-pyrrolidinyl, N-piperazinyl, N-thiomorpholinyl and N-morpholinyl.

As used herein, the term "aralkyl" includes, but is not limited to, a group having both aryl and alkyl functionalities. By way of example, the term includes groups in which one of the hydrogen atoms of the alkyl group is replaced by an aryl group, e.g. a phenyl group. Typical aralkyl groups include benzyl, phenethyl and the like.

The followings are particular embodiments of formula (I) or (II):
In one preferred embodiment, Hal is Cl.
In one preferred embodiment, X is —CR1=.
In one preferred embodiment Y is —CR2=.
In another preferred embodiment, Y is N.
In one preferred embodiment Z=—CR3=.
In one preferred embodiment W=—CR4=.
In one preferred embodiment, R1 is H or F, more preferably H.
In one preferred embodiment, R2 is H or F, more preferably H.
In one preferred embodiment, R3 is H or F more preferably H.
In one preferred embodiment, R4 is H, Cl or F preferably H or F more preferably H.
In one preferred embodiment, R3 and R4 are both H.
In one embodiment, R5 is H, alkenyl or alkyl, each of alkenyl or alkyl being optionally substituted with one or more R7 groups.
In one embodiment, R7 groups are chosen from halogen, OH, heterocyclyl, SO-alkyl, $SO_2$-alkyl, Oalkyl.

In one especially preferred embodiment, the compound of formula (I) or (II) is selected from the following:

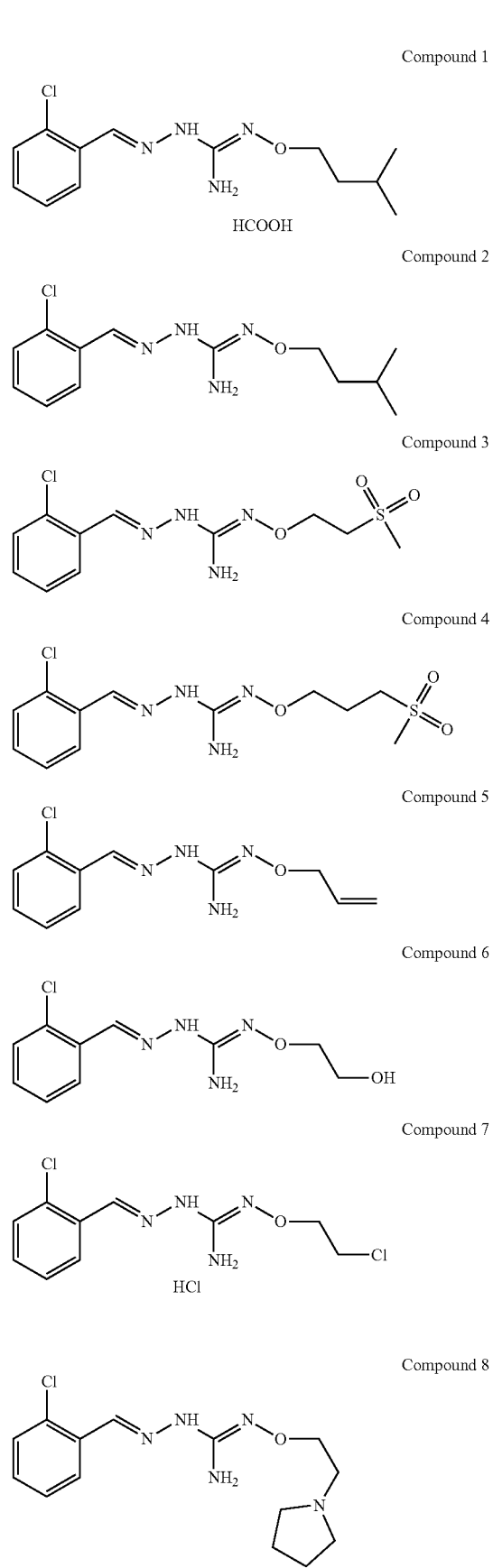

Compound 9
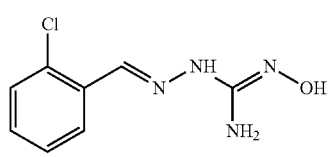 [SMILES: N/C(=N\O)N/N=C/c1ccccc1Cl]

Compound 10
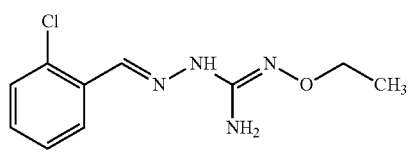 [SMILES: CCO/N=C(\N)N/N=C/c1ccccc1Cl]

Compound 11
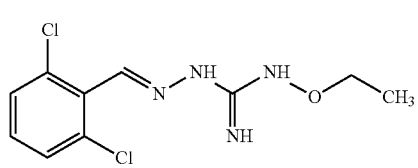

Compound 12
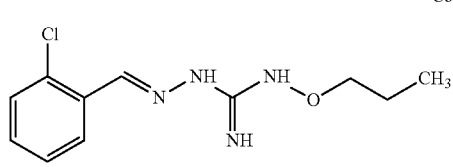

Compound 13
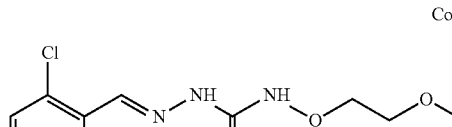

Compound 14

Compound 15
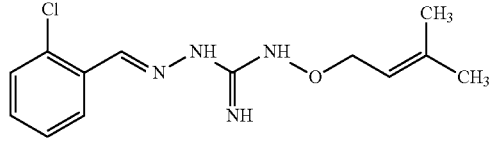

Compound 16
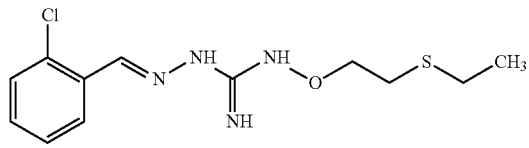

Compound 17
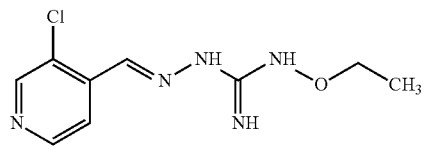

Compound 18
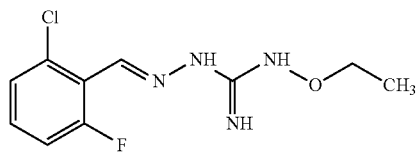

Compound 19
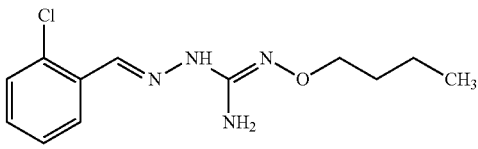 [SMILES: CCCCO/N=C(\N)N/N=C/c1ccccc1Cl]

Compound 20
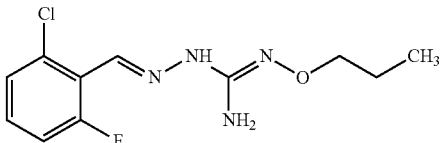

Compound 21
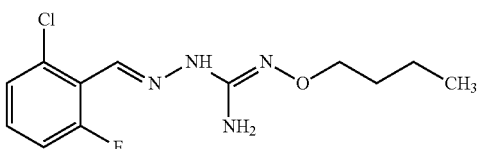

Compound 22
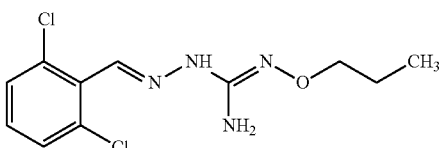

Compound 23
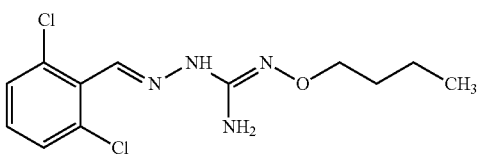 [SMILES: CCCCO/N=C(\N)N/N=C/c1c(F)cccc1Cl]

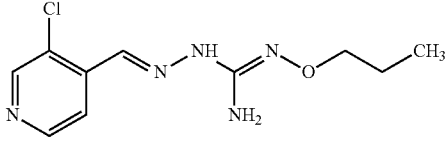 [SMILES: CCCO/N=C(\N)N/N=C/c1ccncc1Cl]

and pharmaceutically acceptable salts thereof.

In a preferred embodiment, the compound of formula (I) or (II) is selected from Compounds 4, 6, 10, 11, 12, 14, 17, 18 as set out above, more preferably selected from Compounds 4, 11, 17, 18 as set out above.

COMPOUNDS

One aspect of the invention relates to compounds of formulae (I), or pharmaceutically acceptable salts thereof, as defined above. Preferred aspects of the invention apply mutatis mutandis. Particularly preferred compounds for this aspect of the invention include Compounds 1, 2, 5 and 10 as described herein.

PROCESS OF PREPARATION

A further aspect of the invention relates to a process for preparing a compound of formula (I) or (II) or pharmaceutically acceptable salts thereof as above described, comprising the step of reacting a compound of formula (A) or a tautomer form thereof:

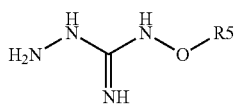

(A)

wherein R5 is as defined above
with a compound of formula (B):

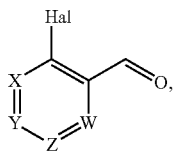

(B)

wherein X, Y, Z, W and Hal are as defined above, optionally followed by a step of modifying the R5 group of the compound resulting from the reaction between the compounds of formulae (A) and (B) as above described, into another R5 group.
Preferably, the process may also comprise a further step of purification of the compound (I) or (II), obtained above.

The coupling reaction between compounds (A) and (B) may be conducted in an organic solvent, such as an alcohol, eg ethanol. It may be carried out at a temperature comprised between room temperature and the boiling temperature of the reaction mixture.

The modification reaction of R5 groups may be conducted by application or adaptation of known methods. For example, in the compound obtained following the coupling of (A) and (B), R5 may be an alkyl group substituted by R7 groups: it may thus be desired to substitute R7 groups. Such substitution reactions are generally known. As a representative examples it may be desired to replace R7=OH with R7=halogen in a compound of formula (I) or (II). Such reaction may be conducted in the presence of an halogenating agent, such as a chlorinating agent, eg SOCl$_2$. Typically such a reaction may be conducting in an organic solvent such as dichloromethane. Another representative example is the substitution of R7=halogen with R7=N-containing heterocycle such as pyrrolidine. Such reaction may be conducted in the presence of a base, such as TEA. Typically such a reaction may be conducting in an organic solvent such as THF.

According to an embodiment, the process may further comprise the step of preparing the compound of formula (A) as above defined by reacting a compound of formula (C):

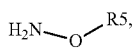

(C)

or one of its salts
wherein R5 is as defined above
with the S-methylisothiosemicarbazide hydroiodide compound (D):

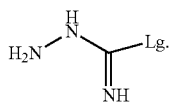

(D)

where Lg is a leaving group such as —S-Alkyl, e.g. —S-Methyl.

or one of its salts.

Typically, the reaction between the compounds of formulae (C) and (D) may be carried out in a basic aqueous solution, for example in an aqueous solution comprising sodium hydroxide.

The coupling reaction between compounds of formulae (C) and (D) may be followed a further step of purification.

In an embodiment, the process may optionally comprise a further step of preparing the compound of formula (C) by reacting a compound of formula (E):

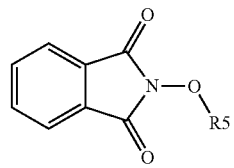

(E)

with a hydrazine derivative compound, for example hydrazine hydrate or methyl hydrazine.

The process of the invention may optionally comprise the step of preparing the compound of formula (E) from a compound of formula (E'):

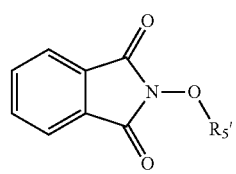

(E')

Where (R5') represents a precursor group of R5.

This reaction may be desired when (E) is not commercially available and it is not practicable to prepare (E) from (F) and (G) as disclosed below.

It may thus be desirable to use a precursor (E') which is to be transformed into (E).

A precursor is a group or a compound that may be modified into the desired compound by a substitution, elimination or otherwise derivation chemical reaction.

As an illustrative embodiment, the modification reaction of a R5' into the desired R5 group may be conducted by application or adaptation of known methods. For example, in (E), R5 may be an alkyl group substituted by R7 groups: it may thus be desired to modify R7' groups in (E') into the desired R7' in (E). Such modification reactions are generally known. As a representative example, it may be desired to replace the precursor R5' comprising the group R7'=S(Alkyl) with R7=SO$_2$(Alkyl). Such reaction may be conducted in the presence of MCPBA. Typically such a reaction may be conducting in an organic solvent such as dichloromethane.

The process of the invention may comprise the step of preparing (E) or (E') as appropriate, by reacting a compound (F)

$$Lg'-R5'' \quad (F)$$

(F)
Where R5" represents either R5 or R5' as defined above, and Lg' represents a leaving group such as a halogen atom or a hydroxyl (OH) group,
with N-hydroxyphtalimide (G):

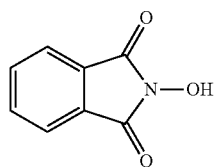

(G)

Generally, the coupling of (F) and (G) may be conducted according to a Gabriel synthesis conditions.

According to an illustrative embodiment, this reaction may be carried out in the presence of a base such as organic or mineral base, typically TEA or $K_2CO_3$, or NaOAc, in particular where Lg contains Halogen(s).

According to another illustrative embodiment, the first step may be carried out in the presence of diisopropyl azodicarboxylate and PPh3, in particular where Lg=OH.

Compounds (F), (G), (B) are generally commercially available.

The compounds of formula (D):

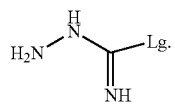

(D)

where Lg is a —S-Alkyl, e.g. —S-Methyl is also part of the invention.

In addition to the process disclosed above, the compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described herein, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Synthesis*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethyl-formamide; alcohols such as ethanol and methanol and ethers, such as diethyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

The process of the invention may also include the additional step of isolating the obtained product of formula (I).

The starting products and/or reagents may be commercially available, or may be readily prepared by the skilled person by applying or adapting the procedures disclosed in the experimental part below.

THERAPEUTIC APPLICATIONS

The compounds of formula (I) or (II) have potential therapeutic applications in treating disorders associated with accumulation of misfolded and/or unfolded proteins. In particular, compounds of formula (I) or (II) may have a protective effect against cytotoxic endoplasmic reticulum (ER) stress and age related disorders.

Another aspect of the invention relates to the use of a compound of formula (I) or (II) as defined above in the preparation of a medicament for treating a disorder associated with protein misfolding stress and in particular with an accumulation of misfolded proteins.

In one preferred embodiment of the invention, the compound of formula (I) or (II) is for use in treating diseases where accumulation of misfolded and/or unfolded proteins is involved in the mode of action (Brown et al, 2012, Frontiers in Physiology, 3, Article 263).

Another aspect of the invention relates to the use of a compound of formula (I) or (II) as defined above in the preparation of a medicament for treating proteopathies. The proteopathies refer to a class of diseases in which certain proteins become structurally abnormal, and thereby disrupt the function of cells, tissues and organs of the body. Often the proteins fail to fold into their normal conformation, and in this misfolded and/or unfolded state, the proteins can become toxic in some way (a gain of toxic function) or they can lose their normal function or they can have a reduce biological activity. The proteopathies, also known as proteinopathies, protein conformational disorders, or protein misfolding diseases, include many diseases such diseases as Alzheimer's disease, Parkinson's disease, prion disease, type 2 diabetes, amyloidosis, and a wide range of other disorders (see non limiting examples below).

As used herein the terms "proteinopathies, proteopathies, protein conformational disorders, protein misfolding diseases, diseases associated with protein misfolding stress, diseases associated with an accumulation of misfolded protein, diseases associated with a cytotoxic ER stress, UPR related diseases associated with have the same meaning and refer to diseases wherein certain protein become structurally abnormal and thereby disrupt the cellular homeostasis.

As used herein the terms "misfolded protein" and "unfolded protein" has the same meaning and refer to protein that fail to fold into their normal conformation.

As used herein the phrase "preparation of a medicament" includes the use of one or more of the above described compounds directly as the medicament in addition to its use in a screening programme for further active agents or in any stage of the manufacture of such a medicament.

Yet another aspect of the invention relates to a method of treating proteinopathy and/or a disorder associated with protein misfolding stress and in particular with an accumulation of misfolded proteins in a subject in need thereof, said method comprising administering a therapeutically effective amount of a compound of formula (I) or (II) as defined above to said subject.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

As used herein, the term «disease», «disorder», «conditions» has the same meaning. The disease is associated with an ER stress response activity and/or is associated with protein misfolding stress and in particular with an accumulation of misfolded proteins.

The term "therapeutically effective amount" refers to that amount of the compound being administered which will relieve to some extent one or more of the symptoms of the disease or disorder being treated.

In another embodiment, the invention relates to a compound of formula (I) or (II) as defined above for use in treating UPR disorders. The term "unfolded protein response" or UPR refers to a component of the cellular defence system against misfolded proteins that adapts folding in the endoplasmic reticulum (ER) to changing conditions. The UPR is activated in response to an accumulation of unfolded or misfolded proteins in the lumen of the endoplasmic reticulum. In this scenario, the UPR has two primary aims: (i) to restore normal function of the cell by halting protein translation, and (ii) to activate the signaling pathways that lead to the increased production of molecular chaperones involved in protein folding. If these objectives are not achieved within a certain time frame, or the disruption is prolonged, the UPR aims towards apoptosis. Upstream components of the UPR are the ER-resident trans-membrane proteins IRE1, ATF6, and PERK, which sense folding defects to reprogram transcription and translation in a concerted manner and restore proteostasis. Activated IRE1 and ATF6 increase the transcription of genes involved in ER folding, such as those encoding the chaperones BiP and GRP94. Activated PERK attenuates global protein synthesis by phosphorylating the subunit of translation initiation factor 2 (eIF2α) on Ser51 while promoting translation of the transcription factor ATF4. The latter controls expression of CHOP, another transcription factor, which in turn promotes expression of PPP1R15A/GADD34. PPP1R15A, an effector of a negative feedback loop that terminates UPR signaling, recruits a catalytic subunit of protein phosphatase 1 (PP1c) to dephosphorylate eIF2α, allowing protein synthesis to resume. UPR failure contributes to many pathological conditions that might be corrected by adequate boost of this adaptive response. Selective inhibitors of the stressed-induced eIF2a phosphatase PPP1R15A-PP1 delays eIF2α dephosphorylation and consequently protein synthesis selectively in stressed cells, without affecting protein synthesis in unstressed cells which constitutively expresses eIF2α phosphatase PPP1R15B-PP1. This prolongs the beneficial effects of the UPR. A transient reduction of protein synthesis is beneficial to stressed cells because decreasing the flux of proteins synthetized increases the availability of chaperones and thus protects from misfolding stress (Tsaytler et al., 2011 Science, 332, 91-94). Non-selective inhibitors of the 2 eIF2a phosphatases PPP1R15A-PP1 and PPP1R15B-PP1 might have undesirable effects, as persistent translation inhibition is deleterious. Indeed, genetic ablation of both PPP1R15A and PPP1R15B results in early embryonic lethality in mice indicating that inhibition of the two eIF2α phosphatases PPP1R15A-PP1 and PPP1R15B-PP1 is deleterious in an organismal context. In contrast, genetic ablation of PPP1R15A has no harmful consequence in mice (Harding et al., 2009, Proc. Natl. Acad. Sci. USA, 106, 1832-1837). Furthermore, specific inhibitors of PPP1R15A are predicted to be inert in unstressed cells, as the PPP1R15A is not expressed in absence of stress. Thus, selective PPP1R15A inhibitors are predicted to be safe. Non-selective inhibitors of the two elF2α phosphatases may also be useful to treat protein misfolding diseases, when used at doses that result in only a partial inhibition of the phosphatases.

Cytoprotection against ER stress can be measured by a suitable assay. For example, cytoprotection can be measured in HeLa cells in which ER stress is elicited by the addition of media containing tunicamycin, a mixture of homologous nucleoside antibiotics that inhibits the UDP-HexNAc: polyprenol-P HexNAc-1-P family of enzymes and is used to induce unfolded protein response. Cell viability can be detected in the presence and absence of inhibitor compounds after a set period of time, by measuring the reduction of WST-8 into formazan using a standard cell viability kit (such as Cell Viability Counting Kit-8 from Dojindo). Cytoprotection from ER stress is measured in terms of the percentage increase in viable cells (relative to control) after ER stress. Further details of a suitable assay are set forth in the accompanying Examples section.

In one preferred embodiment, the compound of formula (I) or (II) is capable of prolonging the protective effect of the UPR relative to the control (i.e. in the absence of inhibitor compound) by at least 10%, by at least 20%, more preferably, at least 30%, even more preferably, at least 40%, at least 50%, at least 60%, at least 70%, at least 80%, more preferably still, at least 90%.

The compounds of formula (I) or (II) are inhibitors of PPP1R15A-PP1 interaction which induce a protective effect. Preferably, the compound exhibits a protective effect with $EC_{50}$ of less than about 5 µM, even more preferably, less than about 2 µM, more preferably still, less than about 1 µM. The compound should preferably be devoid of alpha2 adrenergic activity. Thus, in one preferred embodiment the compound does not exhibit any activity in a functional alpha-2-adrenergic assay.

Certain compounds of formula (I) or (II) selectively inhibit PPP1R15A-PP1, and thus prolong the protective effect of the UPR, thereby rescuing cells from protein misfolding stress. Inhibitors of PPP1R15A-PP1 described in the present invention therefore have therapeutic applications in the treatment of a variety of diseases associated with protein misfolding stress and in particular with an accumulation of misfolded proteins, more specifically in the treatment of proteinopathies.

In one embodiment, the compound of formula (I) or (II) is capable of inhibiting PPP1R15A and PPP1R15B. In one preferred embodiment, the compound of formula (I) or (II) is capable of selectively inhibiting PPP1R15A over PPP1R15B.

In one embodiment, the invention relates to a compound of formula (I) or (II) as defined above for use in treating a disorder associated with the elF2α phosphorylation pathway where accumulation of misfolded proteins is involved in the mode of action. Preferably, the disorder is a PPP1R15A-related disease or disorder.

In another embodiment, the invention relates to a compound of formula (I) or (II) as defined above for use in treating a disorder caused by, associated with or accompanied by elF2α phosphorylation and/or PPP1R15A activity where accumulation of misfolded proteins is involved in the mode of action.

In another embodiment, the invention relates to a compound of formula (I) or (II) as defined above for use in treating UPR disorder such as, but not limited to aging (Naidoo et al., 2008, J Neurosci, 28, 6539-48).

As used herein, "PPP1R15A related disease or disorder" refers to a disease or disorder characterized by abnormal PPP1R15A activity where accumulation of misfolded proteins is involved in the mode of action. Abnormal activity refers to: (i) PPP1R15A expression in cells which normally do not express PPP1R15A; (ii) increased PPP1R15A expression; or, (iii) increased PPP1R15A activity.

In another embodiment, the invention relates to a method of treating a mammal having a disease state alleviated by the inhibition of PP1R15A, where accumulation of misfolded proteins is involved in the mode of action, wherein the method comprises administering to a mammal a therapeutically effective amount of a compound of formula (I) or (II) as defined above.

In another embodiment, the invention relates to a PPP1R15A inhibitor of formula (I) or (II) or a pharmaceutical acceptable salt thereof for the use in treating disorders associated with protein misfolding stress and in particular with an accumulation of misfolded proteins and/or UPR disorders, wherein said compound has no or reduced adrenergic alpha 2 agonist activity in comparison with Guanabenz.

In another embodiment, the invention relates to a PPP1R15A inhibitor of formula (I) or (II) or a pharmaceutical acceptable salt thereof for the use in treating disorders associated with protein misfolding stress and in particular with an accumulation of misfolded proteins and/or UPR disorders, wherein said compound does not inhibit protein translation in non-stressed cells expressing PPP1R15B.

In another embodiment, the invention relates to a method of treating a disorder characterized by ER stress response activity with an accumulation of misfolded proteins, the method comprising administering to a patient a therapeutically effective amount of at least one compound of formula (I) or (II) wherein said compound modulates ER stress response.

In another embodiment, the invention relates to PPP1R15A inhibitor of formula (I) or (II) or a pharmaceutical acceptable salt thereof for the use in treating disorders associated with protein misfolding stress and in particular with an accumulation of misfolded proteins and/or UPR disorders, wherein said compound has a selectivity towards PPP1R15A-PP1 holophosphatase, having but no or reduced activity towards PPP1R15B-PP1 holophosphatase, and wherein the ratio (activity towards PPP1R15A-PP1 holophosphatase/activity towards PPP1R15B-PP1) for said compound is at least equal or superior to the ratio (activity towards PPP1R15A-PP1 holophosphatase/activity towards PPP1R15B-PP1) for Guanabenz.

In another embodiment, the invention relates to a PPP1R15A inhibitor of formula (I) or (II) or a pharmaceutical acceptable salt thereof for the use in treating disorders associated with protein misfolding stress and in particular with an accumulation of misfolded proteins and/or UPR disorders, wherein:
  said compound has an activity towards PPP1R15A-PP1 holophosphatase but no or reduced activity towards PPP1R15B-PP1 holophosphatase, and;
  wherein the ratio (activity towards PPP1R15A-PP1 holophosphatase/activity towards PPP1R15B-PP1) for said compound is at least equal or superior to the ratio (activity towards PPP1R15A-PP1 holophosphatase/activity towards PPP1R15B-PP1) for Guanabenz; and
  wherein said compound has no or reduced adrenergic alpha 2 agonist activity in comparison with Guanabenz.

In another embodiment, the invention relates to a PPP1R15A inhibitor of formula (I) or (II) or a pharmaceutical acceptable salt thereof for the use in treating a disease or a condition characterized with at least one of (1) ER stress, (2) a cellular accumulation of unfolded or misfolded protein and (3) an UPR.

In another embodiment, the invention relates a PPP1R15A inhibitor of formula (I) or (II) or a pharmaceutical acceptable salt thereof for the use in treating a disease in a subject characterized by or associated with at least one of (1) endoplasmic reticulum (ER) stress, (2) a cellular accumulation of unfolded or misfolded proteins, and (3) an unfolded protein response.

The disease is associated with an ER stress response activity and/or is associated with protein misfolding stress and in particular with an accumulation of misfolded and/or unfolded proteins; more specifically the disease is a proteinopathy. Non limiting examples of disease according to the invention include, but are not limited to:

Neurodegenerative diseases such as tauopathies (such as Alzheimer's disease among others), synucleinopathies (such as Parkinson disease among others), Huntington disease and related polyglutamine diseases, polyalanine diseases (such as oculo-pharyngeal muscular dystrophy), prion diseases (also named transmissible spongiform encephalopathies), demyelination disorders such as Charcot-Marie Tooth diseases (also named hereditary motor and sensory neuropathy), leukodystrophies, amyotrophic lateral sclerosis (also referred to as motor neurone disease and as Lou Gehrig's disease) and multiple sclerosis.

Examples of tauopathies include, but are not limited to Alzheimer's disease, progressive supranuclear palsy, corticobasal degeneration, frontotemporal lobar degeneration (Pick's disease). FTD is a neurodegenerative disease characterized by progressive neuronal loss predominantly involving the frontal and/or temporal lobes; second only to Alzheimer's disease (AD) in prevalence, FTD accounts for 20% of young onset dementia cases. The involvement of UPR in tauopathies is well documented (see Stoveken 2013, The Journal of Neuroscience 33(36):14285-14287). Without to be bound by a theory, it is anticipated that compounds of the invention which are PPP1R15A inhibitors will ameliorate disease manifestations of tauopathies. In one preferred embodiment, the compound of formula (I) or (II) is for use in treating Alzheimer's disease. According to a preferred embodiment, the invention relates to a PPP1R15A inhibitor of formula (I) or (II) or a pharmaceutical acceptable salt thereof for the use in treating a disease selected among frontotemporal dementia (FTD), supranuclear palsy and corticobasal degeneration, preferably FTD.

Examples of synucleinopathies include, but are not limited to Parkinson's disease, dementia with Lewy bodies, pure autonomic failure, and multiple system atrophy. Recently, Colla et al. (J. of Neuroscience 2012 Vol. 32 N° 10 pp3306-3320) demonstrated that Salubrinal a small molecule that increases the phosphorylation of eIF2 alpha by inhibiting the PPP1R15A mediated dephosphorylation of eIF2 alpha (Boyce et al. 2005 Science Vol. 307 pp935-939), significantly attenuates disease manifestations in two animal models of alpha-synucleinopathy. The compounds of the invention which are PPP1R15A inhibitors will ameliorate disease manifestations of alpha-syncleinopathies such as Parkinson's disease. In one preferred embodiment, the compound of formula (I) or (II) is for use in treating alpha-syncleinopathies such as Parkinson's disease.

Examples of polyglutamine diseases include but are not limited to Spinobulbar muscular atrophy (or Kennedy disease), Huntington disease, Dentatorubral-pallidoluysian atrophy, Spinocerebellar ataxia type 1, Spinocerebellar ataxia type 2, Spinocerebellar ataxia type 3 (or Machado-Joseph disease), Spinocerebellar ataxia type 6, Spinocerebellar ataxia type 7 and Spinocerebellar ataxia type 17. Guanabenz is able to attenuate the accumulation of mutant Huntingtin in cell-based assays (WO2008/041133). This finding is unexpected since mutant huntingtin is either cytosolic or nuclear. However, there is evidence that mutant huntingtin metabolism has previously been connected to the ER stress response (Nishitoh et al., 2002, Genes Dev, 16, 1345-55; Rousseau et al., 2004, Proc Natl Acad Sci USA, 101, 9648-53; Duennwald and Lindquist, 2008, Genes Dev, 22, 3308-19). The findings that guanabenz protects cells from cytotoxic ER stress and reduces mutant huntingtin accumulation further supports the idea that there may be aspects of the ER stress response that impact on mutant huntingtin accumulation. However, Guanabenz is not useful for the treatment of human protein misfolding diseases due to its hypotensive activity. In contrast, the Guanabenz derivative PPP1R15A inhibitors devoid of alpha2 adrenergic activity of the invention could be useful to treat polyglutamine diseases and more specifically Huntington disease. In one preferred embodiment, the compound of formula (I) or (II) is for use in treating Huntington's disease.

Examples of polyalanine diseases include oculo-pharyngeal muscular dystrophy which is caused by poly-alanine tract in poly(A) binding protein nuclear 1 (PABPN1). Barbezier et al. (2011, EMBO Vol. 3 pp35-49) demonstrated that Guanabenz reduces aggregation in oculopharyngeal muscular atrophy. According to a preferred embodiment, the invention relates to a PPP1R15A inhibitor of formula (I) or (II) or a pharmaceutical acceptable salt thereof for the use in treating polyalanine diseases, more specifically oculopharyngeal muscular atrophy.

Examples of prion diseases of humans include but are not limited to classic Creutzfeldt-Jakob disease, new variant Creutzfeldt-Jakob disease (nvCJD, a human disorder related to Bovine spongiform encephalopathy), Gerstmann-Sträussler-Scheinker syndrome, fatal familial insomnia and kuru. Guanabenz reduces the symptoms of prion infected mice (D. Tribouillard-Tanvier et al., 2008 PLoS One 3, e1981). However, Guanabenz is not useful for the treatment of human protein misfolding diseases due to its hypotensive activity. In contrast, the Guanabenz derivative PPP1R15A inhibitors devoid of alpha2 adrenergic activity of the invention could be useful to treat prion diseases. According to a preferred embodiment, the invention relates to a PPP1R15A inhibitor of formula (I) or (II) or a pharmaceutical acceptable salt thereof for the use in treating a disease selected in the group of Creutzfeldt-Jakob disease, new variant Creutzfeldt-Jakob disease, Gerstmann-Sträussler-Scheinker syndrome, fatal familial insomnia and kuru.

Demyelination disorders are characterized by a loss of oligodendrocytes in the central nervous system or Schwann cells in the peripheral nervous system. The phenomenon associated with a demyelination disorder is characterized by a decrease in myelinated axons in the central nervous system or peripheral nervous system. Non-limiting examples of misfolded proteins of a myelinating cell (including oligodendrocyte and Schwann cell) is selected from the group consisting of CC1, myelin basic protein (MBP), ceramide galactosyltransferase (CGT), myelin associated glycoprotein (MAG), myelin oligodendrocyte glycoprotein (MOG), oligodendrocyte-myelin glycoprotein (OMG), cyclic nucleotide phosphodiesterase (CNP), myelin protein zero (MPZ), peripheral myelin protein 22 (PMP22), Connexin 32 (Cx32), protein 2 (P2), galactocerebroside (GalC), sulfatide and proteolipid protein (PLP). MPZ, PMP22, Cx32 and P2 are preferred misfolded proteins for Schwann cells. PLP, MBP, MAG are preferred misfolded proteins for oligodendrocytes.

In certain embodiments, the demyelination disorder is selected from the group consisting of Charcot-Marie Tooth (CMT) diseases. CMT refers to a group of hereditary neuropathy disorders characterized by a chronic motor and sensory polyneuropathy. Different types of CMT were identified such as CMT1, CMT2, CMT4, CMTX and Dejerine-Sottas disease. CMT subtypes may be further subdivided primarily on molecular genetic findings. For examples CMT1 is subdivided in CMT1A, 1B, 10, 1D, 1E, 1F/2E, 1X. Over a 100 mutations in the gene encoding myelin protein zero (P0), a single-pass transmembrane protein, which is the major protein produced by myelinating Schwann cells causes Charcot-Marie-Tooth neuropathy (D'Antonio et al., 2009, J Neurosci Res, 87, 3241-9). The mutations are dominantly inherited and cause the disease through a gain of toxic function (D'Antonio et al., 2009, J Neurosci Res, 87, 3241-9). Deletion of serine 63 from P0 (P0S63del) causes Charcot-Marie-Tooth 1B neuropathy in humans and a similar demyelinating neuropathy in transgenic mice. The mutant protein accumulates in the ER and induces the UPR (D'Antonio et al., 2009). Genetic ablation of CHOP, a pro-apoptotic gene in the UPR restores motor function in Charcot-Marie-Tooth mice (Pennuto et al., 2008, Neuron, 57, 393-405). The finding that PPP1R15A inhibition in cells nearly abolishes CHOP expression in ER-stressed cells indicates that genetic or pharmacological inhibition of PPP1R15A should reduce motor dysfunction in Charcot-Marie-Tooth mice. Recently, D'Antonio et al. (2013 J.Exp. Med Vol. pp1-18) demonstrated that P0S63del mice treated with salubrinal, regained almost normal motor capacity in rotarod analysis and was accompanied by a rescue of morphological and electro-physiological abnormalities. Accumulation of the of CMT-related mutant in the ER proteins is not unique to P0S63del; at least five other P0 mutants have been identified that are retained in the ER and elicit an UPR (Pennuto et al., 2008; Saporta et al., 2012 Brain Vol. 135 pp2032-2047). In addition, protein misfolding and accumulation of misfolded protein in the ER have been implicated in the pathogenesis of other CMT neuropathies as a result of mutations in PMP22 and Cx32 (Colby et al., 2000 Neurobiol.Disease Vol. 7 pp561-573; Kleopa et al., 2002 J. Neurosci. Res. Vol. 68 pp522-534; Yum et al., 2002 Neurobiol. Dis. Vol. 11 pp43-52). However, Salubrinal is toxic and cannot be used to treat human patients D'Antonio et al. (2013). In contrast, the PPP1R15A inhibitors of formula (I) or (II) are predicted to be safe and could be useful for the treatment of CMTs, preferably CMT-1, and more preferably CMT-1A, CMT-1B, CMT-1E, CMT-1X. In one preferred embodiment, the compound of formula (I) or (II) is for use in treating Charcot-Marie-Tooth diseases, preferably CMT-1, more preferably CMT-1A, CMT-1B, CMT-1E and CMT-1X. According to a preferred embodiment, the invention relates to a PPP1R15A inhibitor of formula (I) or (II) or a pharmaceutical acceptable salt thereof for the use in treating CMT, more preferably CMT-1 and Dejerine-Sottas disease. According to a preferred embodiment, the invention relates to a PPP1R15A inhibitor of formula (I) or (II) or a pharmaceutical acceptable salt thereof for the use in treating CMT associated with an accumulation of misfolded protein in the ER. According to a preferred embodiment, the invention relates to a PPP1R15A inhibitor of formula (I) or (II) or a pharmaceutical acceptable salt thereof for the use in treating CMT-1A. According to a preferred embodiment, the invention relates to a PPP1R15A inhibitor of formula (I) or a pharmaceutical acceptable salt thereof for the use in treating CMT-1B. According to a preferred embodiment, the invention relates to a PPP1R15A inhibitor of formula (I) or a pharmaceutical acceptable salt thereof for the use in treating CMT-1E. According to a preferred embodiment, the invention relates to a PPP1R15A inhibitor of formula (I) or a pharmaceutical acceptable salt thereof for the use in treating CMT-1X.

In another embodiment, the compound of formula (I) or (II) is for use in treating CMT, more preferably for use in treating CMT-1, in association with at least one compound selected in the group of D-Sorbitol, baclofen, pilocarpine, naltrexone, methimazole, mifepristone, ketoprofene and salts thereof. The compounds are combined for a grouped or separate administration, simultaneously or sequentially.

The invention relates to composition comprising a PPP1R15A inhibitor selected in the group of compound of formula (I) or (II), guanabenz and salubrinal or a pharmaceutical acceptable salt thereof, and at least one marketed compound and salts thereof, for use in the treatment of neurodegenerative diseases, preferably CMT, more preferably CMT-1. The dosage of compounds in the composition shall lie within the range of doses not above the usually prescribed doses for long term maintenance treatment or proven to be safe on phase 3 clinical trial; the most preferred dosage of compounds in the combination shall corresponds to amounts for 1% up to 10% of those usually prescribes for long term maintenance treatment.

Thus, the invention relates to composition comprising a PPP1R15A inhibitor selected in the group of compound of formula (I) or (II), guanabenz and salubrinal or a pharmaceutical acceptable salt thereof, and a compound increasing the expression of PMP22 protein, selected in the group of D-Sorbitol, baclofen, pilocarpine, naltrexone, methimazole, mifepristone, ketoprofene and salts thereof, for use in the treatment of CMT, preferably CMT-1, more preferably CMT-1A more preferably CMT-1A, CMT-1B, CMT-1E and CMT-1X.

In other embodiments, the demyelination disorder is selected from the group consisting of leukodystrophies. Examples of leukodystrophies include but are not limited to adrenoleukodystrophy (ALD), Alexander disease, Canavan disease, Krabbe disease, Metachromatic Leukodystrophy (MLD), Pelizaeus-Merzbacher disease (PMD), childhood ataxia with central nervous system hypomyelination (also known as vanishing white matter disease), CAMFAK syndrome, Refsum Disease, Cockayne Syndrome, Ver der Knapp Syndrome, Zellweger Syndrome, Guillain-Barre Syndrome (GBS), chronic inflammatory demyelinating polyneuropathy (CIDP), multifocal motor neuropathy (MMN) and progressive supernuclear palsy, progressive Multifocal Leuko-encephalopathy (PML), Encephalomyelitis, Central Pontine Myelolysis (CPM), Anti-MAG Disease, among others. Gow et al. (Neuron, 2002 Vol. 36, 585-596) demonstrated that the unfolded protein response is activated in PMD, and show that this pathway is duplication of, the PLP1 gene. According to a preferred embodiment, the invention relates to a PPP1R15A inhibitor of formula (I) or (II) or a pharmaceutical acceptable salt thereof for the use in treating leukodystrophies, and preferably Pelizaeus-Merzbacher disease (PMD).

Amyotrophic lateral sclerosis (ALS) is referred to as motor neurone disease and as Lou Gehrig's disease. It is now well recognized that protein misfolding plays a central role in both familial and sporadic ALS (Matus et al. 2013 Int. J. Cell Biol. ID674751 http://dx.doi.org/10.1155/2013/

674751). Saxena et al. (Nature Neuroscience 2009 Vol. 12 pp627-636) demonstrated that Salubrinal extends the life span of a G93A-SOD1 transgenic mouse model of motor neuron disease. More recently, Jiang et al. (Neuroscience 2014) demonstrated that Guanabenz delays the onset of disease symptoms, extends lifespan, improves motor performance and attenuates motor neuron loss in the SOD1 G93A mouse model of ALS. Without to be bound by a theory, it is anticipated that compounds of the invention which are guanabenz derivative PPP1R15A inhibitors will ameliorate disease manifestations of ALS with the SOD1 mutation G93A. Therefore, the compounds of formula (I) and (II) can be used to treat both familial and sporadic forms of ALS.

Examples of seipinopathies include, but are not limited to Berardinelli-Seip congenital lipodystrophy type 2 (BSCL2)-related motor disease, congenital generalized lipodystrophy (CGL), Silver syndrome, distal hereditary motor neuropathy type V (dHMN-V). The expression of mutant forms of seipin in cultured cells activates the unfolded protein response (UPR) pathway and induces ER stress-mediated cell death (Ito & Suzuki, 2009 Brain 132: 87-15). According to a preferred embodiment, the invention relates to a PPP1R15A inhibitor of formula (I) or (II) or a pharmaceutical acceptable salt thereof for the use in treating seipinopathy.

In another embodiment, the demyelination disorder referred therein is multiple sclerosis and related disease such as Schilder's disease. According to a preferred embodiment, the invention relates to a PPP1R15A inhibitor of formula (I) or (II) or a pharmaceutical acceptable salt thereof for the use in treating multiple sclerosis.

Cystic Fibrosis (CF)

Norez et al. (2008 Eur. J. Pharmacol. Vol. 592 pp33-40) demonstrated that Guanabenz activates Ca2+ dependent chloride currents in cystic fibrosis human airway epithelial cells. Without to be bound by a theory, it is anticipated that compounds of the invention which are guanabenz derivative PPP1R15A inhibitors will ameliorate disease manifestations of cystic fibrosis. According to a preferred embodiment, the invention relates to a PPP1R15A inhibitor of formula (I) or (II) or a pharmaceutical acceptable salt thereof for the use in treating cystic fibrosis.

Retinal Diseases

Recently published literature has provided evidences that the UPR is involved in the development of retinal degeneration: inherited retinal degeneration such as retinal ciliopathies & retinitis pigmentosa, macular degeneration, retinopathy of prematurity, light-induced retinal degeneration, retinal detachment, diabetic retinopathy and glaucoma (for review Gorbatyuk et Gorbatyuk 2013—Retinal degeneration: Focus on the unfolded protein response, Molecular Vision Vol. 19 pp1985-1998). Emerging evidence supports a role of ER stress in retinal apoptosis and cell death (Jing et al., 2012, Exp Diabetes Res, 2012, 589589).

Retinal ciliopathies are a group of rare genetic disorders originating from a defect in the primary cilium of photoreceptors thus inducing retinitis pigmentosa. This defect has been reported to induce an ER stress due to protein accumulation in the inner segment of the photoreceptor which in turn induces the UPR (WO2013/124484). Retinal degeneration is a very common feature in ciliopathies that can be observed either in isolated retinitis pigmentosa such as Leber's congenital amaurosis or X-linked retinitis pigmentosa, or also in syndromic conditions like the Bardet-Biedl Syndrome (BBS), the Alström syndrome (ALMS) or Usher syndrome. The retinal ciliopathy is selected from the group consisting of Bardet-Biedl syndrome, Senior-Loken syndrome, Joubert syndrome, Salidono-Mainzer syndrome, Sensenbrenner syndrome, Jeune syndrome, Meckel-Gruder syndrome, Alström syndrome, MORM syndrome, Leber's congenital amaurosis caused by mutation in a ciliary gene and X-linked retinitis pigmentosa caused by mutation in the RPGR gene.

Retinitis pigmentosa is an inherited, degenerative eye disease that causes severe vision impairment and often blindness. It is the most common cause of genetically determined blindness. Sufferers will experience one or more of the following symptoms: night blindness; tunnel vision (no peripheral vision); peripheral vision (no central vision); latticework vision; aversion to glare; slow adjustment from dark to light environments and vice versa; blurring of vision; poor color separation; and extreme tiredness. Retinitis pigmentosa (RP) is caused by over 100 mutations in the rhodopsin gene (Dryja et al., 1991, Proc Natl Acad Sci USA, 88, 9370-4). Rhodopsin is a G protein-coupled receptor that transduces light in the rod photoreceptors and consists of a covalent complex between the transmembrane protein opsin of 348 amino acids, covalently bound to 11-cis retinal (Palczewski, 2006, Annu Rev Biochem, 75, 743-67). The RP-causing rhodopsin mutations are mostly missense mutations distributed throughout the protein (Dryja et al., 1991), similar to the ALS-causing SOD1 mutations (Valentine et al., 2005, Annu Rev Biochem, 74, 563-93). The RP-causing rhodopsin mutants have been studied in diverse systems and results from heterologous expression of the proteins in mammalian cells, in transgenic mice and drosophila are consistent (Griciuc et al., 2011, Trends Mol Med, 17, 442-51). The most prevalent RP-causing rhodopsin mutants fail to fold, do not bind 11-cis-retinal, do not reach the cell surface but are retained in the ER (Griciuc et al., 2011, Trends Mol Med, 17, 442-51). Misfolding of the rhodopsin mutants causes ER stress and rod cell death (Griciuc et al., 2011). This strongly suggests that PPP1R15A inhibitors like Guanabenz but which advantageously exhibits no activity toward the adrenergic alpha2A receptor, like compounds of the invention, will ameliorate RP.

In one preferred embodiment, the compound of formula (I) or (II) is for use in treating retinal diseases, more preferably, inherited retinal degeneration such as retinal ciliopathies, retinitis pigmentosa, macular degeneration, retinopathy of premarurity, light-induced retinal degeneration, retinal detachment, diabetic retinopathy and glaucoma. According to a preferred embodiment, the invention relates to a PPP1R15A inhibitor of formula (I) or (II) or a pharmaceutical acceptable salt thereof for the use in treating syndromic retinitis pigmentosa and/or non-syndromic retinitis pigmentosa. According to a preferred embodiment, the invention relates to a PPP1R15A inhibitor of formula (I) or (II) or a pharmaceutical acceptable salt thereof for the use in treating Leber's congenital amaurosis. According to another preferred embodiment, the invention relates to a PPP1R15A inhibitor of formula (I) or a pharmaceutical acceptable salt thereof for the use in treating Bardet-Biedl syndrome. According to another preferred embodiment, the invention relates to a PPP1R15A inhibitor of formula (I) or a pharmaceutical acceptable salt thereof for the use in treating Alström syndrome. According to another preferred embodiment, the invention relates to a PPP1R15A inhibitor of formula (I) or a pharmaceutical acceptable salt thereof for the use in treating Usher syndrome.

Age-related macular degeneration (AMD) is the main cause of legal blindness among those over 65 years of age in the United States. Shen et al. (2011 Effect of Guanabenz on Rat AMD Models and Rabbit Choroidal Blood—Vol. 5 pp27-31) demonstrated that Guanabenz significantly protected retinal pigment epithelium (RPE) from NaIO3-induced degeneration, inhibited the development of choroidal neovascularization (CNV) in laser-induced rat AMD model and increased choroidal blood flow markedly in vivo. Guanabenz derivative compounds of the invention which are PPP1R15A inhibitors like Guanabenz but which advantageously exhibit no activity toward the adrenergic alpha2A receptor will be useful to treat retinal or macular degeneration.

In preferred embodiment, the compound of formula (I) is for use in treating retinal diseases, more preferably for use in treating diseases selected in the group of inherited retinal degeneration such as retinal ciliopathies, retinitis pigmentosa, macular degeneration, retinopathy of premarurity, light-induced retinal degeneration, retinal detachment, diabetic retinopathy and glaucoma in association with a compound increasing the expression and/or the activity of BIP protein, such as Valproic acid or a derivative thereof, trichostatin A, lithium, 1-(3,4-dihydroxy-penyl)-2-thiocyanate-ethanone and exendin-4. Thus, the invention relates to composition comprising a PPP1R15A inhibitor of formula (I) or a pharmaceutical acceptable salt thereof and a compound increasing the expression and/or the activity of BIP protein, preferably Valproic acid, for use in the treatment of diseases selected in the group of inherited retinal degeneration such as retinal ciliopathies, retinitis pigmentosa, macular degeneration, retinopathy of premarurity, light-induced retinal degeneration, retinal detachment, diabetic retinopathy and glaucoma. In preferred embodiment, the compound of formula (I) or (II), is for use in treating retinal diseases, more preferably for use in treating diseases selected in the group of inherited retinal degeneration such as retinal ciliopathies, retinitis pigmentosa, macular degeneration, retinopathy of premarurity, light-induced retinal degeneration, retinal detachment, diabetic retinopathy and glaucoma in association with a gene therapy vectors, Non limiting examples of gene therapy vectors include lentivirus, adenovirus, and adeno-associated vectors (AAVs); these vectors are effective in delivering genes of interest to the retina and retinal pigment epithelium for ocular gene therapy. It is anticipated that in an ocular gene therapy of inherited retinal degeneration associated with an accumulation of mutated misfolded proteins, protein accumulation in the endoplasmic reticulum will remain present while a normal protein is expressed from the gene therapy vector. It remains the need to decrease the protein accumulation/load in the cell, preferably in the ER with PPP1R15A inhibitors. The invention also relates to composition comprising PPP1R15A inhibitor selected in the group of compound of formula (I) or (II), guanabenz and salubrinal or a pharmaceutical acceptable salt thereof, in combination with ocular gene therapy.

Lysosomal Storage Diseases

Lysosomal storage diseases are a group of approximately 50 rare inherited metabolic disorders that result from defects in lysosomal function. The lysosomal dysfunction is usually the consequence of deficiency of a single enzyme required for the metabolism of lipids, glycoproteins or so-called mucopolysaccharides. Examples of lysosomal storage diseases which can be treated with by PPP1R15A inhibitors of formula (I) or (II) described herein include, but are not limited to, Activator Deficiency/GM2 gangliosidosis, alpha-mannosidosis, aspartylglucosaminuria, cholesteryl ester storage disease, cystinosis, Danon disease, Fabry disease, Farber disease, Niemann-Pick disease, fucosidosis, galactosialidosis, Gaucher disease (Types I, II, II), GM1 gangliosidosis (infantile, late infantile/juvenile, adult/chronic), I-cell disease/Mucolipidosis, Infantile free sialic acid storage disease/ISSD, Juvenile hexosaminidase A deficiency, Krabbe disease (infantile onset, late onset), lysosomal acid lipase deficiency (early onset/late onset), metachromatic leukodystrophy, mucopolysaccharidoses disorders (such as Pseudo-Hurler polydystrophy/mucolipidosis IIIA, mucopolysaccharidosis I (MPS I) Hurler syndrome, MPS I Scheie syndrome, MPS I Hurler-Scheie syndrome, MPS II Hunter syndrome, Sanfilippo syndrome Type A (MPS IIIA), Sanfilippo syndrome Type B (MPS IIIB), Sanfilippo syndrome Type C (MPS IIIC), Sanfilippo syndrome Type D (MPS IIID), Morquio Type A/MPS IVA, Morquio Type B/MPS IVB, MPS IX hyaluronidase deficiency, MPS VI Maroteaux-Lamy, MPS VII Sly syndrome, mucopolylipidosis 1/sialidosis, mucolipidosis IIIC, mucolipidosis type IV(multiple sulfatase deficiency, Niemann-Pick disease (Types A, B, C), CLN6 disease (atypical late infantile, late onset variant, early juvenile), Batten-Spielmeyer-Vogt/Juvenile NCL/CLN3 disease, Finnish Variant late infantile CLN5, Jansky-Bielschosky disease/late infantile CLN2/TPP1 disease, Kufs/Adult-onset NCL/CLN4 disease, Northern epilepsy/variant late infantile CLN8, Santavuori-Haltia/infantile CLN1/PPT disease, beta-mannosidosis, Pompe disease/glycogen storage disease type II, pycnodysostosis, Sandhoff disease/GM2 gangliosidosis (adult onset, infantile onset, juvenile onset), Schindler disease, Sall disease/sialic acid storage disease, Tay-Sachs/GM2 gangliosidosis, and Wolman disease. According to preferred embodiment, the invention relates to a PPP1 R15A inhibitor of formula (I) or (II) or a pharmaceutical acceptable salt thereof for the use in treating lysosomal storage diseases which are the consequence of deficiency of at least one single enzyme required for the metabolism of lipids, glycoproteins or so-called muco-polysaccharides and wherein said enzyme is misfolded in the endoplasmic reticulum (ER). According to a preferred embodiment, the lysosomal storage disease is Gaucher disease.

Amyloidosis Diseases

Amyloidosis is a non-specific term that refers to a number of different diseases collectively called amyloidoses. Amyloids are proteins whose secondary structure change, causing the proteins to fold in a characteristic form, the beta-pleated sheet. When the normally soluble proteins fold to become amyloids, they become insoluble, deposit and accumulate in organs or tissues, disrupting normal function. Different types of amyloidoses have different signs and symptoms depending on where and in which organs the amyloid proteins aggregate. Example of amyloidosis diseases includes, but are not limited to, AL, AH, ALH amyloidosis (amyloid derived from light-chain, heavy-chain, heavy and light chain antibodies respectively), AA amyloidosis (amyloid derived from derived from serum A protein), ATTR amyloidosis (amyloid derived from transthyrethin), primary systemic amyloidosis, secondary systemic amyloidosis, senile systemic amyloidodis, familial amyloid polyneuropathy 1, hereditary cerebral amyloid angiopathy, hemodialysis-related amyloidosis, familial amyloid polyneuropathy III, Finnish hereditary systemic amyloidosis, atrial amyloidosis, hereditary non-neuropathic systemic amyloidosis, injection—localized amyloidosis and hereditary renal amyloidosis and Alzheimer disease among others.

According to another preferred embodiment, the amyloid is Amyloid beta (Aβ or Abeta) and the invention relates to a PPP1R15A inhibitor of formula (I) or (II) or a pharmaceutical acceptable salt thereof for the use in treating Alzheimer disease.

According to another preferred embodiment, the amyloid is HLA-B27 (Colbert et al. 2009 Prion Vol. 3 (1) pp15-16) and the invention relates to a PPP1R15A inhibitor of formula (I) or (II) or a pharmaceutical acceptable salt thereof for the use in treating spondylo-arthropathies, more preferably ankylosing spondylitis.

Cancers

Cancer cells have high metabolic requirement and their proliferation relies on efficient protein synthesis. Translation initiation plays a crucial role in controlling protein homeostasis, differentiation, proliferation and malignant transformation. Increasing translation initiation contributes to cancer initiation and conversely, decreasing translation initiation could reduce tumor growth (Donze et al., 1995, EMBO J, 14, 3828-34; Pervin et al., 2008, Cancer Res, 68, 4862-74; Chen et al., 2011, Nat Chem Biol, 7, 610-6). Without wishing to be bound by theory, it is believed that inhibiting PPP1R15A could selectively reduce translation in tumor cells and thus reduce tumor growth. Examples of types of cancer which can be treated by PPP1R15A inhibitors of formula (I) or (II) disclosed herein include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, neuroblastoma, cervical cancer, ovarian cancer, liver cancer, bladder cancer, hepatoma, breast cancer, mammary cancer, colon cancer, colorectal cancer, endometrial carcinoma, salivary gland carcinoma, kidney cancer, renal cancer, prostate cancer, vulval cancer, thyroid cancer, hepatic carcinoma, osteosarcoma, stomach cancer, melanoma, multiple myeloma, medullary carcinoma of the thyroid and head and neck cancer.

Inflammation

PPP1R15A represents a promising target to control inflammation by blocking the release of inflammatory cytokines and other secreted molecular mediators leading to pathogenic conditions. Non-limiting examples of diseases or conditions having inflammation associated therewith which can be treated with by PPP1R15A inhibitors of formula (I) or (II) described herein include, but are not limited to infection-related or non-infectious inflammatory conditions in the lung (i.e., sepsis, lung infections, Respiratory Distress Syndrome, bronchopulmonary dysplasia, etc.); infection-related or non-infectious inflammatory conditions in other organs such as colitis, ulcerative colitis, Inflammatory Bowel Disease, diabetic nephropathy, hemorrhagic shock, spondylo-arthropathies, pancreatitis; inflammation-induced cancer (i.e., cancer progression in patients with colitis or Inflammatory Bowel Disease); and the like. Examples of such pathogenic inflammatory conditions include auto-immune diseases, hereditary diseases, chronic diseases and infectious diseases such as allergy, asthma, hypercytokinemia including graft versus host disease (GVHD), acute respiratory distress syndrome (ARDS), sepsis, systemic inflammatory response syndrome (SIRS) (see WO2011/061340). Preferably, infectious disease is selected from influenza virus infection, smallpox virus infection, herpes virus infection, severe acute respiratory syndrome (SARS), chikungunya virus infection, West Nile Virus infection, dengue virus infection, Japanese encephalitis virus infection, yellow fever virus infection, and hepatitis C virus infection.

Preferably auto-immune disease is selected from Sjogren's syndrome, systemic lupus erythematosus, psoriasis, dermatitis herpetiformis, vitiligo, mycosis fungoides, allergic contact dermatitis, atopic dermatitis, lichen planus, Pityriasis lichenoides et varioliforms acuta (PLEVA), arthritis, catastrophic antiphospholipid syndrome.

According to another preferred embodiment, the invention relates to a PPP1R15A inhibitor of formula (I) or (II), or a pharmaceutical acceptable salt thereof, for the use in treating a disease selected in the group of colitis, ulcerative colitis, Inflammatory Bowel Disease, pancreatitis, sepsis. According to another preferred embodiment, the invention relates to a PPP1R15A inhibitor of formula (I) or (II) or a pharmaceutical acceptable salt thereof, for the use in treating pancreatitis. According to another preferred embodiment, the invention relates to a PPP1R15A inhibitor of formula (I) or (II) or a pharmaceutical acceptable salt thereof, for the use in treating sepsis.

According to another preferred embodiment, the invention relates to a PPP1R15A inhibitor of formula (I) or (II), or a pharmaceutical acceptable salt thereof, for the use in treating spondylo-arthropathies, more preferably ankylosing spondylitis.

Metabolic and/or cardio-vascular disorders, such adiposity, hyper-lipidemia, familial hyper-cholesterolemia, obesity, atherosclerosis, hypertension, heart diseases, cardiac ischaemia, stroke, myocardial infraction, trans-aortic constriction, and diabetes and related disorders include hyperglycemia, impaired glucose tolerance, hyper-insulinemia (pre-diabetes), insulin hypersensitivity type I and II diabetes, insulin resistance, Wolcott-Rallison Syndrome among others.

In one preferred embodiment, the compound of formula (I) or (II) is for use in treating pre-diabetes or diabetes, more preferably type 2 pre-diabetes or type 2 diabetes. In another preferred embodiment, the compound of formula (I) or (II) is for use in treating a disease selected in the group of hyperglycemia, impaired glucose tolerance, hyper-insulinemia (pre-diabetes), insulin hypersensitivity type I and II, insulin resistance and Wolcott-Rallison Syndrome. Indeed, the insulin-secreting β-cells in the pancreas have a heavy and tightly regulated biosynthetic burden consisting in insulin secretion. Thus, these cells have an important need to maintain ER homeostasis (Back and Kaufman, 2012, Annu Rev Biochem, 81, 767-93). Type 2 diabetes is manifested by increased levels of blood glucose due to insulin resistance in the adipose, muscle and liver and/or impaired insulin secretion from pancreatic β-cells. As a response, β-cells mass increase and their function is enhanced. Eventually, the burden on the β-cells is too high leading to their progressive decline and death. Increasing evidence reveals that death of β-cells results from ER stress (Back and Kaufman, 2012, Annu Rev Biochem, 81, 767-93). Importantly, Chop deletion improves β-cells function in diverse models of diabetes (Song et al., 2008, J Clin Invest, 118, 3378-89). Without wishing to be bound by theory, it is believed that inhibitors of PPP1R15A-PP1 will improve β-cells function in type 2 diabetes since inhibition of PPP1R15A-PP1 reduces the levels of the pro-apoptotic protein CHOP during ER stress (Tsaytler et al., 2011, Science).

In another embodiment, the compound of formula (I) or (II) is for use in treating a disease selected in the group of hypertension, heart diseases, cardiac ischaemia, stroke, myocardial infraction, trans-aortic constriction or vascular stroke. In another preferred embodiment, the compound of formula (I) or (II) is for use in treating cardiac ischemia. In another preferred embodiment, the compound of formula (I) or (II) is for use in treating atherosclerosis.

Osteoporosis

Yokota et al. (BMC Musculoskeletal disorders 2013, 14, 197) and He et al. (Cellular Signaling 2013, 25 552-560) demonstrated that Salubrinal (Boyce et al. 2005) efficiently block osteoporosis in mice model and stimulates bone formation. However, Salubrinal is toxic and cannot be used to treat human patients. In contrast, the PPP1R15A inhibitors of formula (I) or (II) are predicted to be safe and could be useful for the treatment of osteoporosis. The compound of formula (I) or (II) is for use in treating osteoporosis.

Central Nervous System Trauma

Ohri et al. (Neurobiology of disease, 2013 Vol. 58 pp29-37) demonstrated that Salubrinal significantly improved hindlimb locomotion which corresponds with an improved white matter sparing and a decreased oligodendrocytes apoptosis, thus improving functional recovery after spinal cord injury. Therefore, the PPP1R15A inhibitors of formula (I) or (II) of the invention are predicted to be safe and could be useful to reduce the oligodendrocytes loss after traumatic spinal cord injury and for the treatment of spinal cord injury. In one preferred embodiment, the compound of formula (I) or (II) is for the prophylactic and/or therapeutic treatment of spinal cord injury.

Ischemia, Cerebral Ischemia, Sleep Apnoea

The present invention provides methods of using PPP1R15A inhibitors of formula (I) or (II) of the invention to prevent and/or treat tissue damage resulting from cell damage or death due to necrosis or apoptosis. Example of neural tissue damage include ischemia and reperfusion injury, such as cerebral ischemic stroke and head trauma. In one preferred embodiment, the compound of formula (I) or (II) is for the prophylactic and/or therapeutic treatment of cerebral ischemia, such as cerebral ischemic stroke and head trauma.

Aging

Aging is associated with the degeneration of cells, tissues, and organs, resulting in diseases such as cancer, cardiovascular failure, obesity, type 2 diabetes mellitus, non-alcoholic fatty liver, and neurodegenerative diseases, as well as the decline of most measures of physiological performance.

In biology, senescence is the state or process of aging. Cellular senescence is a phenomenon where isolated cells demonstrate a limited ability to divide in culture (the Hayflick Limit, discovered by Leonard Hayflick in 1961), while organismal senescence is the ageing of organisms. Organismal senescence is characterised by the declining ability to respond to stress, increasing homeostatic imbalance and the increased risk of disease; in particular, the UPR is impaired with age (Naidoo et al., 2008, J Neurosci, 28, 6539-48). Thus, prolonging the beneficial effect of the UPR by inhibition of eIF2α phosphatase could ameliorate age-related disorders. Therefore, the PPP1R15A inhibitors of formula (I) or (II) of the invention are predicted to be safe and could be useful to prevent and/or treat diseases or disorders relating to lifespan or proliferative capacity of cells, and diseases or disease conditions induced or exacerbated by cellular senescence in an animal, more specifically humans.

According to an embodiment, the present invention also concerns compounds of formula (I) or (II) for use in the treatment and/or prevention of a disorder selected in the group of tauopathies chosen from Alzheimer disease, progressive supranuclear palsy, corticobasal degeneration, frontotemporal lobar degeneration or frontotemporal dementia (FTD) (Pick's disease); synucleinopathies chosen from Parkinson's disease, dementia with Lewy bodies, pure autonomic failure, and multiple system atrophy; polyglutamine and polyalanine diseases chosen from Huntington disease, spinobulbar muscular atrophy (or Kennedy disease), dentatorubral-pallidoluysian atrophy, Spinocerebellar ataxia type 1, Spinocerebellar ataxia type 2, Spinocerebellar ataxia type 3 (or Machado-Joseph disease), Spinocerebellar ataxia type 6, Spinocerebellar ataxia type 7 and Spinocerebellar ataxia type 17, oculo-pharyngeal muscular dystrophy; demyelinating disorders like leukodystrophies, Charcot-Marie-Tooth disease and multiple sclerosis, cystic fibrosis, seipinopathies, lysosomal storage disorders, amyloidosis diseases, inflammation, metabolic disorders and cardio-vascular disorders chosen from adiposity, hyper-lipidemia, familial hyper-cholesterolemia, obesity, atherosclerosis, hypertension, heart diseases, cardiac ischaemia, stroke, myocardial infraction, trans-aortic constriction, vascular stroke; osteoporosis, nervous system trauma, ischemia, osteoporosis, retinal diseases, like retinitis pigmentosa, retinal ciliopathies, glaucoma, macular degeneration and aging.

According to an embodiment, the disorder is more particularly selected from multiple sclerosis; a leukodystrophy, preferably Pelizaeus-Merzbacher disease; a demyelinating disorder such as Charcot-Marie-Tooth, preferably CMT-1A; a cardio-vascular disorder such as hypertension, heart diseases, cardiac ischaemia, stroke, myocardial infraction, trans-aortic constriction; colitis, ulcerative colitis, Inflammatory Bowel Disease, pancreatitis, sepsis; an amyloidosis disease, such as Alzheimer disease and ankylosing spondylitis; pre-diabetes and diabetes, such as type-2 diabetes.

According to a further embodiment, the present invention also concerns a compound of formula (I) or (II) in association with a compound increasing the expression and/or the activity of BIP protein, for use in treating retinal diseases selected in the group of inherited retinal degeneration such as retinal ciliopathies, retinitis pigmentosa, macular degeneration, retinopathy of premarurity, light-induced retinal degeneration, retinal detachment, diabetic retinopathy and glaucoma.

PHARMACEUTICAL COMPOSITIONS

For use according to the present invention, the compounds or physiologically acceptable salts, esters or other physiologically functional derivatives thereof, described herein, may be presented as a pharmaceutical formulation, comprising the compounds or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine. Examples of such suitable excipients for the various different forms of pharmaceutical compositions described herein may be found in the "Handbook of Pharmaceutical Excipients, 2$^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including antioxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal, ocular and sublingual), rectal or parenteral (including subcutaneous, intradermal, intramuscular and intravenous), nasal, intra-ocularly and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Pharmaceutical formulations of the invention are suitable for ophthalmic administration, in particular for intra-ocular, topical ocular or peri-ocular administration, more preferably for topical ocular or peri-ocular administration.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient. As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

SALTS

The compounds of the invention can be present as salts, in particular pharmaceutically and veterinarily acceptable salts.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulfuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_{1-4}$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. According to a preferred embodiment the salt is acetate.

ENANTIOMERS/TAUTOMERS

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) and/or tautomeric characteristics. The corresponding enantiomers and/or tautomers may be isolated/prepared by methods known in the art. Enantiomers are characterised by the absolute configuration of their chiral centres and described by the R- and S-sequencing rules of Cahn, Ingold and Prelog. Such conventions are well known in the art (e.g. see 'Advanced Organic Chemistry', 3$^{rd}$ edition, ed. March, J., John Wiley and Sons, New York, 1985).

Compounds of formula (I) or (II) thus also include the tautomer forms of formula:

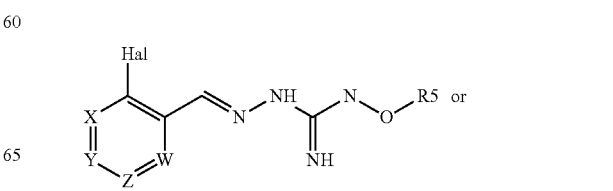

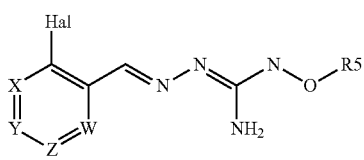

As an illustrative example, a tautomer form of Compound 2 is:

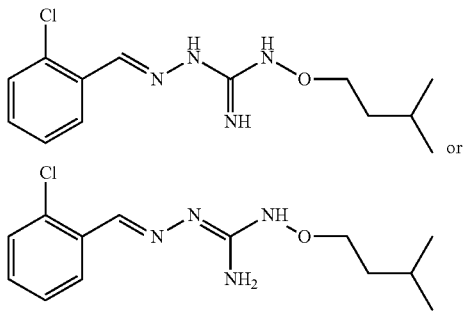

Compounds of the invention containing a chiral centre may be used as a racemic mixture, an enantiomerically enriched mixture, or the racemic mixture may be separated using well-known techniques and an individual enantiomer may be used alone.

STEREO AND GEOMETRIC ISOMERS

Some of the compounds of the invention may exist as stereoisomers and/or geometric isomers—e.g. they may possess one or more asymmetric and/or geometric centres and so may exist in two or more stereoisomeric and/or geometric forms as E/Z (Entgegen/Zusammen) isomers. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

Compounds of formula (I) or (II) thus also include the E and/or Z isomer forms of formula:

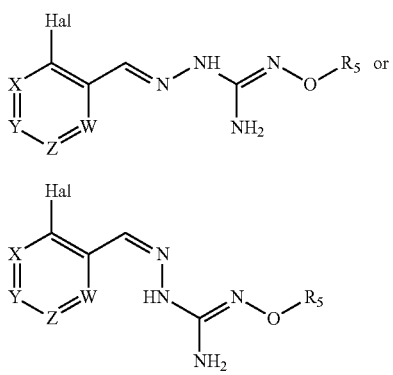

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulfur, fluorine and chlorine such as $^2H$, $^3H$, $^{13}C$, $^{14}C$, $^{15}N$, $^{17}O$, $^{18}O$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

PRODRUGS

The invention further includes the compounds of the present invention in prodrug form, i.e. covalently bonded compounds which release the active parent drug according to general formula (I) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

SOLVATES

The present invention also includes solvate forms of the compounds of the present invention. The terms used in the claims encompass these forms.

POLYMORPHS

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

ADMINISTRATION

The pharmaceutical compositions of the present invention may be adapted for rectal, nasal, intrabronchial, topical (including buccal, sublingual and ophthalmic administration, in particular for intra-ocular, intra-vitreal, topical ocular or peri-ocular administration), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, and even more preferably from 1-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally, intra-ocularly, topical, peri-ocularly or intramuscularly, and which are prepared from sterile or sterilisable solutions.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

DOSAGE

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of a compound of general formula (I) may be administered to target a particular condition or disease. Of course, this dosage amount will further be modified according to the type of administration of the compound. For example, to achieve an "effective amount" for acute therapy, parenteral administration of a compound of general formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at an effective concentration The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.1 to about 20 mg/kg. No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

COMBINATIONS

In a particularly preferred embodiment, the one or more compounds of the invention are administered in combination with one or more other active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining drugs are that it may promote additive or possible synergistic effects through biochemical interactions and also may decrease the emergence of resistance.

Beneficial combinations may be suggested by studying the inhibitory activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

According to preferred embodiment, the invention relates to a pharmaceutical composition comprising a PPP1R15A inhibitor of formula (I) or (II), or a pharmaceutical acceptable salt thereof, and a compound increasing the expression and/or the activity of protein BiP and a pharmaceutically acceptable carrier and/or excipient (see WO2013/124484). Preferably, the compound increasing the expression and/or activity of protein BiP is selected from the group consisting of valproic acid or a derivative thereof, trichostatin A, lithium, I-(3,4-dihydroxy-phenyl)-2-thiocyanate-ethanone, and exendin-4. According to a preferred embodiment the protein BiP is valproic acid or a derivative thereof such as 2-ene-valproic acid.

According to a preferred embodiment, the invention relates to a pharmaceutical composition comprising a PPP1R15A inhibitor of formula (I) or (II), or a pharmaceutical acceptable salt thereof, and a compound increasing the expression and/or the activity of protein BiP and a pharmaceutically acceptable carrier and/or excipient, to treat a disorder associated with the PPP1R15A pathway and associated with protein misfolding stress and in particular with accumulation of misfolded proteins. Preferably, the disease is selected in the group of cystic fibrosis, lysosomal storage disease, amyloidosis diseases, cancers, inflammation, metabolic disorders, cardio-vascular disorders, osteoporosis, central nervous system trauma, ischemia, retinal diseases, seipinopathies, tauopathies, synucleinopathies, polyglutamine and polyalanine diseases, neurodegenerative diseases, preferably Alzheimer's disease, Parkinson's disease, Amyotrophic Lateral Sclerosis, Huntington's disease, Charcot Marie Tooth diseases, leukodystrophies, multiple sclerosis.

ASSAY

A further aspect of the invention relates to the use of a compound as described above in an assay for identifying further candidate compounds capable of inhibiting PPP1R15A-PP1. Preferably, the assay is a competitive binding assay.

More preferably, the competitive binding assay comprises contacting a compound of the invention with PPP1R15A-PP1 and a candidate compound and detecting any change in the interaction between the compound according to the invention and the PPP1R15A-PP1.

Preferably, the candidate compound is generated by conventional SAR modification of a compound of the invention. As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with PPP1R15A-PP1 in the presence of a known substrate of PPP1R15A-PP1 and detecting any change in the interaction between said PPP1R15A-PP1 and said known substrate.

A further aspect of the invention provides a method of detecting the binding of a ligand to PPP1R15A-PP1, said method comprising the steps of:
(i) contacting a ligand with PPP1R15A-PP1 in the presence of a known substrate
(ii) detecting any change in the interaction between PPP1R15A-PP1 and said known substrate;
and wherein said ligand is a compound of the invention.

One aspect of the invention relates to a process comprising the steps of:
(a) performing an assay method described hereinabove;
(b) identifying one or more ligands capable of binding to a ligand binding domain; and
(c) preparing a quantity of said one or more ligands.

Another aspect of the invention provides a process comprising the steps of:
(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;

(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove. Yet another aspect of the invention relates to a pharmaceutical composition comprising a ligand identified by the method described hereinabove. Another aspect of the invention relates to the use of a ligand identified by the method described hereinabove in the preparation of a pharmaceutical composition for use in the treatment of a disorder associated with accumulation of misfolded and/or unfolded proteins as defined above.

The above methods may be used to screen for a ligand useful as an inhibitor of PPP1R15A-PP1.

Compounds of general formula (I) are useful both as laboratory tools and as therapeutic agents. In the laboratory certain compounds of the invention are useful in establishing whether a known or newly discovered target contributes a critical or at least significant biochemical function during the establishment or progression of a disease state, a process commonly referred to as 'target validation'.

BRIEF DESCRIPTION OF THE DRAWING FIGURES

The present invention is further described with reference to the following figures wherein:

FIG. 1 shows dose dependent protection of Hela cells by compound 12 of the invention from ER stress induced by 6 hour exposure to tunicamycin.

Figure 2:
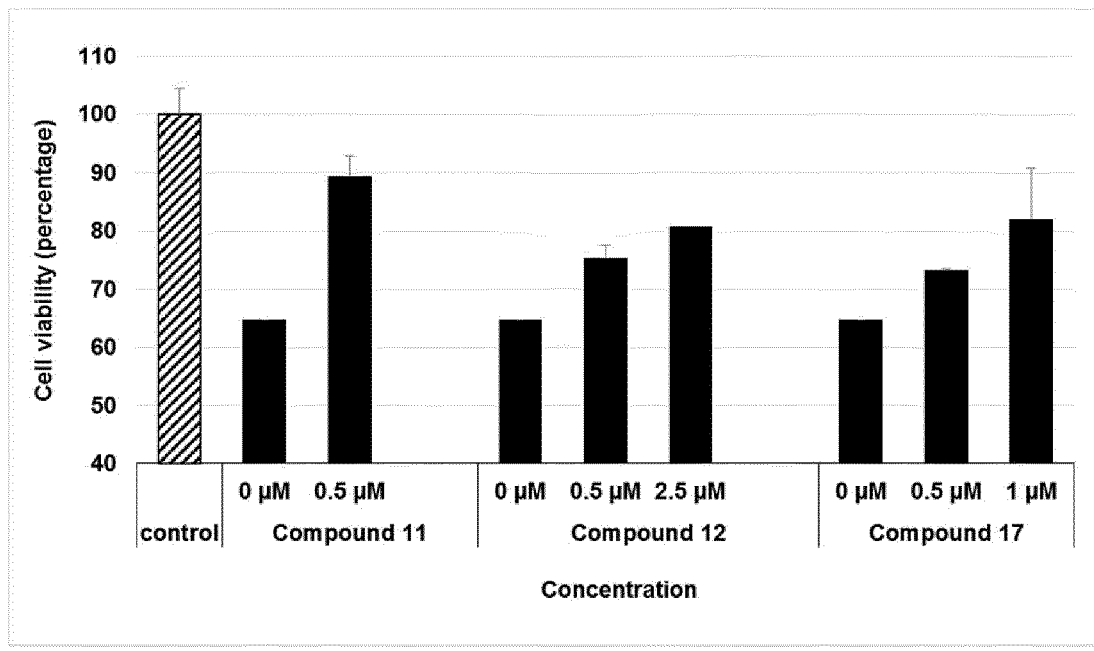

FIG. 2 shows dose dependent protection of interferon-gamma injured rat oligodendrocytes by compound 11, compound 12 and compound 17 of the invention.

Figure 3:
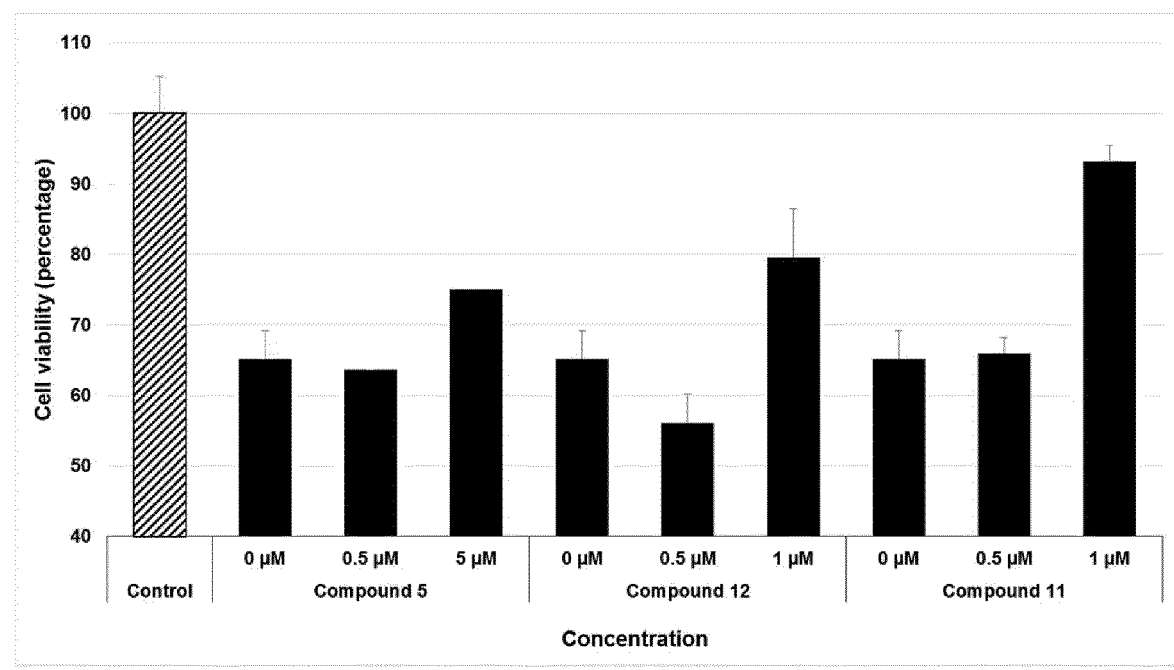

FIG. 3 shows dose dependent protection of rotenone injured primary mesencephalic rat neurons by compound 5, compound 12 and compound 17 of the invention.

Figure 4:
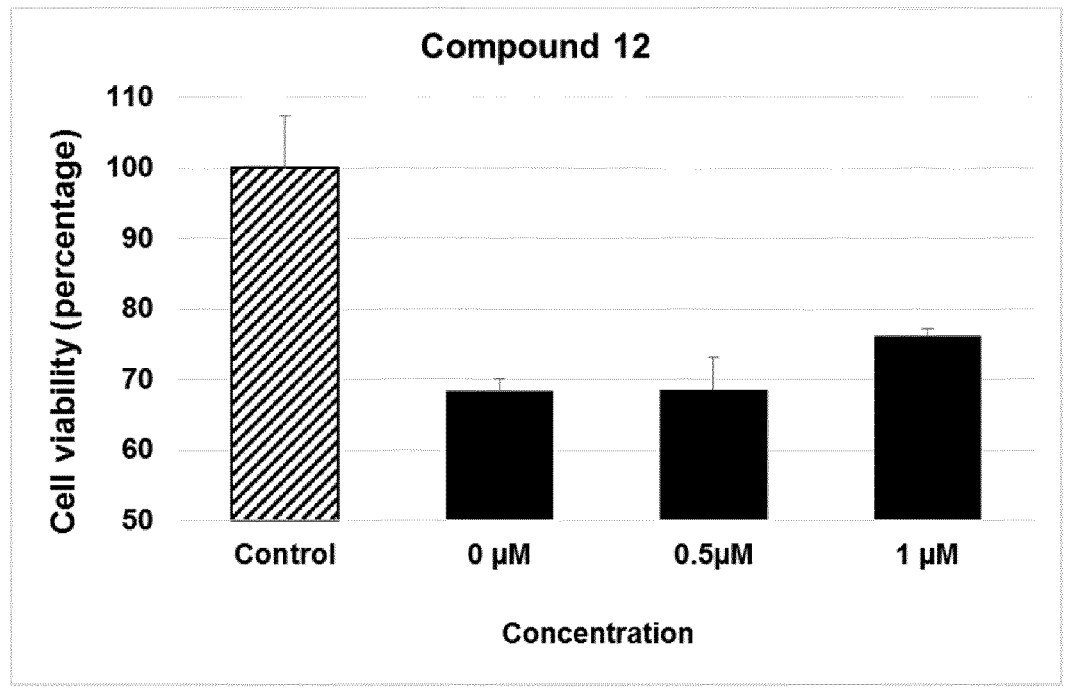

FIG. 4 shows dose dependent protection of amyloid-beta 1-42 injured primary cortical rat neurons by compound 12 of the invention.

Figure 5:
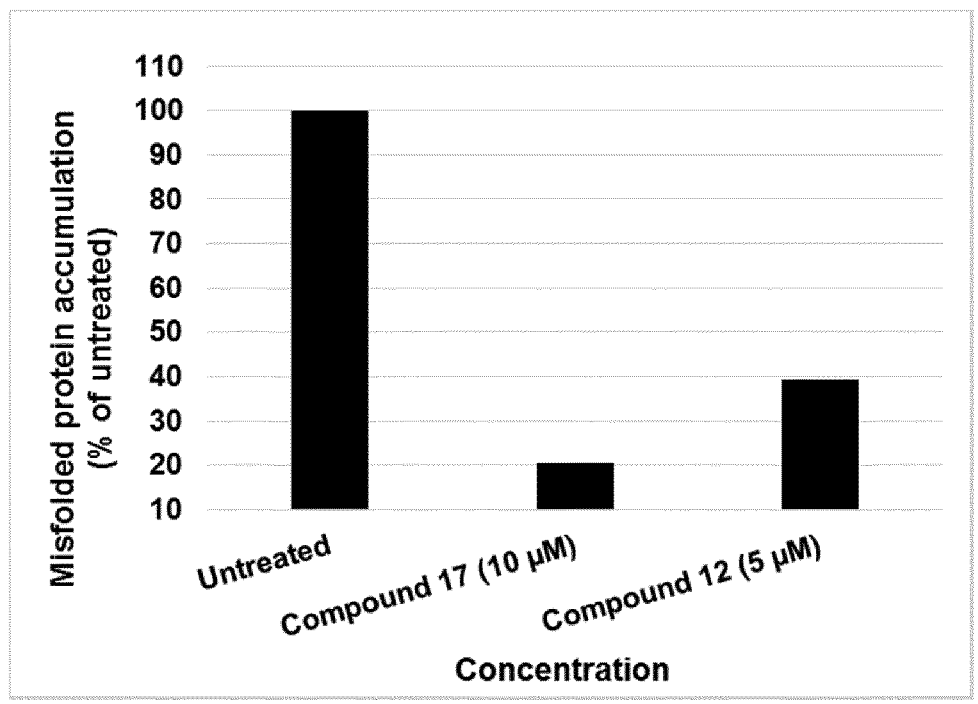

FIG. 5 shows the ability of compound 12 and compound 17 at 5 microM and 10 microM respectively to prevent the accumulation of T181P mutated DM20 protein in Human 293T cell.

Figure 6:
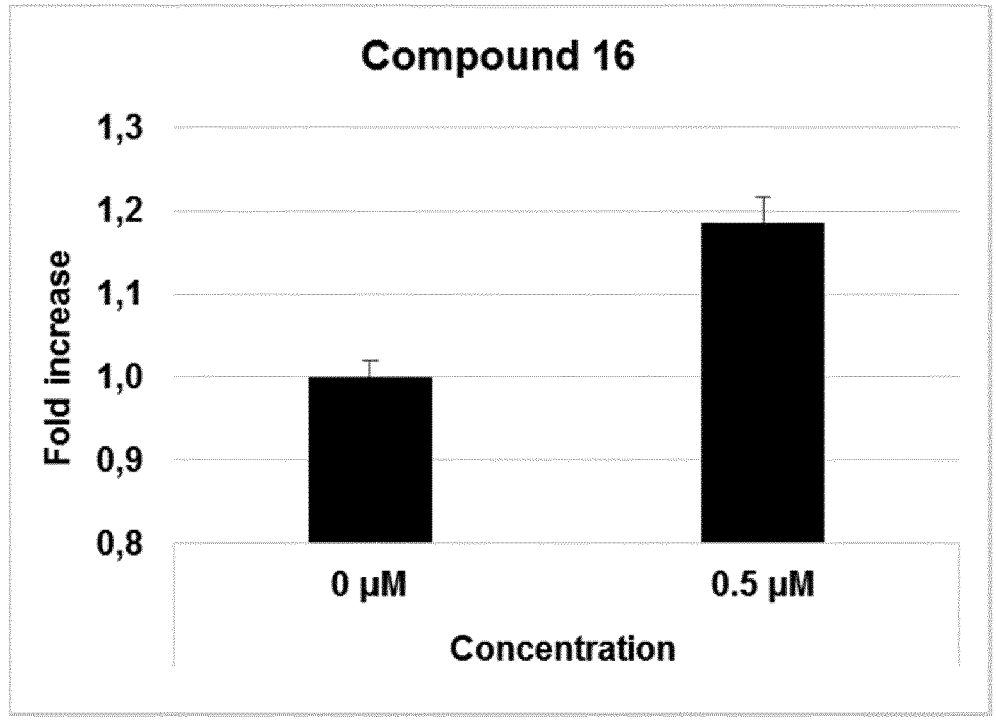

FIG. 6 shows the ability of compounds 16 to prevent cell death associated with the accumulation of misfold prone Insulin Akita expressed in Min6 cells.

Figure 7:
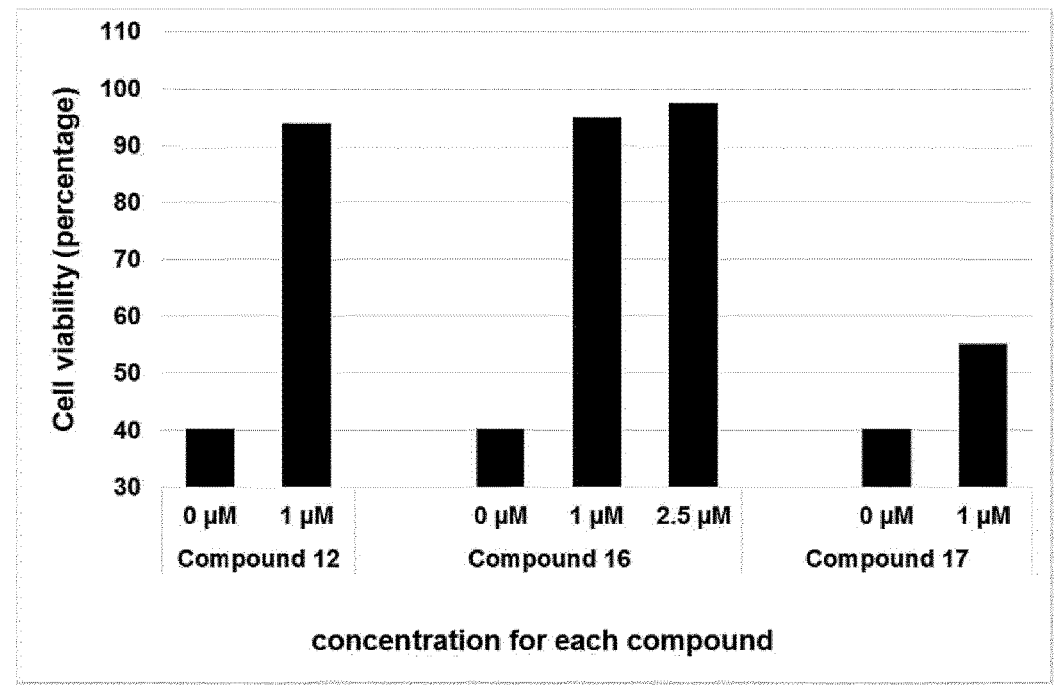

FIG. 7 shows the ability of compound 12, compound 16 and compound 17 at different concentrations to prevent Min6 insulinoma cell death associated with accumulation of misfolded protein induced by 6 hour exposure to tunicamycin.

Figure 8:
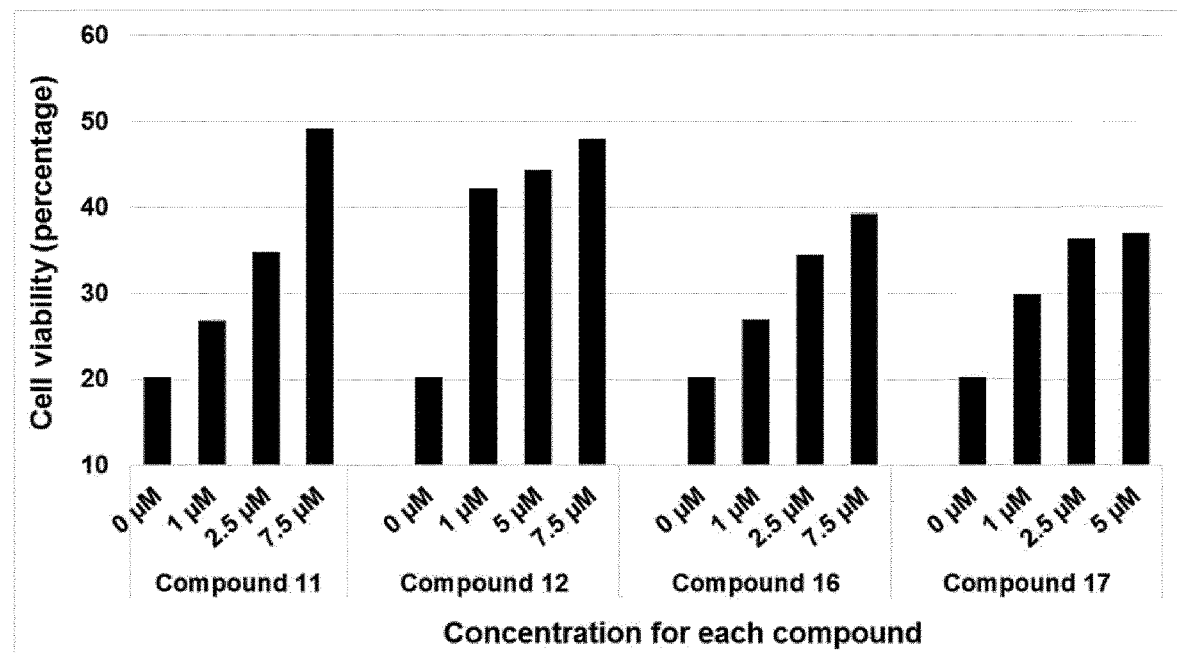

FIG. 8 shows the ability of compound 11, compound 12, compound 16 and compound 17 at different concentrations to prevent INS1 insulinoma cell death associated with accumulation of misfolded protein induced by 6 hour exposure to tunicamycin.

Figure 9:
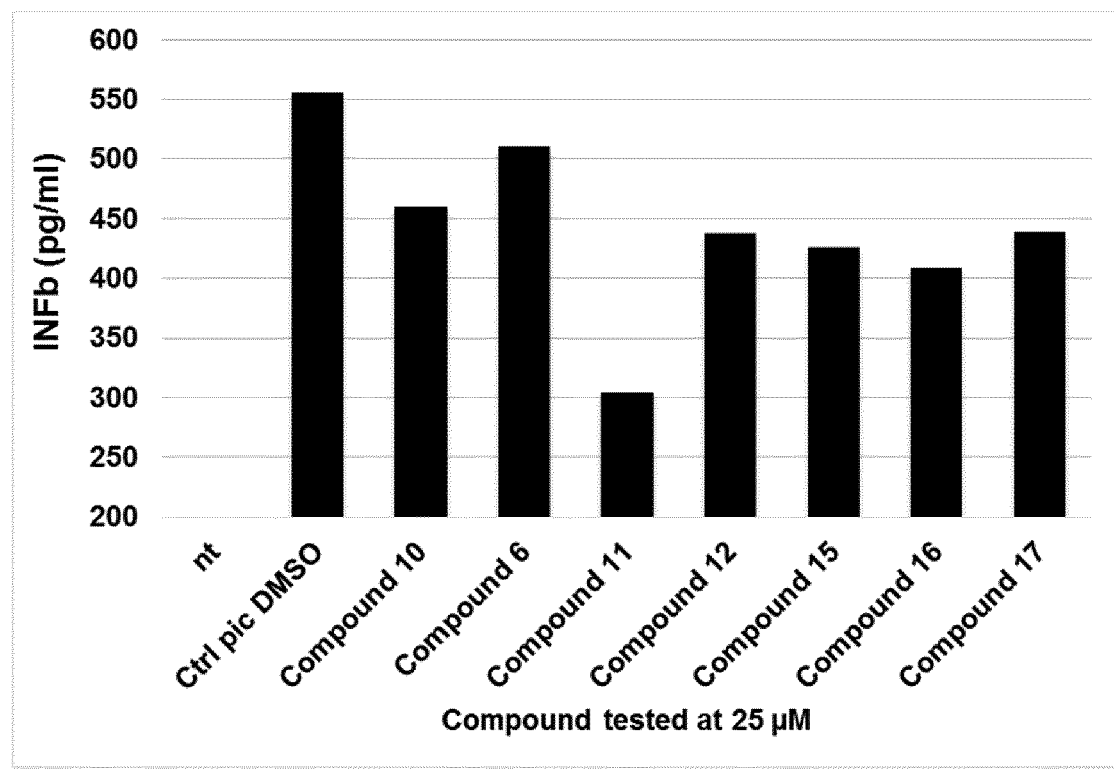

FIG. 9 shows the ability of compounds 6, 10, 11, 12, 15, 16 and 17 (at 25 microM) to prevent type-I interferon production by mouse embryonic fibroblasts lipofected with poly I:C.

Figure 10:
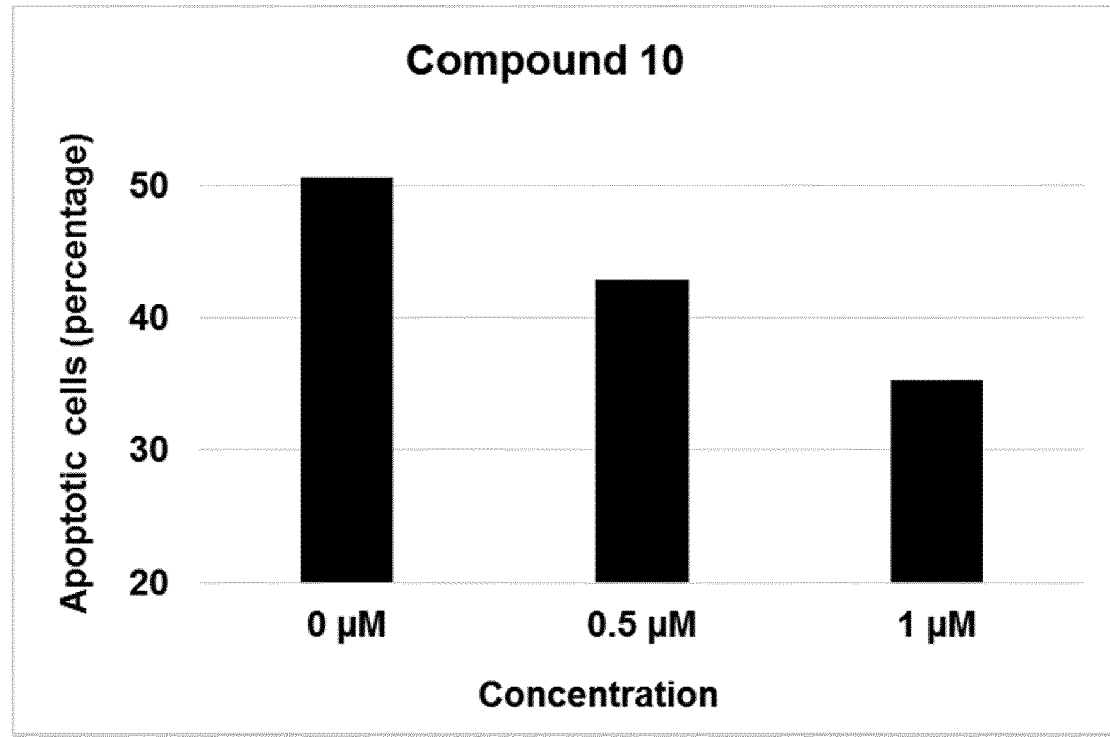

FIG. 10 shows the ability of compound 10 to protect neonatal rat cardiomyocytes against hypoxia-induced apoptosis. The graph shows the percentage of apoptotic cells measured by FACS analysis. Cardiomyocytes were exposed to hypoxia (0.3% $O_2$) for 36 h in the absence (0 μM) or in the presence of indicated concentrations of Compound 2 (n=3).

The present invention is further described with reference to the following non-limiting examples.

EXAMPLES

1-METHODS & MATERIALS 1.1- Preparation of the compounds according to the present invention The reactants and commercials compounds were purchased from Acros Organics, Sigma-Aldrich. The compounds according to the present invention can be prepared according to the following general procedure:
Compounds 1 & 2: preparation of 2-(2-chlorobenzyl)-N'-(3-methylbutoxy)hydrazinecarboximidamide formate salt (compound 1) and 2-(2-chlorobenzyl)-N'-(3-methylbutoxy)hydrazinecarboximidamide (compound 2)
2-(3-methylbutoxy)-1H-isoindole-1,3(2H)-dione (1-1)

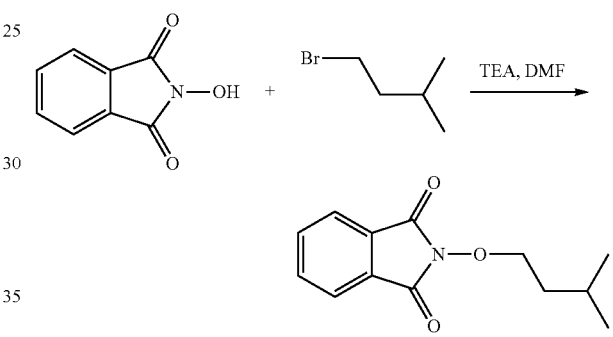

Triethylamine (49.58 g) was added drop wise to a stirred solution of N-Hydroxyphthalimide (40 g) and 1-bromo-3-methyl butane (37.4 g) in DMF (600 ml) at room temperature. The reaction mixture was stirred at 70° C. for 18 hours. The reaction mixture was allowed to cool to room temperature. The mixture was concentrated under reduced pressure and the residue thus obtained was suspended in cold water (1000 ml). The resulting suspension was stirred well for some time and the solid was filtered off under reduced pressure. The solid was further washed with demineralized water (200 ml) and hexane (100 ml). The resulting solid was dried under reduced pressure to get a crude material which was purified by column chromatography using silica gel. The desired product eluted at around 2% Methanol in dichloromethane. Evaporation of pure product fractions gave 50.0 g of 2-(3-methylbutoxy)-1H-isoindole-1,3(2H)-dione (Yield: 87.4%). $^1$H-NMR (DMSO-d6): δ(ppm) 0.93 (d, 6H), 1.57 (q, 2H), 1.82 (m, 1H), 4.16 (t, 2H), 7.86 (s, 4H); LC-MS: m/z=234.25 (M+H).
1-(amino-oxy)-3-methylbutane hydrochloride (I-2)

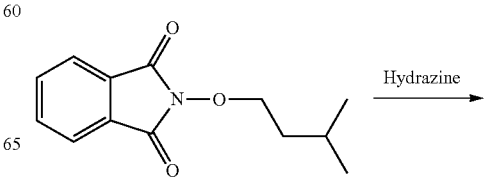

-continued

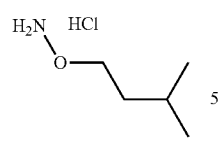

Hydrazine hydrate (12.8 g) was added drop-wise to a stirred solution of 2-(3-methylbutoxy)-1H-isoindole-1,3 (2H)-dione (45 g) in methanol (600 ml) at room temperature. The reaction mixture was stirred at the same temperature for 24 hours. The reaction mixture was filtered off to remove the insoluble by-product and the resulting filtrate was concentrated under reduced pressure to get a crude material which was purified by column chromatography using silica gel. The desired product eluted at around 1% Methanol in dichloromethane. Evaporation of pure product fractions gave the desired intermediate as free base which was converted as hydrochloride salt using 4M HCl in 1,4-dioxane, to get 3.3 g of 1-(aminooxy)-3-methylbutane hydrochloride. $^1$H-NMR (DMSO-d6): δ(ppm) 0.89 (d, 6H), 1.46 (q, 2H), 1.65 (m, 1H), 4.01 (t, 2H), 10.84 (s, 3H).

N'-(3-methylbutoxy)hydrazinecarboximidamide (1-3)

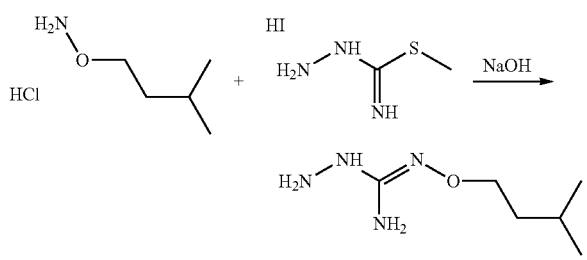

2N NaOH solution (3.6 ml) was added drop wise to a stirred solution of 1-(amino-oxy)-3-methylbutane hydrochloride (1.2 g) and s-methylisothiosemicarbazide hydroiodide (2.02 g) in water (3.6 ml) at room temperature and was stirred for 48 hours. Then, the reaction mixtures was concentrated under reduced pressure and the residue was azeotroped with methanol (5 ml). The resulting residue was suspended in ethanol (10 ml) and insoluble inorganic salts were removed by filtration. The filtrate was directly used for the next step without any further processing. N'-(3-methylbutoxy)hydrazinecarboximidamide was confirmed by LCMS analysis. LC-MS: m/z=161.5 (M+H).

2-(2-chlorobenzyl)-N'-(3-methylbutoxy)hydrazinecarboximidamide formate salt (compound 1)

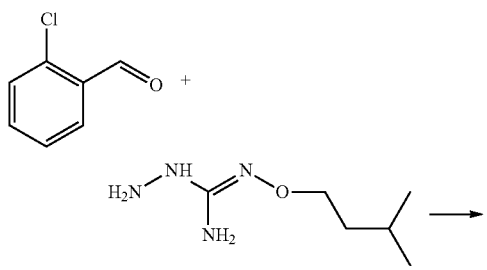

-continued

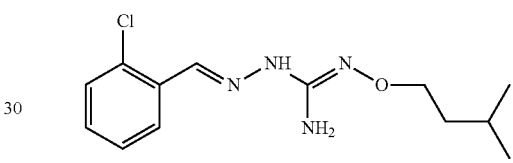

2-chlorobenzaldehyde (1.81 g) was added drop wise to the filtrate which contain N'-(3-methylbutoxy)hydrazinecarboximidamide at room temperature and was stirred for 2 hours. Then, the reaction mixture was concentrated under reduced pressure and the residue thus obtained was further purified by Prep HPLC using 0.1% HCOOH/water/MeCN to give 0.27 g of 2-(2-chlorobenzyl)-N'-(3-methylbutoxy)hydrazinecarboximidamide as formate salt (Yield: 13.1%) $^1$H-NMR (DMSO-d6): δ (ppm) 0.88 (d, 6 H), 1.48 (q, 2H), 1.68 (m, 1H), 3.75 (t, 2H), 7.32 (m, 2 H), 7.44 (m, 2 H), 8,10 (m, 1 H), 8.14 (m, 1H), 8.25 (m, 1H), 11.80 (s broad, 2H). LC-MS: m/z=282.88 (M+H).

2-(2-chlorobenzyl)-N'-(3-methylbutoxy)hydrazinecarboximidamide (compound 2)

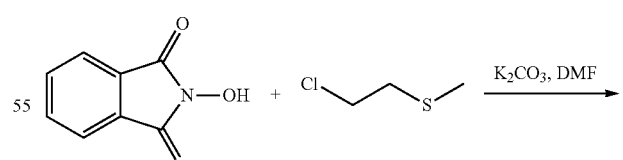

2-(2-chlorobenzyl)-N'-(3-methylbutoxy)hydrazinecarboximidamide formate salt (220 mg) was dissolved in water and was basified by saturated NaHCO$_3$ aqueous solution. The basic aqueous solution was extracted with Dichloromethane and the organic layer was washed with water, dried over sodium sulphate and evaporated under reduced pressure to give 180 mg of 2-(2-chlorobenzyl)-N'-(3-methylbutoxy)hydrazinecarboximidamide as free base (Yield: 95%). $^1$H-NMR (DMSO-d6): δ (ppm) 0.89 (d, 6H), 1.49 (q, 2H), 1.69 (m, 1H), 3.75 (t, 2H), 5.73 (s broad, 2H), 7.30 (m, 2H), 7.44 (m, 1H), 8,11 (m, 1H), 8.15 (m, 1H), 10.48 (s broad, 1H). LC-MS: m/z=282.82 (M+H).

Compound 3: Preparation of 2-(2-chlorobenzylidene)-N'-[2-(methylsulfonyOethoxy]hydrazinecarboximidamide 2[2-(methylsulfanyl)ethoxy]-1H-isoindole-1,3(2H)-dione (1-4)

2-chloroethyl methyl sulfide (10.1 g) was added dropwise to a stirred solution of N-Hydroxyphthalimide (12.5 g), potassium iodide (2.5 g) and potassium carbonate (21.1 g) in DMF (150 ml) at room temperature and was stirred at the 80° C. for 18 hours. The reaction mixture was allowed to cool to room temperature and was dumped in 500 ml of cold water. Then, the solid thus obtained was filtered off under reduced pressure. The resulting solid was dried under reduced pressure to give 9.7 g of 2-[2-(methylsulfanyl) ethoxy]-1 H-isoindole-1,3(2H)-dione (Yield: 52.8%) and was used for the next step without any further processing. $^1$H-NMR (DMSO-d6): δ (ppm) 2.16 (s, 3 H), 2.84 (t, 2H), 4.29 (t, 2H), 7.87 (s, 4H). LC-MS: m/z=238.4 (M+H).
2[2-(methylsulfonyl)ethoxy]-1H-isoindole-1,3(2H)-dione (1-5)

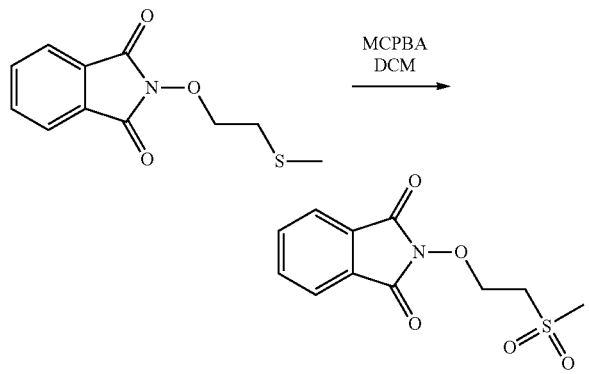

m-CPBA (11 g) was added portion wise to a stirred solution of 2-[2-(methylsulfanyl)ethoxy]-1H-isoindole-1,3 (2H)-dione (9.6 g) in dichloromethane (100 ml) at room temperature and was stirred at room temperature for 6 hours. The crude was concentrated under reduced pressure and the resulting residue was suspended in saturated NaHCO$_3$ solution (100 ml) and stirred for 30 minutes. The resulting solid was filtered off under reduced pressure and washed with water (50 ml) and was dried under reduced pressure to give 9.0 g of 2[2-(methylsulfonyl)ethoxy]-1H-isoindole-1,3(2H)-dione (Yield: 82.6%) and was used for the next step without any further processing. $^1$H-NMR (DMSO-d6): δ (ppm) 3.15 (s, 3 H), 3.66 (t, 2H), 4.54 (t, 2H), 7.88 (s, 4 H). LC-MS: m/z=270.3 (M+H).
1-(aminooxy)-2-(methylsulfonyl)ethane hydrochloride (1-6)

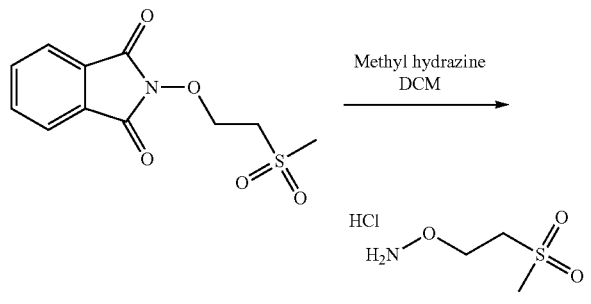

85% methyl hydrazine (2.0 g) was added drop wise to a stirred suspension of 2[2-(methylsulfonyl)ethoxy]-1H-isoindole-1,3(2H)-dione (9.0 g) in dichloromethane (100 ml) at room temperature and was stirred for 6 hours. Then the reaction mixture was filtered off under reduced pressure to remove insoluble by-product. The resulting filtrate was concentrated under reduced pressure at lower temperature. The residue was suspended in 1N HCl (100 ml) and extracted by ethyl acetate (3×250 ml). The resulting aqueous solution containing the desired product was concentrated under reduced pressure to give white solid which was further triturated with diethyl ether and dried under reduced pressure to give 4.0 g of 1-(aminooxy)-2-(methylsulfonyl)ethane hydrochloride (Yield: 68.3%). $^1$H-NMR (DMSO-d6): δ (ppm) 3.04 (s, 3H), 3.60 (t, 2H), 4.38 (t, 2H), 10.09 (s broad, 2H). LC-MS: m/z=270.3 (M+H).
N'-[2-(methylsulfonyl)ethoxy]hydrazinecarboximidamide (1-7)

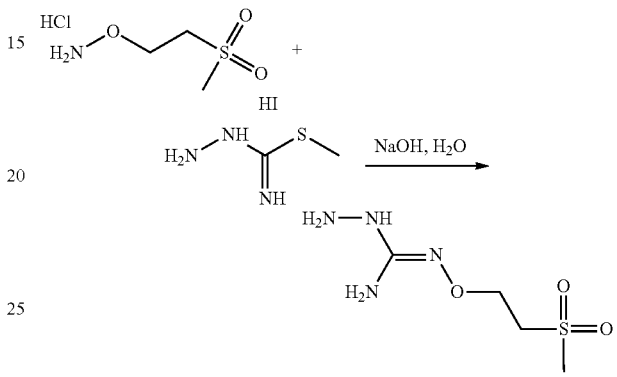

2N NaOH solution (4.28 ml) was added drop wise to a stirred solution of 1-(aminooxy)-2-(methylsulfonyl)ethane hydrochloride (1.5 g) and s-methylisothiosemicarbazide hydroiodide (1.99 g) in water (4.5 ml) at room temperature and was stirred for 48 hours. Then, the reaction mixture was concentrated under reduced pressure and the residue was azeotroped with methanol (5 ml). The resulting material was suspended in ethanol (10 ml) and insoluble inorganic salts were removed by filtration. The resulting filtrate which contain N'-[2-(methylsulfonyl)ethoxy]hydrazinecarboximidamide was directly used for the next step without any further processing.
2-(2-chlorobenzylidene)-N'-[2-(methylsulfonyl)ethoxy]hydrazinecarboximidamide (Compound 3)

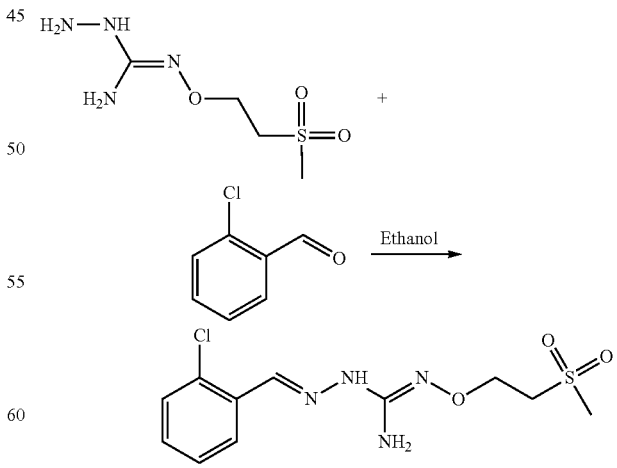

2-chlorobenzaldehyde (1.32 g) was added drop wise to the filtrate containing N'-[2-(methylsulfonyl)ethoxy]hydrazinecarboximidamide at room temperature. The mixture was stirred at room temperature for 2 hours. The reaction mixture was concentrated under reduced pressure and the residue thus obtained was further purified by Prep HPLC using 0.1% NH$_3$/water/MeCN to give 20 mg of 2-(2-chlorobenzylidene)-N'-[2-(methylsulfonyl)ethoxy]hydrazinecarboximidamide (Yield: 0.7% for 2 steps). $^1$H-NMR (DMSO-d6): δ (ppm) 3.03 (s, 3 H), 3.45 (m, 2H), 4.12 (m, 2H), 6.11 (s broad, 2H), 7.40 (m, 2H), 7.44 (m, 1 H), 8.15 (m, 1 H), 8.26 (s broad, 1 H), 10.48 (s, 1 H). LC-MS: m/z=318.83 (M+H).

Compound 4: 2-(2-chlorobenzylidene)-N'-(methylsulfony0propoxylhydrazinecarboximidamide 2[3-(methylsulfanyl)propoxy]-1H-isoindole-1,3(2I-1)-dione (1-8)

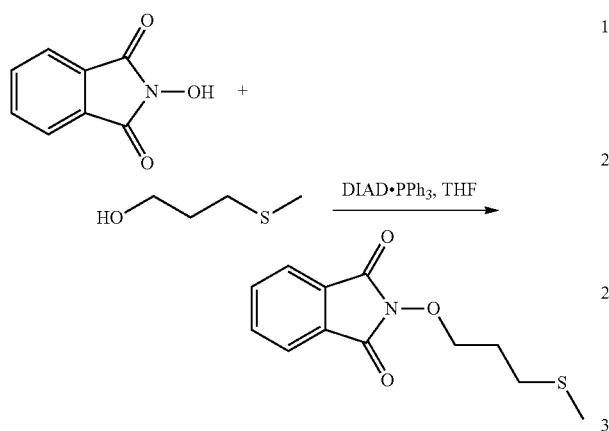

Diisopropyl azodicarboxylate (77.92 ml) was added drop wise to a stirred solution of N-Hydroxyphthalimide (36.8 g), 3-(methylsulfanyl)-1-propanol (30 g) and triphenylphosphine (37.1 g) in anhydrous THF (600 ml) under nitrogen atmosphere at 0° C. The reaction mixture was stirred at 0° C. for 30 minutes and then it was allowed to warm to room temperature and was stirred for 18 hours. Then, the reaction mixture was concentrated under reduced pressure to get a crude material which was purified by column chromatography using silica gel. The desired product eluted at 4% ethyl acetate in hexane. Evaporation of pure product fractions gave 30 g of 2[3-(methylsulfanyl)propoxy]-1H-isoindole-1, 3(2H)-dione (Yield: 42.2%). $^1$H-NMR (DMSO-d6): δ (ppm) 1.94 (q, 2H), 2.07 (s, 3H), 2.67 (t, 2H), 4.23 (t, 2H), 7.87 (s, 4H). LC-MS: m/z=252.4 (M+H).

2[3-(methylsulfonyl)propoxy]-1H-isoindole-1,3(2H)-dione (I-9)

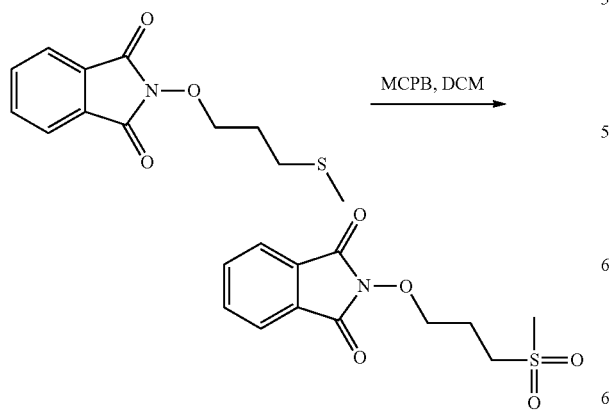

m-CPBA (61.89 g) was added portion wise to a stirred solution of 2-[3-(methylsulfanyl)propoxy]-1H-isoindole-1,3 (2H)-dione (30.0 g) in dichloromethane (550 ml) at room temperature. The mixture was stirred at the room temperature for 5 hours. Then, the reaction mixtures was concentrated under reduced pressure to get a crude material which was suspended in saturated NaHCO$_3$ solution (250 ml) and stirred well for 30 minutes. The resulting solid was filtered off under reduced pressure and washed with water (100 ml). The solid was dried under reduced pressure to give 22 g of 2[3-(methylsulfonyl)propoxy]-1H-isoindole-1,3(2H)-dione (yield: 65%). $^1$H-NMR (CDCl3): δ (ppm) 2.32 (m, 2H), 3.00 (s, 3H), 3.50 (t, 2H), 4.39 (t, 2H), 7.83 (m, 4H). LC-MS: m/z=283.9 (M+H).

1-(aminooxy)-3-(methylsulfonyl)propane hydrochloride (1-10)

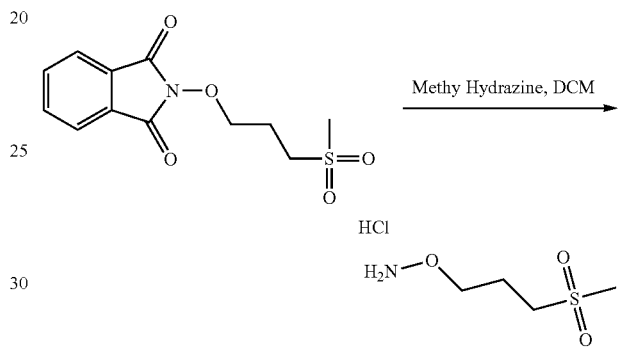

85% methyl hydrazine (4.2 g) was added drop wise to a stirred suspension of 2-[3-(methylsulfonyl)propoxy]-1H-isoindole-1,3(2H)-dione (20 g) in dichloromethane (300 ml) at room temperature and was stirred for 6 hours. Then, the solution was filtered off under reduced pressure to remove the insoluble by-product. The resulting filtrate was concentrated under reduced pressure at low temperature. The residue was suspended in 1N HCl (200 ml) and extracted by ethyl acetate (3×500 ml) to remove undesired impurities. The resulting aqueous solution was concentrated under reduced pressure to give a white solid which was further triturated with diethyl ether and dried under reduced pressure to give 8.0 g of 1-(aminooxy)-3-(methylsulfonyl)propane hydrochloride (Yield: 59.8%). $^1$H-NMR (DMSO-d6): δ (ppm) 2.04 (m, 2H), 3.02 (s, 3H), 3.19 (t, 2H), 4.12 (t, 2H), 11.06 (s broad, 3H).

N'-[3-(methylsulfonyl)propoxy]hydrazinecarboximidamide (I-11)

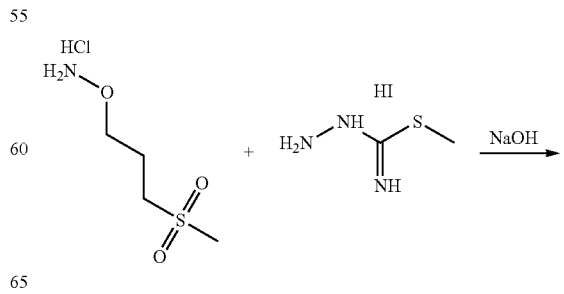

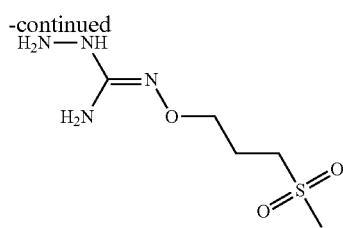

2N NaOH solution (5.28 ml) was added drop wise to a stirred solution of 1-(aminooxy)-3-(methylsulfonyl)propane hydrochloride (2.0 g) and s-methylisothiosemicarbazide hydroiodide (2.46 g) in water (6.0 ml) at room temperature. The reaction mixture was stirred at the room temperature for 24 hours. Formation of N'-[3-(methylsulfonyl)propoxy]hydrazinecarboximidamide was confirmed by LCMS analysis. Then, the mixture was concentrated under reduced pressure and the residue was azeotroped with methanol (15 ml). The resulting material was suspended in ethanol (15 ml) and the insoluble inorganic salts were removed by filtration. The filtrate was directly used for the next step without any further processing. LC-MS: m/z=210.8 (M+H).

2-(2-chlorobenzylidene)-N'-[3-(methylsulfonyl)propoxy]hydrazinecarboximidamide (compound 4)

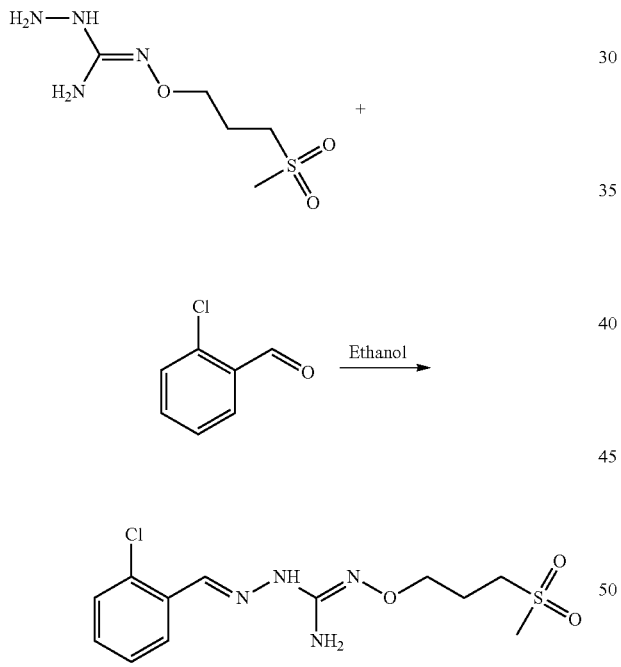

2-chlorobenzaldehyde (1.62 g) was added drop wise to the filtrate containing N'-[3-(methylsulfonyl)propoxy]hydrazinecarboximidamide at room temperature. The resulting reaction mixture was stirred at the same temperature for 2 hours. The crude was concentrated under reduced pressure and the residue thus obtained was further purified by Prep HPLC using 0.1% NH$_3$/water/MeCN. After purification, the material was stirred in saturated NaHCO$_3$ solution and the resulting solid was filtered off under reduced pressure and washed with water and dried to give 0.14 g of pure 2-(2-chlorobenzylidene)-N'-[3-(methylsulfonyl)propoxy]hydrazinecarboximidamide (Yield: 4% for 2 steps). $^1$H-NMR (DMSO-d6): δ (ppm) 2.01 (m, 2H), 2.98 (s, 3H), 3.24 (t, 2H), 3.82 (t, 2H), 5.90 (s, 2H), 7.31 (m, 2H), 7.43 (d, 1H), 8.13 (m, 2H), 10.48 (s, 1H). LC-MS: m/z=333.5 (M+H).

Compound 5: 2-(2-chlorobenzylidene)-N'-(prop-2-en-1-yloxy) hydrazine carboximidamide N'-(prop-2-en-1-yloxy)hydrazinecarboximidamide (I-12)

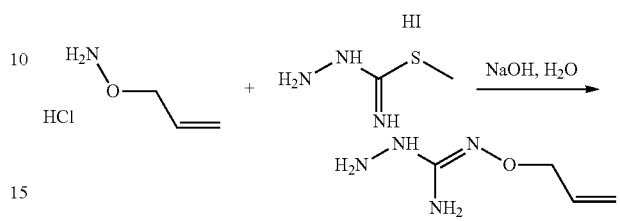

2N NaOH solution (6.8 ml) was added drop wise to a stirred solution of 0-Allylhydroxylamine hydrochloride (1.5 g) and s-methylisothiosemicarbazide hydroiodide (3.22 g) in water (4.2 ml) at room temperature. The reaction mixture was stirred at room temperature for 48 hours. Formation of intermediate I-12 N'-(prop-2-en-1-yloxy)hydrazinecarboximidamide was confirmed by LCMS analysis. Then, the mixture was concentrated under reduced pressure and the residue was azeotroped with methanol (5 ml). The resulting material was suspended in ethanol (10 ml) and the insoluble inorganic salts were removed by filtration. The filtrate was directly used for the next step without any further processing. LC-MS: m/z=130.6 (M+H).

2-(2-chlorobenzylidene)-N'-(prop-2-en-1-yloxy)hydrazinecarboximidamide (Compound 5)

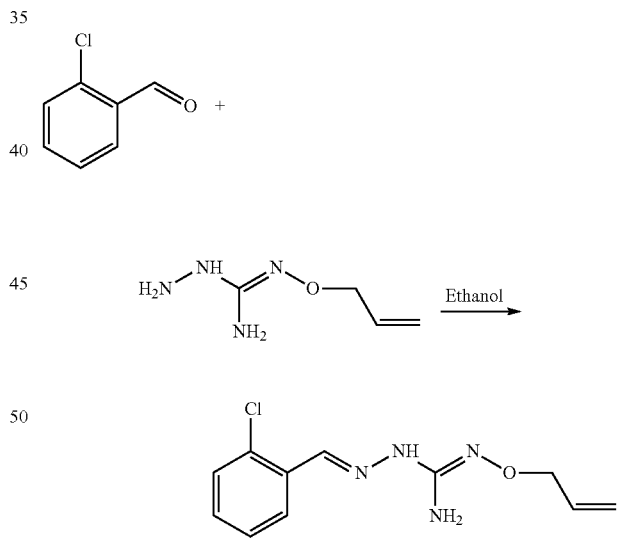

2-chlorobenzaldehyde (1.9 g) was added drop wise to the filtrate containing N'-(prop-2-en-1-yloxy)hydrazinecarboximidamide at room temperature and was stirred for 2 hours. The reaction mixture was concentrated under reduced pressure and the residue thus obtained was further purified by Prep HPLC using 0.1% HCOOH/water/MeCN to give 0.25 g of 2-(2-chlorobenzylidene)-N'-(prop-2-en-1-yloxy)hydrazinecarboximidamide (Yield: 6.1% for 2 steps. $^1$H-NMR (DMSO-d6): δ (ppm) 3.17 (s, 1H), 4.23 (m, 2H), 5.82 (s broad, 2H), 5.98 (m, 1H), 7.37 (m, 2H), 8.15 (m, 3H). LC-MS: m/z=252.8 (M+H).

Compound 6: 2-(2-chlorobenzylidene)-N'-(2-hydroxyethoxy) hydrazine carboximidamide 2-(2-hydroxyethoxy)-1H-isoindole-1,3(2H)-dione (1-13)

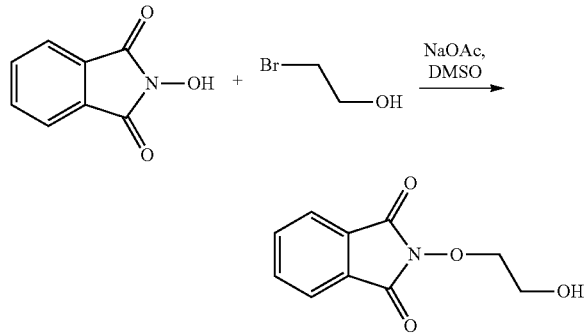

2-Bromotehanol (13.26 ml) was added drop wise to a stirred solution of N-Hydroxyphthalimide (10.0 g) and Sodium acetate (25.14 g) in DMF (50 ml) at room temperature. The resulting reaction mixture was stirred at 80° C. for 1.5 hours. The reaction mixture was allowed to cool to room temperature and was dumped in 500 ml of cold water and the product was extracted by ethyl acetate (2×400 ml). The resulting organic layer were combined and distilled under vacuum. The residue was stirred in cold water and the resulting solid was filtered off under vacuum. The solid was dried under reduced pressure to give 6.0 g of 2-(2-hydroxyethoxy)-1H-isoindole-1,3(2H)-dione (Yield: 47.3%) which were used for the next step without any further processing. $^1$H-NMR (DMSO-d6): δ (ppm) 3.70 (q, 2H), 4.18 (t, 2H), 4.83 (t, 1H), 7.87 (s, 4H). LC-MS: m/z=208.34 (M+H).

2-(aminooxy)ethanol hydrochloride (1-14)

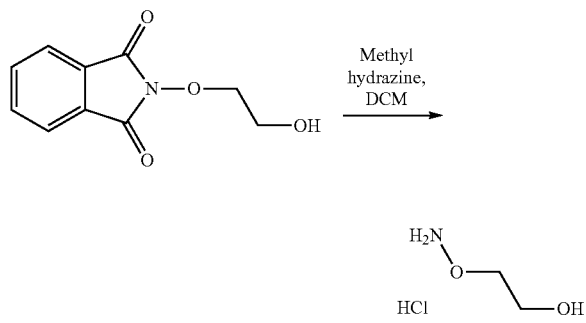

85% methyl hydrazine (1.25 g) was added drop wise to a stirred suspension of 2-(2-hydroxyethoxy)-1H-isoindole-1,3(2H)-dione (6.0 g) in dichloromethane (25 ml) at room temperature and was stirred for 2 hours. Then, the reaction mixture was filtered off under reduced pressure to remove insoluble by-product. The filtrate was concentrated under reduced pressure at lower temperature. The residue was suspended in 2N HCl in Ethylacetate (20 ml) and concentrated under reduced pressure at lower temperature. The resulting solid was triturated with Dichloromethane (2×15 ml) and dried under reduced pressure to give 2.8 g of 2-(aminooxy)ethanol hydrochloride (Yield: 85.5% as mono hydrochloride salt). $^1$H-NMR (DMSO-d6): δ (ppm) 3.61 (m, 2H), 4.04 (t, 2H), 4.73 (m, 1H), 11.02 (s broad, 2H).

N'-(2-hydroxyethoxy)hydrazinecarboximidamide (1-15)

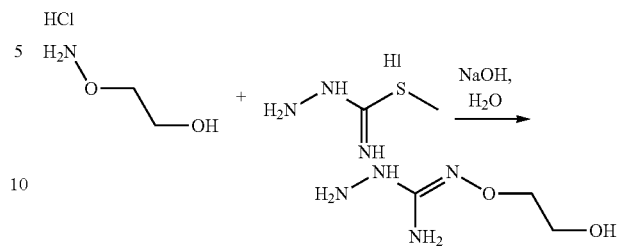

2N NaOH solution (10.6 ml) was added drop wise to a stirred solution of 2-(aminooxy)ethanol hydrochloride salt (2.4 g) and s-methyl isothiosemicarbazide hydroiodide (4.98 g) in water (8.4 ml) at room temperature and was stirred for 24 hours. Formation of N'-(2-hydroxyethoxy)hydrazine carboximidamide was confirmed by LCMS analysis. The mixtures was concentrated under reduced pressure and the resulting residue was azeotroped with methanol (15 ml). The resulting material was suspended in ethanol (10 ml) and the insoluble inorganic salts were removed by filtration. The filtrate containing N'-(2-hydroxyethoxy)hydrazinecarboximidamide was directly used for the next step without any further processing. LC-MS: m/z=134.6 (M+H)

2-(2-chlorobenzylidene)-N'-(2-hydroxyethoxy)hydrazinecarboximidamide (Compound 6)

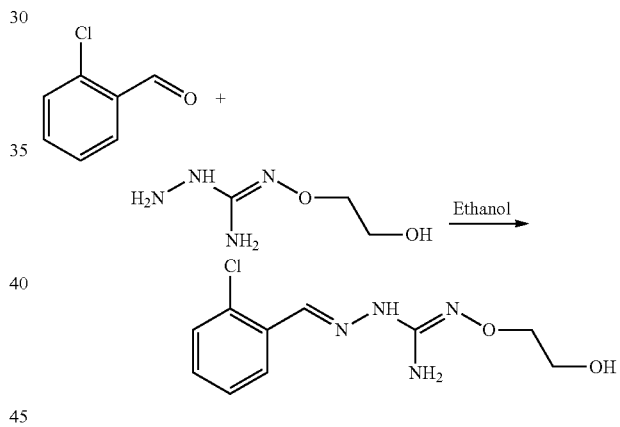

2-chlorobenzaldehyde (3.28 g) was added drop wise to the filtrate containing N'-(2-hydroxyethoxy)hydrazinecarboximidamide at room temperature and was stirred for 2 hours. The reaction mixture was concentrated under reduced pressure and the residue thus obtained was further purified by Prep HPLC using 0.1% NH$_3$/water/MeCN to give 0.24 g of 2-(2-chlorobenzylidene)-N'-(2-hydroxyethoxy)hydrazinecarboximidamide (Yield: 4.4% for 2 steps). $^1$H-NMR (DMSO-d6): δ (ppm) 3.68 (m, 2H), 3.97 (m, 2H), 5.82 (s broad, 2H), 5.07 (m, 1H), 7.50 (m, 2H), 7.55 (m, 1H), 8.34 (m, 1H) 8.47 (s, 1H), 8.67 (s, 1H), 11.78 (m, 1H), 12.09 (m, 1H). LC-MS: m/z=256.73 (M+H).

Compound 7: 2-(2-chlorobenzylidene)-N'-(2-chloroethoxy) hydrazine carboximidamide hydrochloride

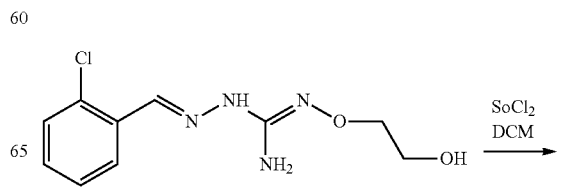

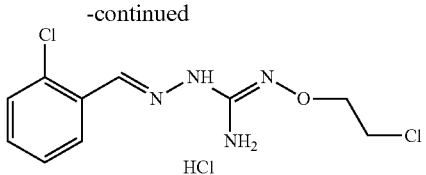

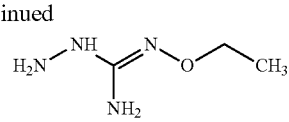

SoCl₂ (0.26 ml) was added drop wise to a stirred solution of 2-(2-chlorobenzylidene)-N'-(2-hydroxyethoxy)hydrazine carboximidamide (0.22 g) in Dichloromethane (10 ml) at 0° C. The reaction mixture was stirred at the room temperature for 24 hours. Then, the reaction mixtures was concentrated under reduced pressure. The resulting residue was triturated with n-pentane (2×5 ml) and dried under reduced pressure to give 0.26 g of 2-(2-chlorobenzylidene)-N'-(2-chloroethoxy) hydrazinecarboximidamide hydrochloride (Yield: 99.5%). LC-MS: m/z=274.8 (M+H).

Compound 8: 2-(2-chlorobenzylidene)-N'-[2-(pyrrolidin-1-yl)ethoxy] hydrazine carboximidamide 1N NaOH solution (5.12 ml) was added drop wise to a stirred solution of ethoxyamine hydrochloride salt (0.5 g) and s-methyl isothiosemicarbazide hydroiodide (1.19 g) in water (5.0 ml) at room temperature and was stirred for 48 hours. Formation of N'-(2-ethoxy)hydrazinecarboximidamide was confirmed by LCMS analysis. The mixtures was concentrated under reduced pressure and the resulting residue was dissolved in ethanol (15 ml). The insoluble solids were removed by filtration. The filtrate was concentrated and N'-(2-ethoxy)hydrazinecarboximidamide was directly used for the next step without any further processing. LC-MS: m/z=118.8 (M+H).

2-(2-chlorobenzylidene)-N'-ethoxyhydrazinecarboximidamide (compound 10)

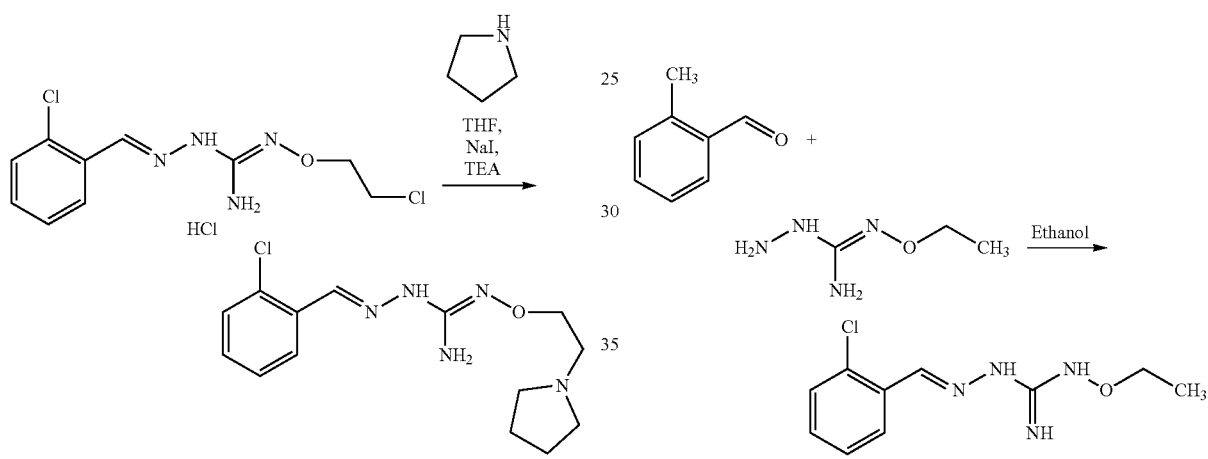

Pyrrolidine (0.23 g) was added to a stirred solution of 2-(2-chlorobenzylidene)-N'-(2-chloroethoxy)hydrazine carboximidamide hydrochloride (0.27 g), Triethylamine (0.35 g) and Sodium iodide (0.04 g) in THF (10 ml) at room temperature. The resulting mixture was stirred at 50° C. for 24 hours. Then, the reaction mixtures was allowed to cool to room temperature and the crude was dumped in 50 ml of cold water. The product was extracted by ethyl acetate (2×50 ml). Then, organic layer were combined and distilled under vacuum, the residue thus obtained was further purified by Prep HPLC using 0.1% NH₃/water/MeCN to give 14 mg of 2-(2-chlorobenzylidene)-N'-[2-(pyrrolidin-1-Aethoxy]hydrazinecarboximidamide (Yield: 5.3%).). ¹H-NMR (MeOD): δ (ppm) 1.91 (m, 4H), 2.75 (m, 4H), 2.88 (t, 2H), 3.97 (t, 2H), 7.32 (m, 2H), 7.41 (m, 1H), 8.07 (m, 1H), 8.32 (s, 1H). LC-MS: m/z=310.33 (M+H).

Compound 10: 2-(2-chlorobenzylidene)-M-ethoxyhydrazinecarboximidamide
N'-(2-ethoxy)hydrazinecarboximidamide (I-16)

2-chlorobenzaldehyde (0.717 g) was added dropwise to N'-(2-ethoxy)hydrazinecarboximidamide in solution in ethanol (10 ml) and sodium acetate (0.42 g) at room temperature and was stirred for 2 hours at 90° C. The reaction mixture was concentrated under reduced pressure and the residue thus obtained was further purified by chromatography to give 21.4 mg of 2-(2-chlorobenzylidene)-N'-(2-ethoxy)hydrazinecarboximidamide (Yield: 1.7% for 2 steps). ¹H-NMR (DMSO-d6): 8 (ppm) 1.18 (t, 3H), 3.77 (q, 2H), 5.77 (s broad, 2H), 7.31 (m, 2H), 7.43 (m, 1H), 8.11 (m, 1H), 8.15 (s, 1H), 10.45 (s broad, 1H). LC-MS: m/z=240.9 (M+H).

Compound 11: 2-(2,6-dichlorobenzylidene)-N-ethoxyhydrazinecarboximidamide

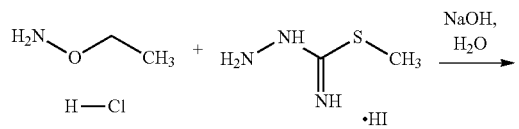

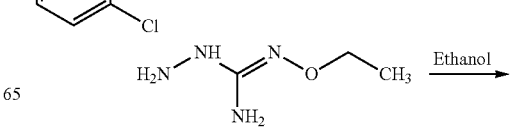

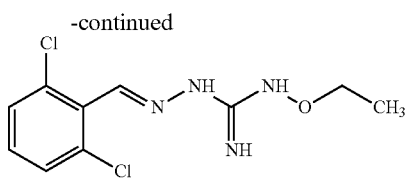

2,6-dichlorobenzaldehyde (0.896 g) was added dropwise to 1 equivalent of N'-(2-ethoxy)hydrazinecarboximidamide (1-16) in solution in ethanol (10 ml) and sodium acetate (0.42 g) at room temperature and was stirred for 2 hours at 90° C. The reaction mixture was concentrated under reduced pressure and the residue thus obtained was further purified by chromatography to give 57 mg of 2-(2,6-dichlorobenzylidene)-N'-(2-ethoxy)hydrazinecarboximidamide (Yield: 4.1% for 2 steps). $^1$H-NMR (DMSO-d6): δ (ppm) 1.77 (t, 3H), 3.78 (q, 2H), 5.48 (s broad, 2H), 7.33 (t, 1H), 7.52 (m, 2H), 8.04 (s, 1H), 8.16 (m, 1H). LC-MS: m/z=277.1 (M+H).

Compound 12: 2-(2-chlorobenzylidene)-N-propoxyhydrazinecarboximidamide

N'-propoxyhydrazinecarboximidamide (I-17)

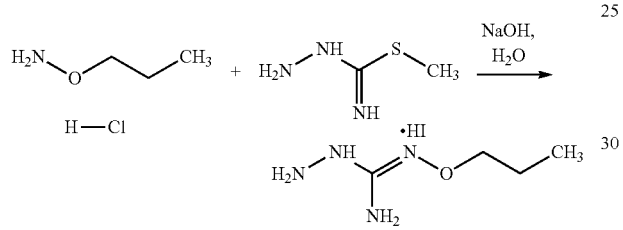

2N NaOH solution (1.23 ml) was added dropwise to a stirred solution of O-propylhydroxylamine hydrochloride salt (0.28 g) and s-methyl isothiosemicarbazide hydroiodide (0.58 g) in water (2.0 ml) at room temperature and was stirred for 24 hours. Formation of N'-(propoxy)hydrazinecarboximidamide was confirmed by LCMS analysis. The mixtures was concentrated under reduced pressure and the resulting residue was dissolved in ethanol (15 ml). The insoluble solids were removed by filtration. The filtrate was concentrated and N'-(propoxy)hydrazinecarboximidamide was directly used for the next step without any further processing. LC-MS: m/z=132.9 (M+H) 2-(2-chlorobenzylidene)-N-propoxyhydrazinecarboximidamide (compound 12)

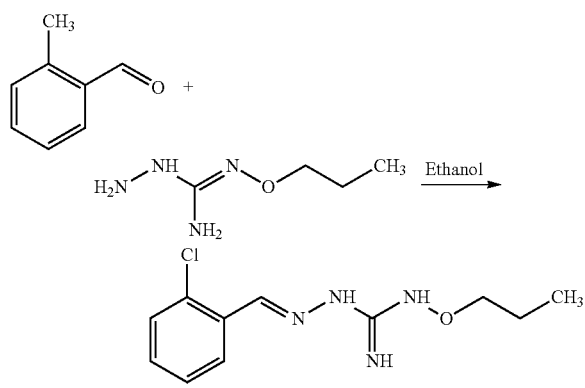

2-chlorobenzaldehyde (0.35 g) was added dropwise to N'-(2-propoxy)hydrazinecarboximidamide in solution in ethanol (10 ml) and was stirred for 2 at room temperature. The reaction mixture was concentrated under reduced pressure and the residue thus obtained was further purified by chromatography to give 25 mg of 2-(2-chlorobenzylidene)-N'-(2-propoxy)hydrazinecarboximidamide (Yield: 3.9% for 2 steps). $^1$H-NMR (DMSO-d6): δ (ppm) 0.88 (t, 3H), 1.58 (m, 2H), 3.66 (t, 2H), 5.75 (s broad, 1H), 7.29 (m, 2H), 7.41 (m, 1H), 8.10 (m, 2H), 10.45 (s broad, 2H). LC-MS: m/z=255.1 (M+H).

Compound 13: 2-(2-chlorobenzylidene)-N-(2-ethoxyethoxy) hydrazinecarboximidamide 2-(2-ethoxyethoxy)-1,3-dimethylidene-2,3-dihydro-1H-isoindole (1-18)

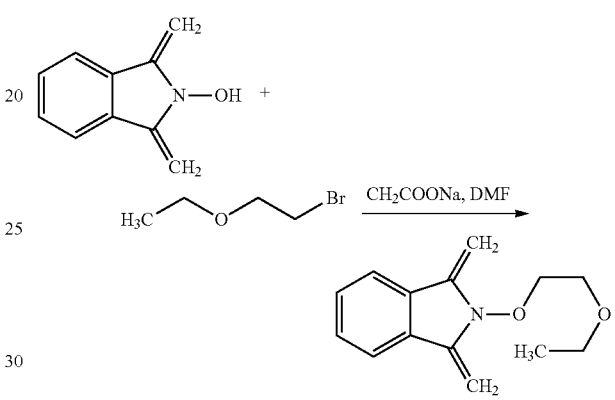

The N-hydroxypthalimide (4.0 g) and 1-bromo-2-ethoxyethane (11.25 g) were dissolved in DMF (40.0 ml) and CH$_3$COONa (10.0 g) was added to the solution at room temperature. The reaction mixture was allowed to stir at 70° C. for 12 hours. The reaction mixture was allowed to cool to room temperature and was and was poured in water and then extracted two times by ethyl acetate. The organic layer was concentrated under reduce pressure and was purified by column chromatography using silica gel. The desired product was eluted with 0-30% ethyl acetate in hexane. Evaporation of pure product fractions gave 4.8 g of 2-(2-ethoxyethoxy)-1,3-dimethylidene-2,3-dihydro-1H-isoindole (1-18) (Yield: 83.3%). $^1$H-NMR (DMSO-d6): δ (ppm) 0.98 (t, 3H),3.39 (q, 2H), 3.73 (t, 2H), 4.27 (t, 2H), 7.87 (s, 4H). LC-MS: m/z=236.2 (M+H).

1-(aminooxy)-2-ethoxyethane hydrochloride (1-19)

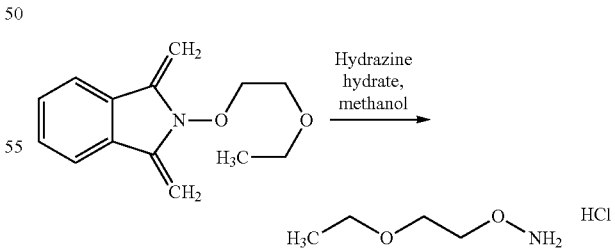

Hydrazine hydrate (1.32 g) was added dropwise to a stirred solution of 2-(2-ethoxyethoxy)-1,3-dimethylidene-2,3-dihydro-1H-isoindole (4.8 g) in methanol (10 ml) at room temperature and was stirred for 30 minutes. Then, the reaction mixture was filtered off under reduced pressure to remove insoluble by-product. The filtrate was concentrated under reduced pressure at lower temperature and triturated ether and insoluble was removed by filtration. Then, to the filtrate, 4N HCl in dioaxane (10.2 ml) was added dropwise and the precipitated salt was collected by filtration and was dried to 2.0 g of 1-(aminooxy)-2-ethoxyethane hydrochloride (Yield: 69.4% as mono hydrochloride salt). $^1$H-NMR (DMSO-d6): δ (ppm) 1.11 (t, 3H), 3.44 (q, 2H), 3.59 (m, 2H), 4.14 (m, 2H), 11.02 (s broad, 2H). LC-MS: m/z=106.1 (M+H).

N'-(2-ethoxyethoxy)hydrazinecarboximidamide (1-20)

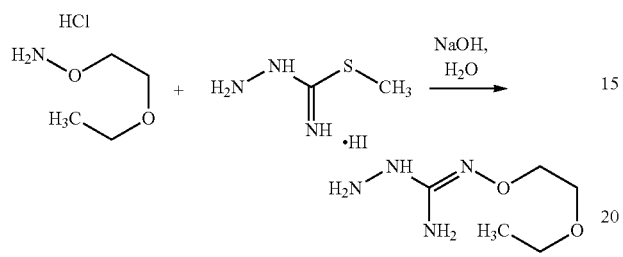

1N NaOH solution (4.23 ml) was added dropwise to a stirred solution of 1-(aminooxy)-2-ethoxyethane hydrochloride salt (0.6 g) and s-methyl isothiosemicarbazide hydroiodide (0.99 g) in water (2.1 ml) at room temperature and was stirred for 48 hours. Formation of N'-(2-ethoxyethoxy)hydrazinecarboximidamide was confirmed by LCMS analysis. The mixtures was concentrated under reduced pressure and the resulting residue was dissolved in ethanol (10 ml). The insoluble solids were removed by filtration. The filtrate was concentrated and N'-(2-ethoxyethoxy)hydrazinecarboximidamide was directly used for the next step without any further processing. LC-MS: m/z=163.0 (M+H).

2-(2-chlorobenzylidene)-N-(2-ethoxyethoxy)hydrazinecarboximidamide (compound 13)

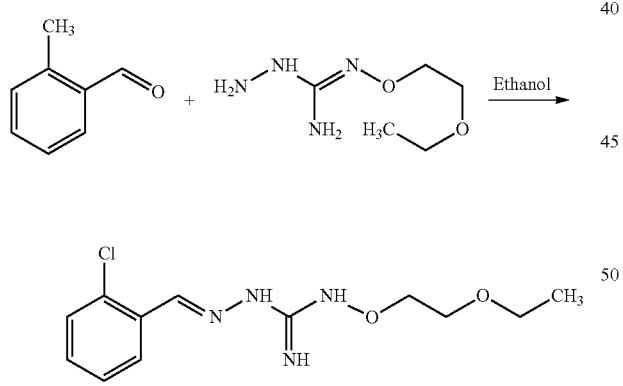

2-chlorobenzaldehyde (0.59 g) was added dropwise to N'-(2-ethoxyethoxy) hydrazinecarboximidamide in solution in ethanol (5 ml) and was stirred for 2 at room temperature. The reaction mixture was concentrated under reduced pressure and the residue thus obtained was further purified by chromatography to give 19 mg of 2-(2-chlorobenzylidene)-N'-(2-propoxy)hydrazinecarboximidamide (Yield: 1.8% for 2 steps). $^1$H-NMR (DMSO-d6): δ (ppm) 1.24 (t, 3H), 3.48 (q, 2H), 3.56 (m, 2H), 3.83 (m, 2H), 5.80 (s broad, 1H), 7.43 (m, 1H), 8.12 (m, 1H), 8.17 (s, 1H), 10.50 (s broad, 2H). LC-MS: m/z=285.0 (M+H).

Compound 14: 2-(2-chlorobenzylidene)-N'-[(3-methylbut-2-en-1-yl)oxy]hydrazinecarboximidamide 2-[(3-methylbut-2-en-1-yl)oxy]-1H-isoindole-1,3(2H)-dione (I-21)

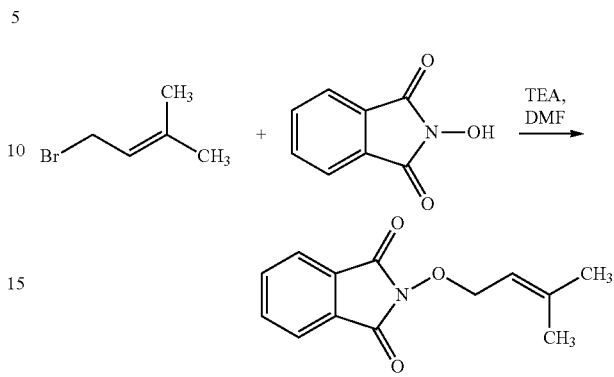

Triethylamine (12.13 g) was added dropwise to a stirred solution of N-Hydroxyphthalimide (9.85 g) and 1-bromo-3-methyl butene (9.0 g) in DMF (30 ml) at room temperature. The reaction mixture was stirred at 70° C. for 2 hours. The reaction mixture was allowed to cool to room temperature. The mixture was concentrated under reduced pressure and the residue thus obtained was suspended in cold water. The resulting suspension was stirred well for some time and the solid was filtered off under reduced pressure. The solid was further washed with demineralized water (200 ml) and hexane (100 ml). The resulting solid was dried under reduced pressure to get a crude material which was purified by column chromatography using silica gel to give 9.0 g of —[(3-methylbut-2-en-1-yl)oxy]-1H-isoindole-1,3(2H)-dione (Yield: 64.5%). $^1$H-NMR (DMSO-d6): δ (ppm) 1.70 (d, 6H), 4.63 (m, 2H), 5.45 (m, 1H), 7.87 (s, 4H). LC-MS: m/z=232.1 (M+H).

1-(aminooxy)-3-methylbut-2-ene hydrochloride (1-22)

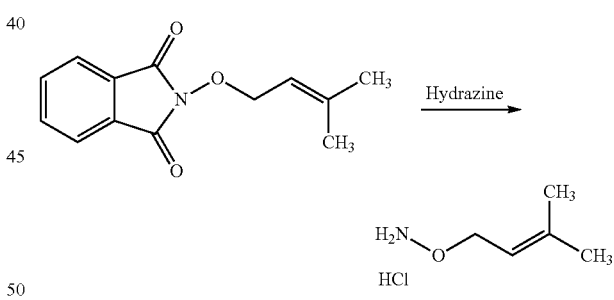

Hydrazine hydrate (2.52 g) was added dropwise to a stirred solution of 2-[(3-methylbut-2-en-1-yl)oxy]-1H-isoindole-1,3(2H)-dione (9.0 g) in methanol (120 ml) at room temperature. The reaction mixture was stirred at the same temperature for 30 min. The reaction mixture was filtered off to remove the insoluble by-product and the resulting filtrate was concentrated under reduced pressure to get a crude material which was purified by column chromatography using silica gel. The crude was triturated with ether and insoluble mass was removed by filtration. The filtrate was treated with 4 M HCl in dioxane (19 ml) dropwise and the precipitate was filtered, collected and dried under vacuum to give 2.9 g of 1-(aminooxy)-3-methylbut-2-ene hydrochloride (Yield: 73.6%). $^1$H-NMR (DMSO-d6): δ (ppm) 1.70 (s, 3H), 1.75 (s, 3H), 1.65 (m, 1H), 4.50 (d, 2H), 5.30 (t, 1H), 10.89 (s, 3H).

N'-[(3-methylbut-2-en-1-yl)oxy]hydrazinecarboximidamide (1-23)

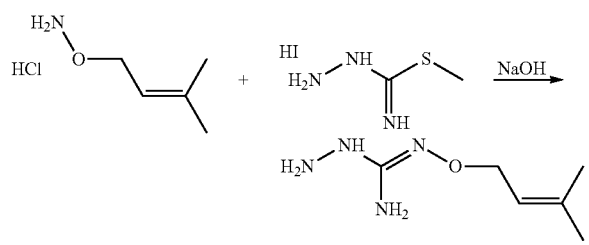

1N NaOH solution (3.63 ml) was added dropwise to a stirred solution of 1-(aminooxy)-3-methylbut-2-ene hydrochloride (0.5 g) and s-methylisothiosemicarbazide hydroiodide (0.85 g) in water (3 ml) at room temperature and was stirred for 48 hours. Then, the reaction mixtures was concentrated under reduced pressure. The resulting residue was suspended in ethanol (15 ml) and insoluble inorganic salts were removed by filtration. The filtrate was concentrated and directly used for the next step without any further processing. N'-[(3-methylbut-2-en-1-yl)oxy] hydrazinecarboximidamide was confirmed by LCMS analysis. LC-MS: m/z=159.15 (M+H).

2-(2-chlorobenzylidene)-N'-[(3-methylbut-2-en-1-yl)oxy] hydrazinecarboximidamide (compound 14)

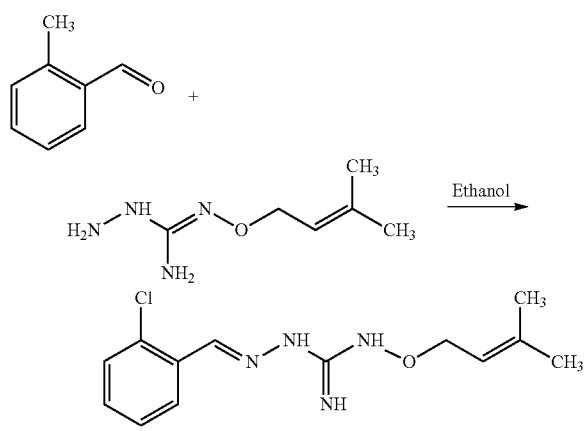

2-chlorobenzaldehyde (0.5 g) was added dropwise to N'-[(3-methylbut-2-en-1-yl)oxy]hydrazinecarboximidamide in solution in ethanol (3 ml) at room temperature and was stirred for 2 hours at 90° C. The reaction mixture was concentrated under reduced pressure and the residue thus obtained was further purified by chromatography to give 139 mg of 2-(2-chlorobenzylidene)-N'-[(3-methylbut-2-en-1-yl)oxy]hydrazinecarboximidamide (Yield: 13.5% for 2 steps). $^1$H-NMR (DMSO-d6): δ (ppm) 1.64 (s, 3H), 1.71 (s, 3H), 3.17 (s, 1H), 4.25 (d, 2H), 5.39 (t, 1H), 5.75 (s broad, 2H), 7.32 (m, 1H), 7.43 (m, 1H), 8.10 (m, 1H), 8.15 (m, 1H), 8.17 (s broad, 1H). LC-MS: m/z=281.2 (M+H).

Compound 15: 2-(2-chlorobenzylidene)-N-[2-(ethylsulfanyl) ethoxy]hydrazinecarboximidamide 2-bromoethyl ethyl sulphide (I-24)

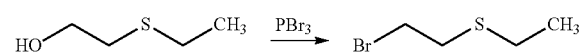

PBr$_3$ (10 ml) was added dropwise to 2-(ethylsulfanyl) ethanol in solution in dichloromethane (100 ml) at 0° C. and was stirred for 2 hours. Then the reaction mixture was warmed to room temperature and stirred for 16 hours. The reaction mixture was cooled at 0° C. and 10 ml of water was added. Then reaction mixture was neutralized with saturated Na$_2$CO$_3$ solution (~up to Ph 7) and extracted with dichloromethane (3×250 ml). The organic layers were separated, combined and dried (Na$_2$SO$_4$) and concentrated to afford 13.0 g of 2-bromoethyl ethyl sulphide (yield: 72.7%). $^1$H-NMR (CDCl$_3$): δ (ppm) 1.30 (t, 3H), 2.62 (q, 2H), 2.97 (m, 2H), 3.50 (m, 2H).

2[2-(ethylsulfanyl)ethoxy]-1H-isoindole-1,3(2H)-dione (I-25)

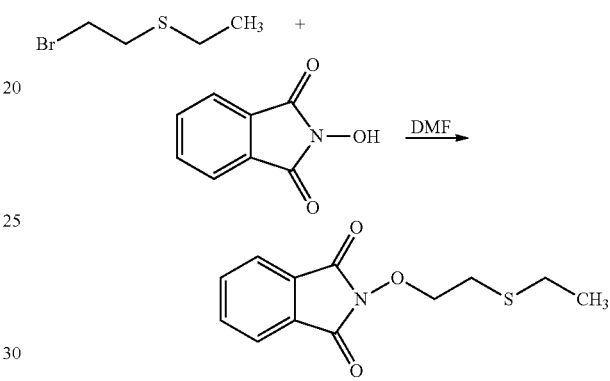

N-hydroxypthalimide (3.9 g) and 2-bromoethyl ethyl sulphide (12.1 g) were dissolved in DMF (40.0 ml) and CH$_3$COONa (9.7 g) was added portionwise to the solution at room temperature. The reaction mixture was allowed to stir at 70° C. for 2 hours. The reaction mixture was allowed to cool to room temperature and was and was poured in cold water and then extracted two times by ethyl acetate. The organic layer was concentrated under reduce pressure and was purified by column chromatography using silica gel. To give 6.0 g of 2-[2-(ethylsulfanyl)ethoxy]-1H-isoindole-1,3 (2H)-dione (1-25) (Yield: 98%). $^1$H-NMR (CDCl$_3$): δ (ppm) 1.29 (t, 3H), 2.63 (q, 2H), 2.94 (t, 2H), 4.36 (t, 2H), 7.77 (m, 2H), 7.86 (m, 2H).

1-(aminooxy)-2-(ethylsulfanyl)ethane hydrochloride (I-26)

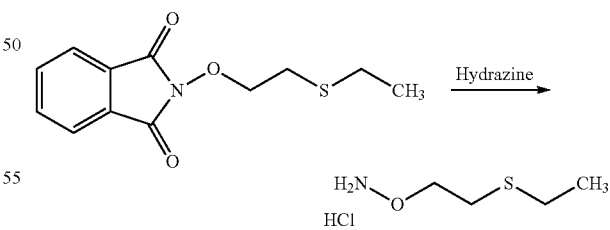

Hydrazine hydrate (0.25 g) was added dropwise to a stirred solution of 2-[2-(ethylsulfanyl)ethoxy]-1H-isoindole-1,3(2H)-dione (1.0 g) in methanol (10 ml) at room temperature. The reaction mixture was stirred at the same temperature for 30 min. The reaction mixture was filtered off to remove the insoluble by-product and the resulting filtrate was concentrated under reduced pressure then dissolved in DCM and insoluble removed by filtration. The filtrate was concentrated under reduced pressure then, the crude was triturated with ether and insoluble mass was removed by filtration. The filtrate was treated with 4 M HCl in dioxane (2 ml) dropwise. Then the solvent was removed by evaporation and the the residue was triturated with diethyl ether to provide 454 mg 1-(aminooxy)-2-(ethylsulfanyl)ethane hydrochloride (Yield: 72.5%). $^1$H-NMR (DMSO-d6): δ (ppm) 1.18 (s, 3H), 2.53 (m, 2H), 2.79 (t, 2H), 4.16 (t, 2H), 11.14 (s broad, 3H).

N'-[2-(ethylsulfanyl)ethoxy]hydrazinecarboximidamide (1-27)

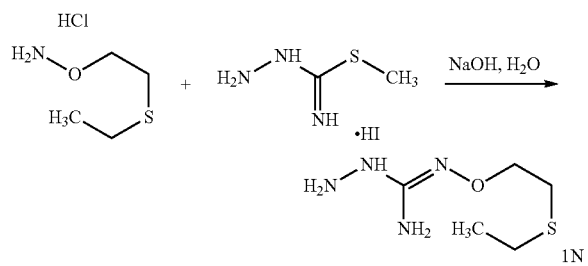

NaOH solution (2.88 ml) was added dropwise to a stirred solution of 1-(aminooxy)-2-(ethylsulfanyl)ethane hydrochloride (0.5 g) and s-methyl isothiosemicarbazide hydroiodide (0.7 g) in water (5 ml) at room temperature and was stirred for 48 hours. The mixtures was concentrated under reduced pressure and the resulting residue was dissolved in ethanol (15 ml). The insoluble solids were removed by filtration. The filtrate was concentrated and N'-[2-(ethylsulfanyl)ethoxy]hydrazinecarboximidamide was directly used for the next step without any further processing.

2-(2-chlorobenzylidene)-N-[2-(ethylsulfanyl)ethoxy]hydrazinecarboximidamide (compound 15)

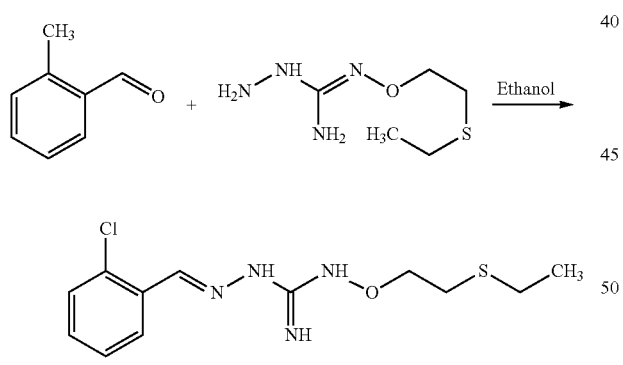

2-chlorobenzaldehyde (0.4 g) was added dropwise to N'-[2-(ethylsulfanyl)ethoxy]hydrazinecarboximidamide in solution in ethanol (5 ml) and was stirred for 2 at room temperature. The reaction mixture was concentrated under reduced pressure and the residue thus obtained was further purified by chromatography to give 15 mg of 2-(2-chlorobenzylidene)-N-[2-(ethylsulfanyl)ethoxy]hydrazinecarboximidamide (Yield: 1.5% for 2 steps). $^1$H-NMR (DMSO-d6): δ (ppm) 1.90 (t, 3H), 2.54 (q, 2H), 2.75 (t, 2H), 3.85 (t, 2H), 5.84 (s broad, 2H), 7.30 (m, 2H), 7.44 (m, 1H), 8.12 (m, 1H), 8.16 (s, 1H), 10.50 (s broad, 1H). LC-MS: m/z=301.9 (M+H).

Compound 16: 2-[(3-chloropyridin-4-yl)methylidene]-N-ethoxyhydrazinecarboximidamide

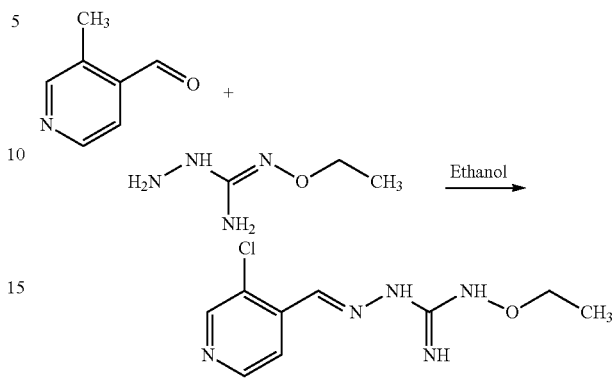

3-chloroisonicotinaldehyde (0.72 g) was added dropwise to 1 equivalent of N'-(2-ethoxy)hydrazinecarboximidamide (I-16) in solution in ethanol (5 ml) and sodium acetate (0.42 g) at room temperature and was stirred for 2 hours at 80° C. The reaction mixture was concentrated under reduced pressure and the residue thus obtained was further purified by chromatography to give 184 mg of 2-[(3-chloropyridin-4-yl)methylidene]-N-ethoxyhydrazinecarboximidamide (Yield: 15% for 2 steps). $^1$H-NMR (DMSO-d6): δ (ppm) 1.19 (t, 3H), 3.79 (q, 2H), 5.96 (s broad, 2H), 8.05 (s, 1H), 8.11 (d, 1H), 8.41 (s, 1H), 10.89 (s broad, 1H). LC-MS: m/z=242.0 (M+H).

Compound 17: 2-(2-chloro-6-fluorobenzylidene)-N-ethoxyhydrazinecarboximidamide

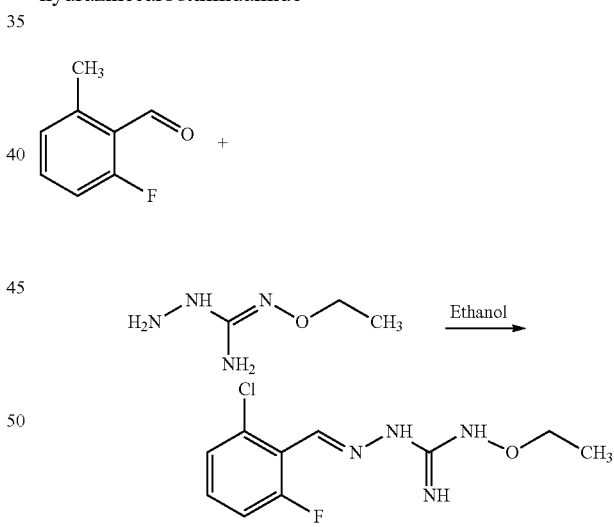

2-chloro-6-flurobenzaldehyde (0.81 g) was added dropwise to 1 equivalent of N'-(2-ethoxy)hydrazinecarboximidamide (I-16) in solution in ethanol (5 ml) and sodium acetate (0.42 g) at room temperature and was stirred for 2 hours at 80° C. The reaction mixture was concentrated under reduced pressure and the residue thus obtained was further purified by chromatography to give 215 mg of 2-(2-chloro-6-fluorobenzylidene)-N-ethoxyhydrazinecarboximidamide (Yield: 17.2% for 2 steps). $^1$H-NMR (DMSO-d6): δ (ppm) 1.17 (m, 3H), 3.78 (q, 2H), 5.48 (s broad, 2H), 7.30 (m, 3H), 8.01 (s, 1H), 10.54 (s broad, 1H). LC-MS: m/z=258.9 (M+H).

Compound 18: N'-butoxy-2-(2-chlorobenzylidene)hydrazinecarboximidamide

Compound 18 is prepared following the same procedure than compound 12 from 2-chlorobenzaldehyde and N'-(2-butoxy)hydrazinecarboximidamide.

Compound 19: 2-(2-chloro-6-fluorobenzylidene)-N'-propoxyhydrazinecarboximidamide

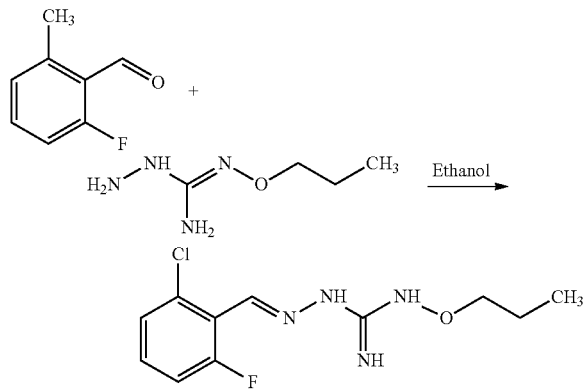

Compound 19 is prepared following the same procedure than compound 17 from 2-chloro-6-flurobenzaldehyde and N'-(2-propoxy)hydrazine carboximidamide (1-17) to give 2-(2-chloro-6-fluorobenzylidene)-N'-propoxyhydrazinecarboximidamide LC-MS: m/z=273.0 (M+H).

Compound 20: 2-(2-chloro-6-fluorobenzylidene)-N'-butoxyhydrazinecarboximidamide

Compound 20 is prepared following the same procedure than compound 17 from 2-chloro-6-flurobenzaldehyde and N'-(2-butoxy)hydrazinecarboximidamide.

Compound 21: 2-(2,6-dichlorobenzylidene)-N-propoxyhydrazinecarboximidamide

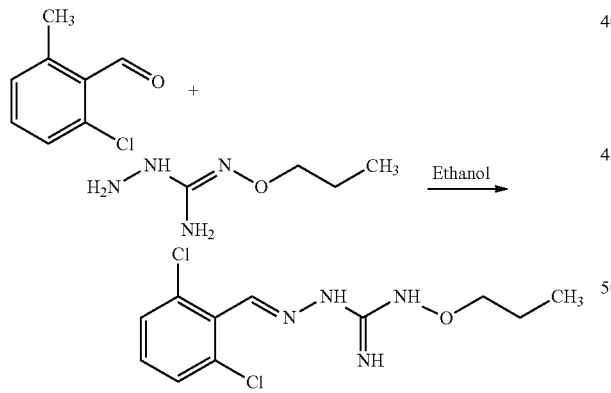

Compound 21 is prepared following the same procedure than compound 11 from 2,6-dichlorobenzaldehyde and N'-(2-propoxy)hydrazinecarboximidamide (I-17) to give 2-(2-chloro-6-fluorobenzylidene)-N'-propoxyhydrazinecarboximidamide LC-MS: m/z=290.9 (M+H).

Compound 22: 2-(2,6-dichlorobenzylidene)-N-butoxyhydrazinecarboximidamide

Compound 22 is prepared following the same procedure than compound 17 from 2,6-dichlorobenzaldehyde and N'-(2-butoxy)hydrazinecarboximidamide.

Compound 23: 2-[(3-chloropyridin-4-yl)methylidene]-N-propoxyhydrazinecarboximidamide

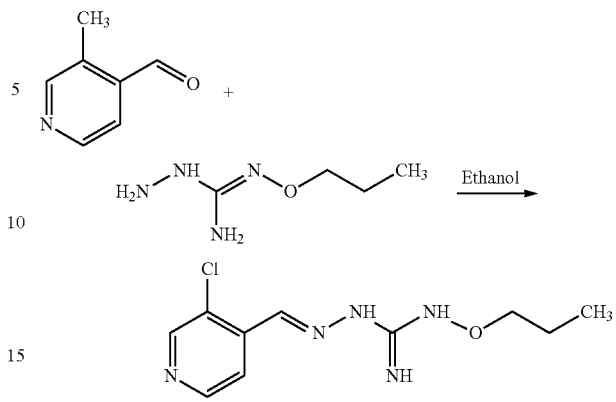

Compound 23 is prepared following the same procedure than compound 16 from 3-chloroisonicotinaldehyde and N'-(2-propoxy)hydrazinecarboximidamide (I-17) to give 2-(2-chloro-6-fluorobenzylidene)-N'-propoxyhydrazinecarboximidamide LC-MS: m/z=255.9 (M+H).

Selected compounds according to the invention are set forth in Table below:

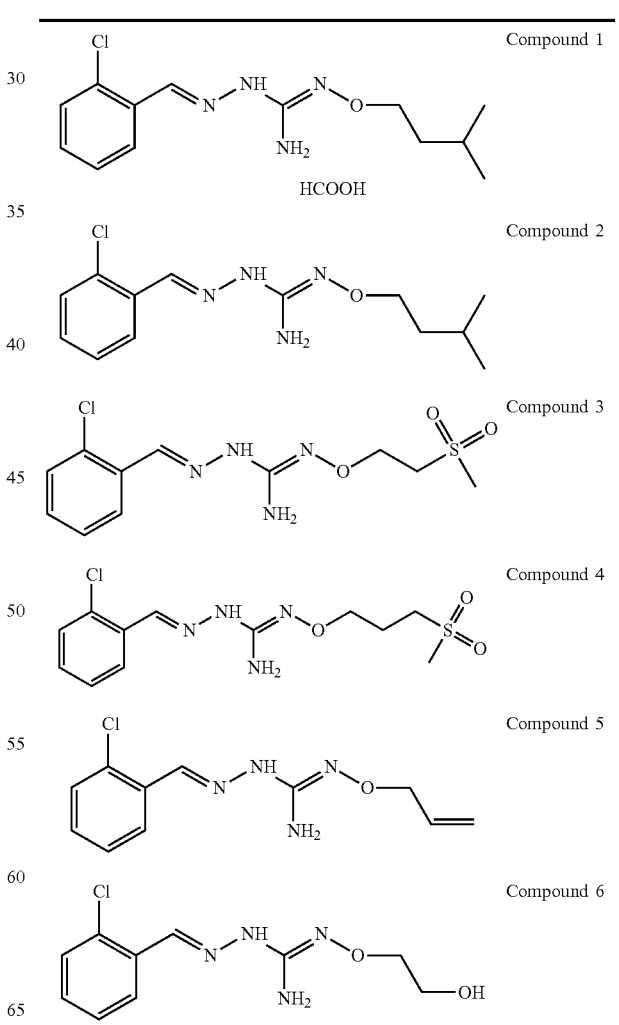

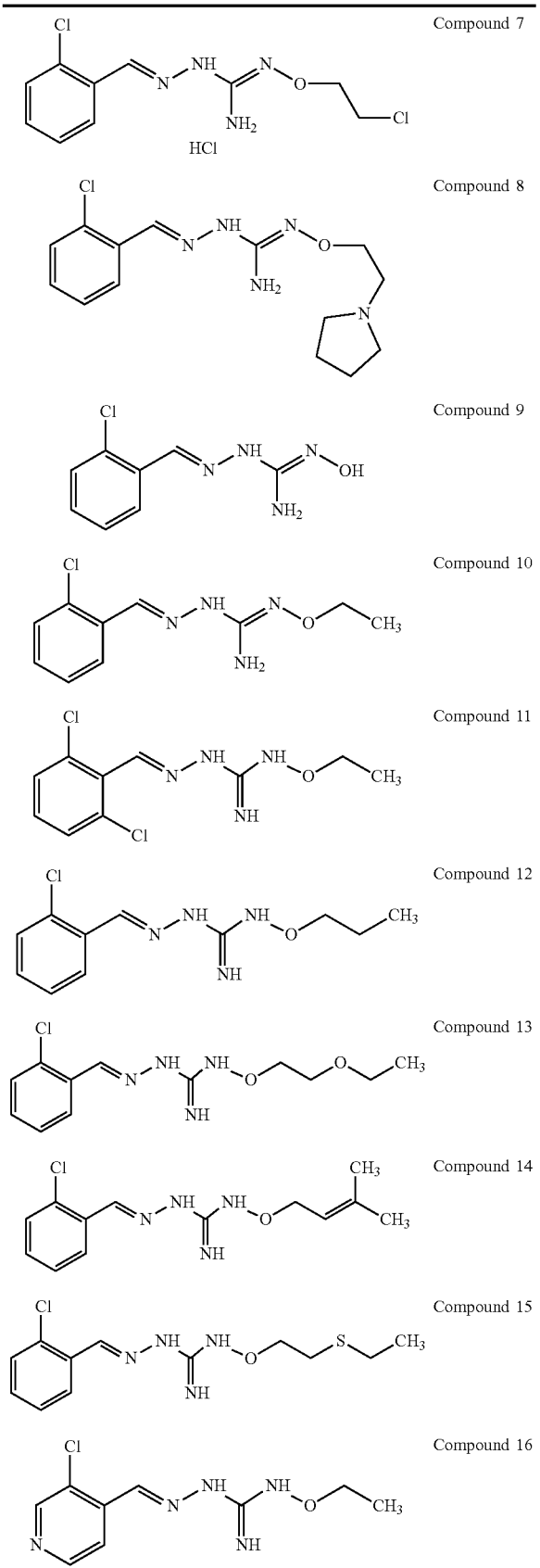
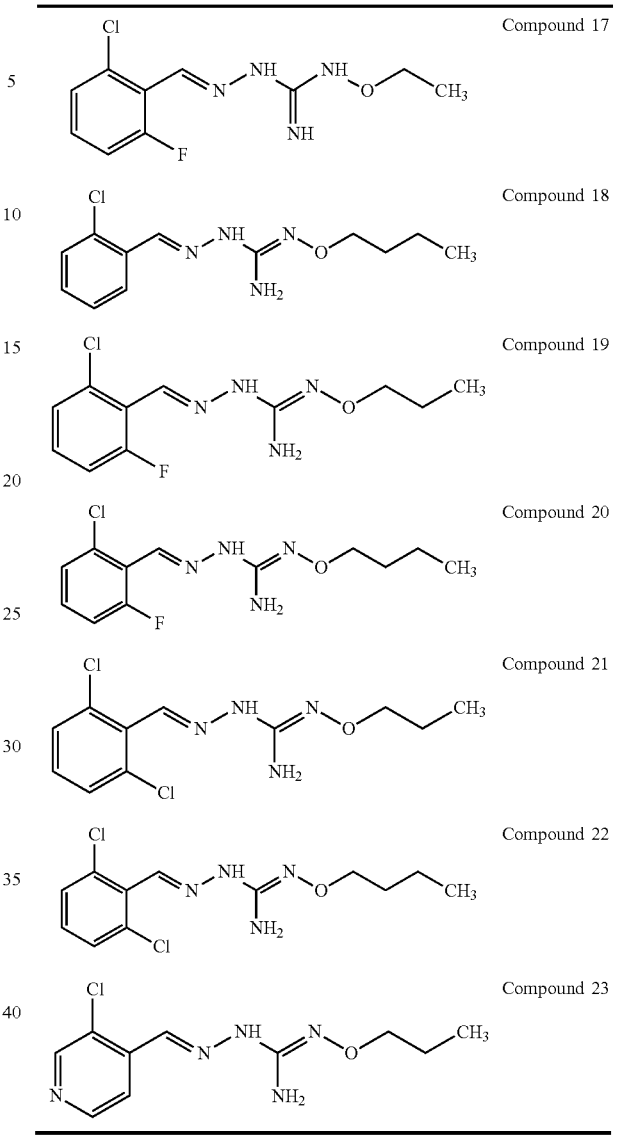

In some of the experiments below, the salt of these compounds may be used.

1.2—Mammalian Cell Culture, Constructs and Transfection

HeLa Cells were cultured in Eagle's Minimum Essential Medium (EMEM) supplemented with Glutamine, Sodium Pyruvate, Non-Essential Amino Acids, Penicillin and Streptomycin (Lonza) containing 10% Foetal Bovine Serum (FBS) (Biowest). 293T cells were cultured in Dubelcco's Modified Eagle's Media (DMEM) supplemented with penicillin, streptomycin, glutamine (Lonza) and 10% of fetal bovine serum (FBS) (Biowest).

Min6 cells were cultured in DMEM supplemented with penicillin, streptomycin, glutamine, sodium pyruvate, 50 µM f3-Mercaptoethanol and 15% Foetal Bovine Serum (FBS) (Biowest). INS1 cells were cultured in RPMI supplemented with penicillin, streptomycin, glutamine, sodium pyruvate (Lonza), 50 µM Mercaptoethanol and 10% of fetal bovine serum (FBS) (Biowest). Each cell line was maintained at 37° C. in 5% $CO_2$ atmosphere.

Human open reading frame (ORF) sequences for PLP1, DM20 and Insulin were obtained from Life Technologies (Invitrogen) (IOH41689, IOH5252 and IOH7334 respectively). Construct cloning into the expression plasmid pDEST26 (Invitrogen) was performed by Gateway® LR Clonase™ II Enzyme Mix (Invitrogen). ORF mutations were carried out using the QuikChange Lightning Site-Directed Mutagenesis Kit (Stratagene) (T181P mutation for PLP1 and DM20 ORFs, Akita (C96Y) for Insulin ORF).

Gene expression into mammalian cells was carried out by nucleofection, using the Amaxa™ 4D-Nucleofector™ System (Lonza) or by transfection using Lipofectamine (Life technologies).

1.3—Cytoprotection from ER Stress

This assay is described in Tsaytler et al. (Science 2011). HeLa Cells were cultured in Eagle's Minimum Essential Medium (EMEM) supplemented with Glutamine, Sodium Pyruvate, Non-Essential Amino Acids, Penicillin and Streptomycin containing 10% Foetal Bovine Serum (FBS), at 37° C. in 5% $CO_2$ atmosphere. Cells were plated in 96 well plates at a density of 17,000 cells/mL the day before the treatment. ER stress was elicited by addition of 5 µg/mL tunicamycin (Sigma-Aldrich) together with PPP1R15A inhibitors (0.5-10 µM). Media were changed 6h later with fresh media and the cytoprotection was maintained by the addition of PPP1R15A inhibitors (0.5-10 µM). Cell viability was assessed by measuring the reduction of WST-8 into formazan using Cell Counting Kit-8 (Sigma) according to the supplier's recommendation, 48 h or 72h after tunicamycin treatment. Cytoprotection from ER stress is measured in terms of cytoprotective potency effect compared to the reference compound Guanabenz (Tsaytler et al., Science 2011) after ER stress:
  '+' no cytoprotective effect;
  '+' lower cytoprotective effect compared to Guanabenz;
  '++' similar cytoprotective effect compared to Guanabenz;
  '+++' higher cytoprotective effect compared to Guanabenz.

Table 1 summarizes the results of cytoprotective effect of different compounds of the invention, compared to guanabenz, after the stress induced by a 6 hour exposure of tunicamycin.

1.4—Assessment of Translation Rates in Unstressed Cells

HeLa cells (100,000 cells/ml) were plated in 6-well plates 24 h before each experiment and were either left untreated or treated with compounds (50 µM) for 2.5, 5 and 9 h. Culture medium was replaced by methionine-free DMEM medium (Invitrogen) 30 min before compounds addition. One hour before each time point, 50 µM of Click-iT® AHA (L-azidohomoalanine) (Invitrogen) was added to the culture medium in order to label newly synthesized proteins. At the end of each time point, cells were washed with ice-cold PBS and harvested by Trypsine dissociation (Lonza), then lysed in a 50 mM Tris-HCl buffer containing 1% of SDS (Sigma) and protease and phosphatase inhibitors (Sigma). Protein samples were coupled to alkyne biotin (Invitrogen) using Click-iT® Protein Reaction Buffer Kit (Invitrogen). Samples were denatured at 70° C. for 10 min, resolved on ECL 4-20% precasted gels (GE Healthcare) and transferred to nitrocellulose membranes (GE Healthcare). Alkyne biotin coupled to Click-iT® AHA incorporated to newly synthesized proteins was detected using streptavidin-HRP (Gentex). Revelation was performed by incubation of ECL Prime (GE Healthcare) and read by chemoluminiscence using Fusion Solo 3S (Vilber Lourmat).

1.5—Assessment of Translation Rates in Stressed Cells

Treatments were performed as for measuring translation in unstressed cells, except that Tunicamycin (5 µg/ml) was added together with the compounds.

1.6—Functional GPCR Assay for Adrenergic α2A Receptor (Cellkey Detection Method)

The agonist activity of compounds was evaluated on CHO cells endogenously expressing human alpha2A receptor and was determined by measuring their effects on impedance modulation using the CellKey detection method. Cells were seeded onto 96-well plate at density of $6 \times 10^4$ cells/well in HBSS buffer (Invitrogen)+20 mM HEPES (Invitrogen) with 0.1% BSA and are allowed to equilibrate for 60 min at 28° C. before the start of the experiment. Plates were placed onto the system and measurements were made at a temperature of 28° C. Solutions were added simultaneously to all 96 wells using an integrated fluidics system: HBSS (basal control), reference agonist at 100 nM (stimulated control), reference agonist ($EC_{50}$ determination) or the test compounds. Impedance measurements are monitored for 10 minutes after ligand addition. The standard reference agonist is epinephrine, which is tested in each experiment at several concentrations to generate a concentration-response curve from which its $EC_{50}$ value is calculated.

Dose-response data from test compounds were analysed with Hill software using non-linear regression analysis of the concentration-response curves generated with mean replicate values using Hill equation curve fitting. Results are presented table 1, compounds with EC50>33.3 µM are considered to have no significant alpha-2 adrenergic activity.

1.7—In Vitro Multiple Sclerosis Disease Model: Interferon-Gamma Injured Rat Oligodendrocytes Co-Cultured with Neurons

Culture of Oligodendrocyte Co-Cultured with Neurons

Neurons/OPC were cultured as previously describes by Yang et al. (2005 J Neurosci Methods;149(1) pp50-6) with modifications. Briefly, the full brain (without cerebellum) obtained from 17-day old rat embryos (Wistar, Janvier labs) were removed. The full brains were treated for 20 min at 37° C. with a trypsin-EDTA (Pan Biotech) solution at a final concentration of 0.05% trypsin and 0.02% EDTA. The dissociation was stopped by addition of Dulbecco's modified Eagle's medium (DMEM) with 4.5 g/liter of glucose (Pan Biotech), containing DNAse I grade II (final concentration 0.5 mg/ml; Pan Biotech, Batch: h140508) and 10% fetal calf serum (FCS; Invitrogen, Batch: 41Q7218K). Cells were mechanically dissociated by three forced passages through the tip of a 10-ml pipette. Cells were then centrifuged at 515 g for 10 min at 4° C. The supernatant was discarded, and the pellet was resuspended in a defined culture medium consisting of Neurobasal medium (Invitrogen, Batch: 1636133) with a 2% solution of B27 supplement (Invitrogen, Batch: 1660670), 2 mmol/liter of L-glutamine (Pan Biotech), 2% of PS solution, and, 1% of FCS and 10 ng/ml of platelet derived growth factor (PDGF-AA, Batch: H131205). The cells were seeded at a density of 20 000 cells per well in 96 well plates precoated with PLL (BD corning, Batch: 6614022) and laminine (Sigma, Batch: 083M4034V). The plates were maintained at 37° C. into a humidified incubator, in an atmosphere of air (95%)-CO2 (5%). Half of the medium was changed every 2 days with fresh medium. On days 18, test compounds were pre-incubated 1 hour before interferon-gamma (70 U/ml, 48H, R&D system, Batch: AAL2214081) application.

Test Compounds and Interferon-Gamma Exposure

On day 18 of culture, test compounds (4 concentrations) were solved in culture medium and then pre-incubated with oligodendrocyte co-cultured with neurons for 1 hour before the interferon-gamma (70 U/ml, 48H) application. One hour after test compounds incubation, interferon-gamma was added at 70 U/ml concentration for 48 H still in presence of test compounds. Then, cells were fixed by a cold solution of ethanol (95%, Sigma, Batch: SZBD3080V) and acetic acid (5%, Sigma, Batch: SZBD1760V) for 5 min at −20° C. After permeabilization with 0.1% of saponin (Sigma, Batch: BCBJ8417V), cells were incubated for 2 h with Monoclonal Anti-O4 antibody produced in mouse (Sigma, batch: SLBF5997V) at dilution of $1/1000$ in PBS (PAN, Batch: 8410813) containing 1% FCS, 0.1% saponin, for 2 h at room temperature. This antibody are revealed with Alexa Fluor 488 goat anti-mouse IgG (Invitrogen, batch: 1664729) at the dilution $1/400$ in PBS containing 1% FCS, 0.1% saponin, for 1 h at room temperature.

Analysis of Total Number of O4 Cells

For each condition, 30 pictures per well were taken using ImageXpress (Molecular Device) with 20× magnification. All images were taken with the same conditions. Analysis of total number of O4 cells was performed automatically by using Custom module editor (Molecular Device). Data were expressed in percentage of control conditions (no intoxication, no interferon-gamma=100%) in order to express the interferon-gamma injury. All values were expressed as mean +/−SEM (s.e.mean) (n=6 wells per condition).

1.8- In vitro Parkinson's Disease Model: Rotenone Injured Primary Mesencephalic Rat Neurons Culture of Mesencephalic Dopaminergic Neurons Rat dopaminergic neurons were cultured as described by Schinelli et al., (1988 J. Neurochem 50 pp1900-07) and Visanji et al., (2008 FASEB J. 22(7) pp2488-97). Briefly, the midbrains obtained from 15-day old rat embryos (Janvier Labs, France) were dissected under a microscope. The embryonic midbrains were removed and placed in ice-cold medium of Leibovitz (L15, Pan Biotech, Batch: 9310614) containing 2% of Penicillin-Streptomycin (PS, Pan Biotech, Batch: 1451013) and 1% of bovine serum albumin (BSA, Pan Biotech, Batch: h140603). The ventral portion of the mesencephalic flexure, a region of the developing brain rich in dopaminergic neurons, was used for the cell preparations.

The midbrains were dissociated by trypsinisation for 20 min at 37° C. (Trypsin 0.05% EDTA 0.02%, PanBiotech, Batch: 5890314). The reaction was stopped by the addition of Dulbecco's modified Eagle's medium (DMEM, PanBiotech, Batch: 1300714) containing DNAase I grade II (0.1 mg/ml, PanBiotech, Batch: H140508) and 10% of foetal calf serum (FCS, Gibco, Batch: 41Q7218K). Cells were then mechanically dissociated by 3 passages through a 10 ml pipette. Cells were then centrifuged at 180×g for 10 min at +4° C. on a layer of BSA (3.5%) in L15 medium. The supernatant was discarded and the cell pellets were re-suspended in a defined culture medium consisting of Neurobasal (Invitrogen, Batch: 1636133) supplemented with B27 (2%, Invitrogen, Batch: 1660670), L-glutamine (2 mM, PanBiotech, Batch: 8150713) and 2% of PS solution and 10 ng/ml of Brain-derived neurotrophic factor (BDNF, PanBiotech, Batch: H140108) and 1 ng/ml of Glial-Derived Neurotrophic Factor (GDNF, Pan Biotech, Batch: H130917). Viable cells were counted in a Neubauer cytometer using the trypan blue exclusion test. The cells were seeded at a density of 40 000 cells/well in 96 well-plates pre-coated with poly-L-lysine (Corning Biocoat, Batch: 6614022) and maintained in a humidified incubator at 37° C. in 5% $CO_2$/95% air atmosphere. Half of the medium was changed every 2 days with fresh medium.

On day 6 of culture, the medium was removed and fresh medium was added, without or with rotenone (Sigma, Batch: 021M2227V) at 10 nM diluted in control medium, 3 wells per condition were assessed. Test compounds were solved in culture medium and then pre-incubated with mesencephalic neurons for 1 hour before the rotenone application.

After 24 hours of intoxication, cells were fixed by a solution of 4% paraformaldehyde (Sigma, batch: SLBF7274V) in PBS (Pan Biotech, Batch: 4831114), pH=7.3 for 20 min at room temperature. The cells were washed again twice in PBS, and then were permeabilized and non-specific sites were blocked with a solution of PBS containing 0.1% of saponin (Sigma, batch: BCBJ8417V) and 1% FCS for 15 min at room temperature. Then, cells were incubated with Monoclonal Anti-Tyrosine Hydroxylase antibody produced in mouse (TH, Sigma, batch: 101M4796) at dilution of $1/10000$ in PBS containing 1% FCS, 0.1% saponin, for 2 h at room temperature. This antibody was revealed with Alexa Fluor 488 goat anti-mouse IgG (Molecular Probes, batch: 1531668) at the dilution $1/800$ in PBS containing 1% FCS, 0.1% saponin, for 1 h at room temperature.

Analysis of Total Number of TH Positive Neurons

The immunolabeled cultures were automatically examined with ImageXpress (Molecular device USA). For each condition, 20 automatically fields per well (representing ~80% of the total surface of the well) from 3 wells were analyzed. The total number of TH neurons was automatically analyzed using Custom module editor (Molecular Devices, USA). Data were expressed in percentage of control conditions (no intoxication, no rotenone=100%) in order to express the rotenone injury. All values were expressed as mean +/−SEM (s.e. mean) of the 1 culture (n=3 wells per condition per culture).

1.9-In Vitro Alzheimer Disease Model: Amyloid-Beta 1-42 Injured Primary Cortical Rat Neurons.

Culture of Rat Cortical Neurons

Rat cortical neurons were cultured as described by Singer et al., (1999 J. Neuroscience 19 pp2455-63) and Callizot et al., (2013 J.Neurosci. Res. 91 pp706-16). Pregnant females (Wistar; Janvier Labs) at 15 days of gestation were killed by cervical dislocation. Fetuses were collected and immediately placed in ice-cold L15 Leibovitz medium (Pan Biotech, Batch: 9310614) with a 2% penicillin (10,000 U/ml) and streptomycin (10 mg/ml) solution (PS; Pan Biotech, Batch: 1451013) and 1% bovine serum albumin (BSA; Pan Biotech, Batch: h140603). Cortex was treated for 20 min at 37°

C. with a trypsin-EDTA (Pan Biotech, Batch: 5890314) solution at a final concentration of 0.05% trypsin and 0.02% EDTA. The dissociation was stopped by addition of Dulbecco's modified Eagle's medium (DMEM) with 4.5 g/liter of glucose (Pan Biotech, batch: 1300714), containing DNAse I grade II (final concentration 0.5 mg/ml; Pan Biotech, Batch: h140508) and 10% fetal calf serum (FCS; Invitrogen, Batch: 41Q7218K). Cells were mechanically dissociated by three forced passages through the tip of a 10-ml pipette. Cells were then centrifuged at 515 g for 10 min at 4° C. The supernatant was discarded, and the pellet was resuspended in a defined culture medium consisting of Neurobasal medium (Invitrogen, Batch: 1636133) with a 2% solution of B27 supplement (Invitrogen, Batch: 1660670), 2 mmol/liter of L-glutamine (Pan Biotech, Batch: 8150713), 2% of PS solution, and 10 ng/ml of brain-derived neurotrophic factor (BDNF; Pan Biotech, Batch: H140108). Viable cells were counted in a Neubauer cytometer, using the trypan blue exclusion test. The cells were seeded at a density of 30,000 per well in 96-well plates precoated with poly-L-lysine (Corning Biocoat, Batch: 6614022) and were cultured at 37° C. in an air (95%)-$OO_2$ (5%) incubator. The medium was changed every 2 days. The cortical neurons were intoxicated with A-beta solutions (see below) after 11 days of culture.

Test Compounds and Amyloid-Beta 1-42 Exposure

The Amyloid-beta1-42 preparation was done following the procedure described by Callizot et al., 2013. Briefly, Amyloid-beta 1-42 peptide (Bachem, Batch: 1014012) was dissolved in the defined culture medium mentioned above, devoid of serum, at an initial concentration of 40 μmol/liter. This solution was agitated for 3 days at 37° C. in the dark and immediately used after being properly diluted in culture medium to the concentrations used. Test compounds were solved in culture medium and then pre-incubated with primary cortical neurons for 1 hour before the Amyloid-beta 1-42 application. Amyloid-beta 1-42 preparation was added to a final concentration of 20 μM (including to ~2 μM of toxic oligomers measured by WB) diluted in control medium in presence of drugs. After 24 hours of intoxication, cells were fixed by a cold solution of ethanol (95%, Sigma, Batch: SZBD3080V) and acetic acid (5%, Sigma, Batch: SZBD1760V) for 5 min at −20° C. After permeabilization with 0.1% of saponin (Sigma, Batch: BCBJ8417V), cells were incubated for 2 h with mouse monoclonal antibody anti microtubule-associated-protein 2 (MAP-2; Sigma, Batch: 063M4802) at dilution of 1/400 in PBS (Pan biotech, Batch: 4831114) containing 1% foetal calf serum (Invitrogen, Batch: 41Q7218K) and 0.1% of saponin. This antibody was revealed with Alexa Fluor 488 goat anti-mouse IgG
(Molecular probe, Batch: 1572559) at the dilution of 1/400 in PBS containing 1% foetal calf serum and 0.1% of saponin for 1 H at room temperature.

Analysis of Total Number of Neurons

The immunolabeled cultures were automatically examined with ImageXpress (Molecular device USA) at ×20 magnification. For each condition, 30 automatically fields per well (representing ~80% of the total surface of the well) from 3 wells were analyzed. The total number of neurons was automatically analyzed using Custom module editor (Molecular Devices, USA). Data were expressed in percentage of control conditions (no intoxication, no Amyloid-beta 1-42=100%) in order to express the A-beta 1-42 injury. All values were expressed as mean +/−SEM (s.e.mean) (n=3 wells per condition per culture).

1.10- In Vitro Model of Leukodystrophy (PMD): Overexpression of Mutated PLP1 and DM20 In Human Cell Line One day before transfection, 293T cells were plated at 300,000 cells/mL. 293T cells were transfected with PLP1 and DM20 mutant constructs using Lipofectamine 2000 according to manufacturer's procedure. After transfection, cells were treated with molecules or left untreated.
As a control, cells were transfected with native forms of the proteins. 48h later, cellular lysates were harvested. Protein accumulation was assessed by western-blot.

1.11-In Vitro Model of Type 2 Diabetes: Min6 And INS1 Cell Lines Cytoprotection from ER Stress Cells were plated in 96 well plates at a density of $0.5.10^6$ cells/mL for Min6 cell line, $0,4.10^6$ cells/mL for INS1 cell line the day before the treatment. ER stress was elicited by addition of 2.5 μg/mL tunicamycin (Sigma Aldrich) together with phosphatases inhibitors. Media were changed 6h later with fresh media and the cytoprotection was maintained by the addition of phosphatases inhibitors. Cell viability was assessed by measuring the reduction of WST-8 into formazan using Cell Counting Kit-8 (Sigma) according to the supplier's recommendation, 72h after tunicamycin treatment.

Protection Against Accumulation of Misfold Prone Insulin$^{Akita}$

Min6 cells were nucleofected with Insulin$^{Akita}$ mutant constructs and seeded in 96 well-plates at 300,000 cells/mL and 24h later, cells were treated with molecules or left untreated. As a control, cells were nucleofected with non-relevant plasmid. 6 days later, a selective agent was added (G418). Cell viability was assessed by measuring the reduction of WST-8 into formazan using Cell Counting Kit-8 (Sigma) according to the supplier's recommendation, 9 days after treatment.

1.12-In Vitro Inflammation/Infection Disease Model: Poly I:C Induced Mouse Embryonic Fibroblasts Experimental Protocols Mouse Embryonic Fibroblasts (MEFs) were lipofected with poly I:C and treated with two concentrations of compounds of the invention (25 μM) for 6h. After 6h of culture, eIF2alpha-phosphorylation (eIF2a-P) and PPP1R15A (GADD34) expression was monitored by western blotting, while type-1 Interferon(IFN)-beta production was quantified in culture supernatants by ELISA. Control (nt) and poly I:C/DMSO are respectively negative and positive controls. Poly I:C (polyinosinic:polycytidylic acid or polyinosinic-polycytidylic acid sodium salt) is an immunostimulant used to simulate viral infections. Poly I:C which is structurally similar to double-stranded RNA, is known to interact with toll-like receptor 3 which is expressed in the intracellular compartments of B-cells and dendritic cells. Guanabenz (25 μM) was used as reference inhibitory compound.

Cell Culture

MEFs were cultured in DMEM, 10% FCS (HyClone, Perbio), 100 units/ml penicillin, 100 μg/ml streptomycin, 2 mM glutamine, 1× MEM non-essential amino acids and 50 μM 2-mercaptoethanol. MEFS were treated for the indicated time with 10 μg/ml poly I:C (InvivoGen) in combination with lipofectamine 2000 (Invitrogen).

Immunoblotting

Cells were lysed in 1% Triton X-100, 50 mM Hepes, 10 mM NaCl, 2.5 mM $MgCl_2$, 2 mM EDTA, 10% glycerol, supplemented with Complete Mini Protease Inhibitor Cocktail Tablets (Roche). Protein quantification was performed using the BCA Protein Assay (Pierce). 25-50 μg of Triton X-100-soluble material was loaded on 2%-12% gradient or 8% SDS-PAGE before immunoblotting and chemi-luminescence detection (SuperSignal West Pico Chemi-luminescent Substrate, Pierce). Rabbit polyclonal antibodies recognizing GADD34 (C-19) were from Santa Cruz Biotechnology and anti-elF2alpha[$pS^{52}$] were from Invitrogen.

Elisa

IFN-beta quantification in culture supernatant was performed using the Mouse Interferon Beta ELISA kit (PBL Interferon Source) according to manufacturer instructions.

1.13—Hypoxia-Induced Apoptosis in Cultured Neonatal Rat Cardiomyocytes

Cell Culture

Primary cultures of neonatal rat cardiomyocytes were obtained from the ventricles of 1-day-old Sprague Dawley rats (Janvier, France). The rats were euthanized and their hearts excised. Hearts cut into small pieces (1-2 $mm^3$) and enzymatically digested using the Neonatal Heart Dissociation Kit rat and the gentleMACS™ Dissociator (MiltenyiBiotec, Germany). After dissociation, the homogenates were filtered (70 μm) to obtain a single-cell suspension. Isolated cells were collected by centrifugation and resuspended in Dulbecco's Modified Eagle's Medium (DMEM) containing 10% horse serum (HS), 5% fetal bovine serum (FBS) and 1% penicillin/streptomycin. Cultures were enriched with myocytes by pre-plating for 90 min to deplete the population of non-myocytes. Non-attached cells were plated onto 6- or 96-well plates at an appropriate cell density. The cells were cultured at 37° C. in 95% air/5% $CO_2$ for 24 h. Then the culture medium was exchanged with fresh DMEM containing 1% FBS and different concentrations of test compound thirty minutes before incubation in a normal or a hypoxic ($N_2/CO_2$, 95%/5%; 0.3% $O_2$) culture chamber.

Treatment with Test Compound

Purified neonatal rat cardiomyocytes were seeded in a 96-well plate at $10^6$ cells/2 mL for flow cytometry experiments.

After 24 hours, the cardiomyocytes were treated with different concentrations of test compound in culture medium with 0.1% DMSO. The positive controls cells were treated with culture medium (0.1% DMSO). Thirty minutes after starting the treatments, the cells were incubated in the hypoxic culture chamber ($N_2/CO_2$, 95%/5%; final measured $O_2$: 0.3%) for 36 hours. The negative controls cells were left in normoxic conditions at 37° C. with culture medium (1% FBS, 0.1% DMSO) for the same time periods.

Apoptotic Cell Measurement

At the end of the treatment period, flow cytometry were performed to measure the amount of apoptotic cells. The Annexin V-fluorescein isothiocyanate (FITC) apoptosis detection kit from Miltenyi was used. Cells were washed twice with PBS and re-suspended in binding buffer. FITC-Annexin V and propidium iodide were added according to the manufacturer's protocol. The mixture was incubated for 15 min in the dark at room temperature, and cellular fluorescence was then measured by FACS scan flow cytometry.

2—RESULTS 2.1—Cytoprotection & Compound Selectivity

The results of the different assays ran with selected compounds of the invention are shown below in Table 1.

As example, FIG. 1 represents the cytoprotective effect of compound 12 after the stress induced by an exposure of tunicamycin.

TABLE 1

| Compound N° | Cytoprotection from ER stress compared to guanabenz | Functional adrenergic alpha2 receptor assay |
|---|---|---|
| 1 | + | |
| 2 | + | |
| 3 | + | |
| 4 | ++ | |
| 5 | + | |
| 6 | ++ | EC50 > 33.3 μM |
| 7 | + | |
| 8 | + | |
| 9 | + | |
| 10 | ++ | EC50 > 33.3 μM |
| 11 | +++ | EC50 > 0.7 μM |
| 12 | +++ | EC50 > 33.3 μM |
| 13 | ++ | EC50 > 33.3 μM |
| 14 | ++ | |
| 15 | ++ | EC50 > 33.3 μM |
| 16 | + | EC50 > 33.3 μM |
| 17 | +++ | EC50 > 33.3 μM |
| 19 | +++ | |
| 21 | ++ | |
| 23 | ++ | |

2.2—Multiple Sclerosis

FIG. 2 shows dose dependent protection of interferon-gamma injured rat oligodendrocytes by compounds 11, 12 and 17 of the invention.

These data show that the compounds of this invention are promising effective treatment of Multiple Sclerosis.

2.3—Parkinson's Disease (PD)

FIG. 3 shows dose dependent protection of rotenone injured primary mesencephalic rat neurons by compounds 5, 11 and 12 of the invention.

These data show that the compounds of this invention are promising effective treatment of synucleopathies, and more specifically Parkinson's disease.

2.4—Alzheimer Disease (AD) & Amyloidosis

FIG. 4 shows dose dependent protection of amyloid-beta 1-42 injured primary cortical rat neurons by compound 12 of the invention.

These data show that the compounds of this invention are promising effective treatment of Amyloidosis and more specifically Alzheimer disease.

2.5—Leukodystrophy: Pelizaeus-Merzbacher Disease (PMD),

T181P and L223P mutations in PLP1 and DM20 proteins have been described to cause a severe phenotype of Pelizaeus-Merzbacher disease (Strautnieks et al. 1992, Am. J. Hum. Genet. 51 (4): 871-878; Gow and Lazzarini, 1996 Nat Genet. 13(4):422-8).

The Compound 12 and 17 of the invention (5 microM) is able to prevent the accumulation of T181P mutated DM20 protein expressed in Human 293T cell (FIG. 5).

These data show that the compounds of this invention, specifically compounds 12 and 17, are promising effective treatment of demyelinating disorders like leukodystrophies, more specifically PMD.

2.6—Type 2 Diabetes

FIG. 6 represents the results of over expression of pre-pro-insulin bearing Akita mutation in Min6 cells with compound 16 of the invention.

The compounds 12, 16 and 17 at different concentrations prevent Min6 insulinoma cell death associated with accumulation of misfolded protein induced by 6 hour exposure to tunicamycin (FIG. 7)

The compounds 11, 12, 16 and 17 at different concentrations prevent INS1 insulinoma cell death associated with accumulation of misfolded protein induced by 6 hour exposure to tunicamycin (FIG. 8).

These data show that the compounds of the invention are promising effective treatment of pre-diabetes and diabetes, preferably type 2 pre-diabetes and type 2 diabetes.

2.7- Infection-Related or Non-Infectious Inflammatory Conditions

Normal response of MEFs to poly I:C is characterized by PPP1R15A expression, increase in elF2alpha-P (variable in time and related to the levels PPP1R15A expression) mediated by PKR activation and type-I IFN production (range 500 to 700 pg/ml). Knock out PPP1R15A MEFs are unable to produce this cytokine in response to poly I:C.

The potency of compounds of the invention to inhibit PPP1R15A was evaluated by measuring the increase of elF2alpha phosphorylation, the decrease of PPP1R15A expression due to its own pharmacological inhibition resulting in general protein synthesis inhibition and type-I IFN production.

The evaluated compounds of the invention were found efficient at 25 µM to increase elF2alpha phosphorylation, to decrease of PPP1R15A expression and to prevent type-I IFN production. As example, FIG. 9 shows the ability of compounds 6, 10, 11, 12, 15, 16 and 17 (at 25 microM) to prevent type-I IFN production by mouse embryonic fibroblasts lipofected with poly I:C.

These data show that the compounds of this invention are promising effective treatment of infection-related or non-infectious inflammatory conditions.

2.8-Cardiac Ischemia

Compound 10 of the invention protects cultured neonatal rat cardiomyocytes from hypoxia-induced apoptosis (FIG. 10). These data show that the compounds of this invention are promising effective treatment of ischemia, specifically cardiac ischemia.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

What is claimed is:

1. A method for treating a disease associated with protein misfolding stress comprising administering a compound of formula (II):

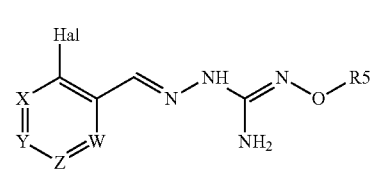

(II)

or a tautomer form thereof,
or a pharmaceutically acceptable salt thereof
wherein:
Hal=F, Cl, Br, I
X is either $-CR1=$ or $-N=$,
Y is either $-CR2=$ or $-N=$,
Z is either $-CR3=$ or $-N=$,
W is either $-CR4=$ or $-N=$,
R1 is selected from the group consisting of H, Hal, and alkyl;
R2 is selected from the group consisting of H, Hal, alkyl, and C(O)R6;
R3 is selected from the group consisting of H, Hal, alkyl and O-alkyl;
R4 is H, Cl, F, I or Br;
R5 is alkyl, cycloalkyl, aralkyl, alkenyl, cycloalkenyl, heterocyclyl, aryl, C(O)-alkyl, and C(O)-aryl, each of which is optionally substituted with one or more R7 groups;
R6 is selected from the group consisting of OH, O-alkyl, O-aryl, aralkyl, $NH_2$, NH-alkyl, $N(alkyl)_2$, NH-aryl, $CF_3$, alkyl, and alkoxy; and
each R7 is independently selected from the group consisting of halogen, OH, CN, COO-alkyl, aralkyl, heterocyclyl, alkyl, SO-alkyl, $SO_2$-alkyl, $SO_2$-aryl, COOH, CO-alkyl, CO-aryl, $NH_2$, NH-alkyl, $N(alkyl)_2$, $CF_3$, alkyl, and alkoxy;
to a patient in the need thereof.

2. The method according to claim 1 wherein Hal is Cl.

3. The method according to claim 1 wherein X is $-CR1=$ and R1 is H or F.

4. The method according to claim 1 wherein Y is $-CR2=$ and R2 is H or F.

5. The method according to claim 1 wherein $Z=-CR3=$ and R3 is H or F.

6. The method according to claim 1 wherein $W=-CR4=$ and R4 is H, Cl or F.

7. The method according to claim 1 wherein R5 is alkenyl or alkyl, each of which is optionally substituted with one or more R7 groups selected from the group consisting of halogen, OH, heterocyclyl, S-alkyl, SO-alkyl, $SO_2$-alkyl, and O-alkyl.

8. The method according to claim 1 wherein the compound is selected from the group consisting of the following:

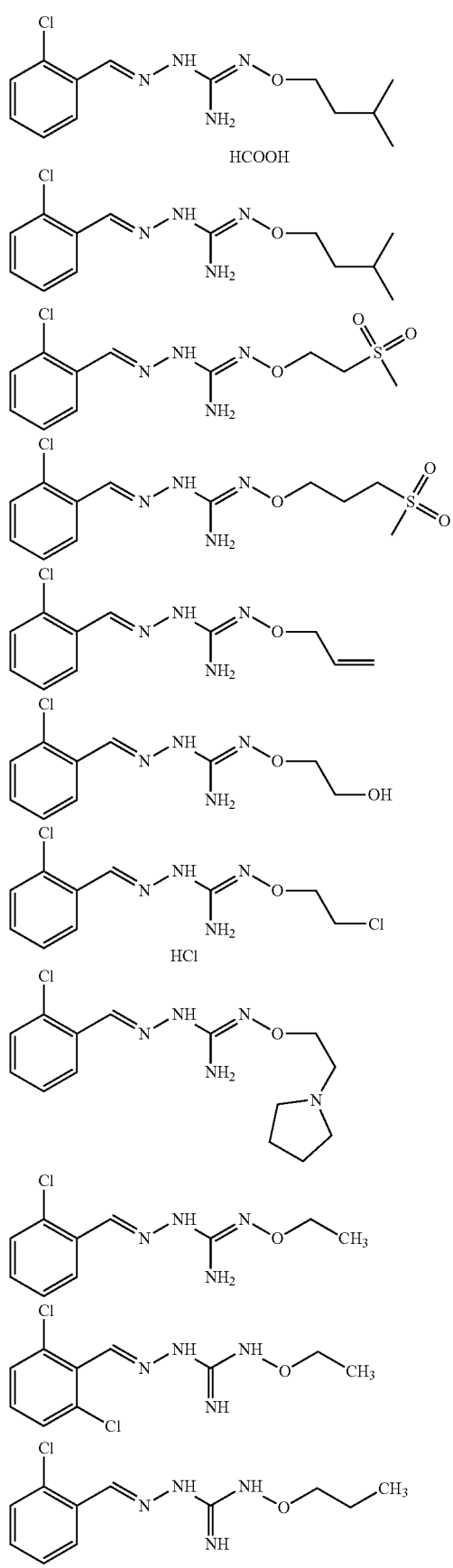
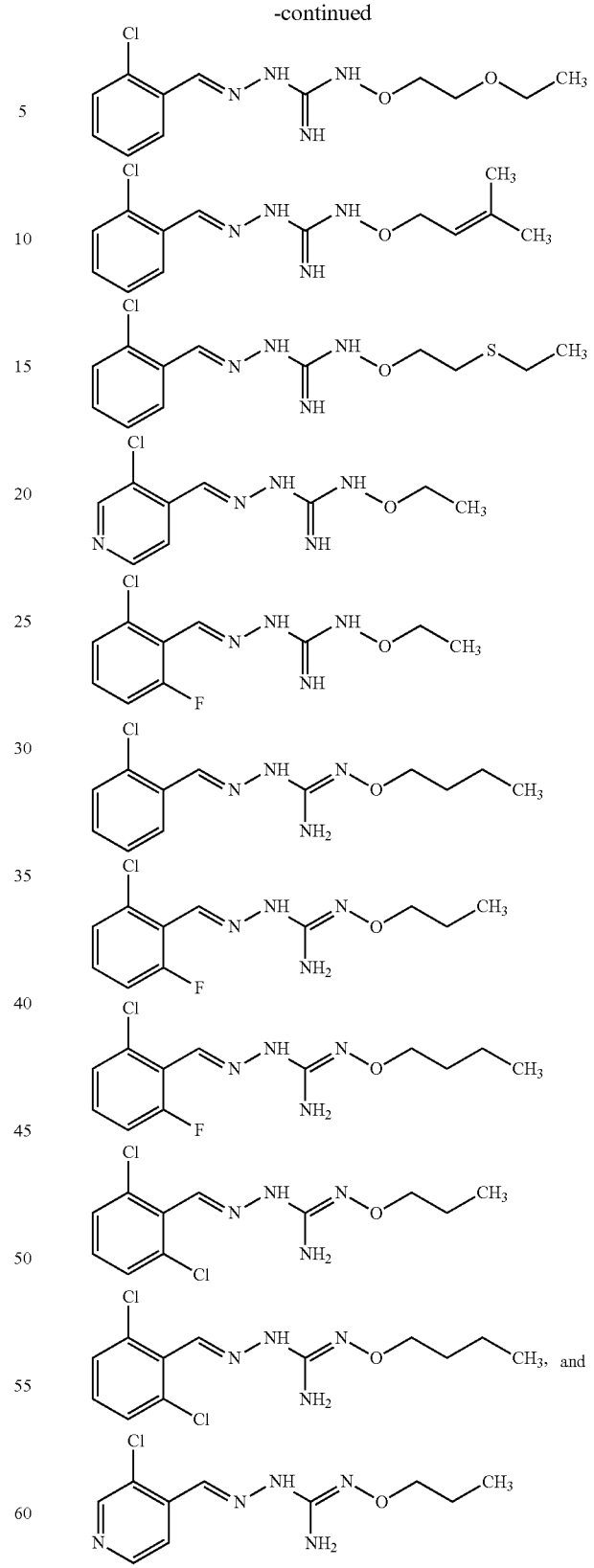
or acceptable salt thereof.
9. The method according to claim 1 wherein the disease is associated with the PPP1R15A pathway.

10. The method according to claim 1 wherein the disease is a tauopathy selected from the group consisting of Alzheimer disease, progressive supranuclear palsy, corticobasal degeneration, frontotemporal lobar degeneration or frontotemporal dementia (FTD) (Pick's disease); synucleinopathies chosen from Parkinson's disease, dementia with Lewy bodies, pure autonomic failure, and multiple system atrophy; polyglutamine and polyalanine diseases selected from the group consisting of Huntington disease, spinobulbar muscular atrophy (or Kennedy disease), dentatorubral-pallidoluysian atrophy, Spinocerebellar ataxia type 1, Spinocerebellar ataxia type 2, Spinocerebellar ataxia type 3 (or Machado-Joseph disease), Spinocerebellar ataxia type 6, Spinocerebellar ataxia type 7 and Spinocerebellar ataxia type 17, oculo-pharyngeal muscular dystrophy, demyelinating disorders like leukodystrophies, Charcot-Marie-Tooth disease and multiple sclerosis, cystic fibrosis, chosen from systemic lupus erythematosus, pancreatitis, sepsis, colitis, ulcerative colitis, Inflammatory Bowel Disease, Systemic Inflammatory Response Syndrome (SIRS), cancers, diabetes, amyotrophic lateral sclerosisseipinopathies, lysosomal storage disorders, amyloidosis diseases, inflammation, metabolic disorders and cardio-vascular disorders chosen from adiposity, hyper-lipidemia, familial hyper-cholesterolemia, obesity, atherosclerosis, hypertension, heart diseases, cardiac ischaemia, stroke, myocardial infraction, trans-aortic constriction, vascular stroke;

osteoporosis, nervous system trauma, ischemia, osteoporosis, retinal diseases selected from the group consisting of retinitis pigmentosa, retinal ciliopathies, glaucoma, macular degeneration and aging.

11. The method according to claim 1 wherein the disease associated with protein misfolding stress is associated with an accumulation of misfolded proteins.

\* \* \* \* \*